US009095103B1

(12) United States Patent
Tamulonis et al.

(10) Patent No.: US 9,095,103 B1
(45) Date of Patent: Aug. 4, 2015

(54) METHODS AND COMPOSITIONS FOR SELECTING SOYBEAN PLANTS RESISTANT TO BROWN STEM ROT

(71) Applicant: Monsanto Technology LLC, St. Louis, MO (US)

(72) Inventors: John Patrick Tamulonis, Woodland, CA (US); Charlotte A. Sartell, Whitewater, WI (US); Vergel C. Concibido, Maryland Heights, MO (US); Andrew D. Nickell, Ankeny, IA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/087,257

(22) Filed: Nov. 22, 2013

Related U.S. Application Data

(62) Division of application No. 13/230,587, filed on Sep. 12, 2011, now abandoned, which is a division of application No. 12/165,744, filed on Jul. 1, 2008, now abandoned.

(60) Provisional application No. 60/948,367, filed on Jul. 6, 2007.

(51) Int. Cl.
*C12Q 1/68* (2006.01)
*A01H 1/04* (2006.01)

(52) U.S. Cl.
CPC ........................................ *A01H 1/04* (2013.01)

(58) Field of Classification Search
None
See application file for complete search history.

(56) References Cited

U.S. PATENT DOCUMENTS 5,689,035 A 11/1997 Webb
5,948,953 A 9/1999 Webb
2006/0041955 A1* 2/2006 Godwin et al. ............... 800/279
2006/0288444 A1 12/2006 McCarroll et al.

FOREIGN PATENT DOCUMENTS

WO WO 2008153804 * 12/2008

OTHER PUBLICATIONS

Bachman et al. Crop Science (2001) 41:527-535.*
Bachman et al., “Molecular Markers Linked to Brown Stem Rot Resistance Genes, Rbs1 and Rbs2, in Soybean”, Crop Science, 2001, pp. 527-535, vol. 41.
Cregan et al., “An Integrated Genetic Linkage Map of the Soybean Genome”, Crop Science, 1999, pp. 1464-1490, vol. 39.
Hanson et al., “Identification of Two Dominant Genes Conditioning Brown Stem Rot Resistance in Soybean”, Crop Science, 1988, pp. 41-43, vol. 28.
Patzoldt et al., “Characterization of Resistance to Brown Stem Rot of Soybean in Five Accessions From Central China”, Crop Science, 2005, pp. 1092-1095, vol. 45.
Willmot et al., “Genetic Analysis of Brown Stem Rot Resistance in Soybean”, Crop Science, 1989, pp. 672-674, vol. 29.
Yang et al., “Molecular mapping of a new gene for resistance to frogeye leaf spot of soya bean in ‘Peking’”, Plant Breeding, 2001, pp. 73-78, vol. 120, Issue 1.

* cited by examiner

*Primary Examiner* — Medina A Ibrahim
(74) *Attorney, Agent, or Firm* — Thompson Coburn LLP; William A. Holtz

(57) ABSTRACT

The present invention is in the field of plant breeding and disease resistance. More specifically, the invention includes methods and compositions for breeding soybean plants containing quantitative trait loci that are associated with resistance to Brown Stem Rot (BSR), a fungal disease associated with *Philophora* spp. The invention further includes germplasm and the use of germplasm containing quantitative trait loci (QTL) conferring disease resistance for introgression into elite germplasm in a breeding program for resistance to BSR.

14 Claims, 1 Drawing Sheet

| Marker | SEQ ID NO. | Favorable allele | Effect-absolute value | Std. Error | t_value | p-value | Mean BSR rating for lines homozygous favorable allele | Number of lines homozygous favorable allele | Mean BSR rating for lines homozygous other allele | Number of lines homozygous other allele |
|---|---|---|---|---|---|---|---|---|---|---|
| NS0097011 | 4 | GTAGTATA | 0.3 | 0.097 | 3.57 | 0.000 | 3.7 | 738 | 4.4 | 133 |
| NS0096111 | 7 | A | 0.7 | 0.094 | -7.80 | 0.000 | 3.5 | 537 | 5.0 | 162 |
| NS0136255 | 9 | T | 1.0 | 0.101 | 9.41 | 0.000 | 3.5 | 606 | 5.4 | 122 |
| NS0115388 | 8 | C | 0.5 | 0.183 | -2.92 | 0.004 | 3.7 | 722 | 4.8 | 34 |
| NS0098342 | 15 | C | 1.0 | 0.106 | -9.57 | 0.000 | 3.2 | 487 | 5.3 | 93 |
| NS0125407 | 16 | C | 0.9 | 0.081 | 11.24 | 0.000 | 3.2 | 481 | 5.0 | 203 |
| NS0097529 | 19 | A | 1.1 | 0.097 | -11.65 | 0.000 | 3.2 | 480 | 5.5 | 111 |
| NS0097836 | 22 | G | 1.2 | 0.164 | 7.25 | 0.000 | 3.5 | 629 | 5.9 | 37 |
| NS0115925 | 23 | A | 1.1 | 0.116 | -9.54 | 0.000 | 3.6 | 685 | 5.8 | 84 |
| NS0117865 | 24 | A | 1.1 | 0.106 | -10.31 | 0.000 | 3.5 | 611 | 5.6 | 104 |
| NS0118789 | 31 | C | 1.2 | 0.079 | -15.41 | 0.000 | 3.1 | 502 | 5.5 | 192 |

SEQUENCE LISTING

```
<160> NUMBER OF SEQ ID NOS: 174

<210> SEQ ID NO 1
<211> LENGTH: 745
<212> TYPE: DNA
<213> ORGANISM: Glycine max

<400> SEQUENCE: 1

aaacaaagta aaagggttgc tgggaaaata agctgagggg gcgtgctgaa ttttttttct      60

tccaacatga cttgttaatt tgcaatatta aaatggaaac acatatggat cattatattc     120

agtatcttta ttagataaag atgaggaaaa tgtttataaa aaattcaatt aatagcgttg     180

ttagcaaaga ataacagtta aagaaattca ttttttaaga cacatccaca tcaaattgaa     240

ttcataggaa tgtcaaaaac aagagacaga tctttctgtc gatatgacca attctggtaa     300

ttaaaaatac tagtttctat ctccatgggt cgcatagtac tatgttcata ctggcagcag     360

cttgatccta gccacaaggt gcttttaggg ggttaatttc aaacactgca agtaaagtcc     420

aacctcataa gagattgatt ttcatcttaa acttcattgc gttattttat tatttcatcc     480

aaaaatgcta taagtttgga ttcttgtttg actttgggga cccaacccaa gactcattca     540

tctacaatca tacattcaat actgacctct cttctcagtt ctcatgacta tgcaaccatc     600

ctcatcttcc tttggttatg gattcaccta cgatgtgttc cttagcttca gaggggaaga     660

tactcgttac ggtttcactg gcaatctcta caaagctctt tatgacaagg gaattcacac     720

cttcatcgat gaggagctgc aggca                                           745

<210> SEQ ID NO 2
<211> LENGTH: 867
<212> TYPE: DNA
<213> ORGANISM: Glycine max

<400> SEQUENCE: 2

agtcgacctg cagcaactga aattgagtta gctaaaaggg tgaaagactt ctccttcaag      60

gagacagggt actttttatt tccgttttcc ctgtaaaaga cagtggcttg cattcttggg     120

gatacattga tgtgttgttt tcacacacat gcctcttcca ttcattgaat tttttttaac     180

tacatgagga attttgtttg tatgattttg ccttatggtt atttggggta taaggctatc     240

aatatccagt tatgatttta taaacatttt atttcatttg ctgaagtcca tgtaacttgt     300

aaggcacttt ttagcaagtg caatattgga gagatgcact tgtgggtaaa aaggacttgt     360

accattattc taattttgat cttaaacaaa aaagaagttt aatatgttta tttgcaagta     420

tgtgcaactg attataaact tgtggggact tctgtaacaa tttttgttta ccaagttgtg     480

tacgtttgat actgacatgc attaacatgc cttcattatt atgtatttgc atctcattgg     540

cttttagccc ttaggaatca ttcaccacta acgtagaaat gctgctcttt ttttatcacc     600

tgtcttgtgc agtttattgg gatatgtcaa tatctttttg ttatcgagaa ttattaaagt     660
```

```
cggtataaca taaatgtgtt ctaaaatcta acttgatctt ggatgttttt aacccagcac    720

catatattac tgtgtattat ttggaaatag ttactgtctc tattcactgg acttaattta    780

ttttgttcaa tgcttatttg gtatttgaca cgggaatgga atggactaaa catttgcaat    840

ggccctgcaa ggcatgcaag cttggcg                                        867
```

<210> SEQ ID NO 3
<211> LENGTH: 1560
<212> TYPE: DNA
<213> ORGANISM: Glycine max

<400> SEQUENCE: 3

```
aggcttgcat gcctgcagtc tcatgacaaa gaaagatccc ataacattat caagcaccta     60

gtaaaaagtg gttgtaagaa attatgaaat gcagaaatca ggaagtgtta ttttcaagtt    120

gcaacatgtg agtgtattga taaaactgaa tactttcagt tagctgttgt tgtaagagag    180

cagttacaaa ctgactctct attagttagg gtacagctgt catctagaca gctcatctgt    240

aaatactgag ttgtaatcct aaactcattg actgaaatga aattcagatc cctttactct    300

cttttcagtt ttctctctca tttcaacaca acacacacta taaatatttc ttgtataatc    360

ctagcataaa tatctatcta tttttctacc ccagtgggct caatcaaaaa tcaaaatctc    420

agggatatta tacaccatga catgtctcta aacaatttcc tccaacgtct ttcctaactt    480

caactcccta ataatataaa agtatgccca gaaaaccaac atatgcacag gttatggtca    540

tgtttaatct ttatgtacaa agaattttca tatccttatt ggcaagggct atgtctacat    600

acatatcatt tagacatttt cctactcggt ttggtacatc tattaacaat aatgatagca    660

ccaacacaat taaggatcat ttaagttttt attgagaaaa aaaatatgag aaacaaccaa    720

tgaaaaagtt atggacactt caccccctt ccccccccc cccccacaaa aaaaaaaaca    780

aaaacaaata cctactgttg ataacatcat ctgcagcagt ttccccgcta agcataacac    840

agtctgtgcc atcaaggact gcattggcaa catcggtggc ctcggctcgt gtaggccgag    900

gagatttgat catggactct aacatctggg tggctgtcac cacaggcttg cctttaatgt    960

ttgacttgtg tatcataact ttctgagcta gaaagatctt ctcaattgga atttccattc   1020

ccaggtcacc tcttgccacc atgaatgcat ctgaattttc cagtatttca tcaaaatttg   1080

caacaccctc ttgattttca acctaacaaa gacaacaaat aagtacaatt tgggagatta   1140

atcaatgcca gaactttgtt tcttgttttc atagacttgt acggagagct tatacgtatg   1200

tttgaaaata gaatcaaagt gaaagtaaaa tgacatttct gtaaattatt tgaagagtta   1260

aagtaaaaca gaatacattt acttgagaat aaggatggat accttggaca tgagaagtat   1320

gctttttgca tgctttccaa gtacatttct gacctccaca aggtctgaac tttttctaac   1380

aaaagagaga gcaatgatat caatcttatt aggaaccccc cactccaaaa tgtcctcctt   1440

gtccttctct gtcaagattg gaagatcaac aaccactcca ggaaggttaa cattcttcct   1500

ctcccccaga actgcagagc atgcaagctt tggccgtaaa ccatgggtca taagctggtt   1560
```

<210> SEQ ID NO 4
<211> LENGTH: 768
<212> TYPE: DNA
<213> ORGANISM: Glycine max

<400> SEQUENCE: 4

```
ttgcatgcct gcagtgtttg agagtactta gataagtaat tggttacatt tcaaaatact     60

ccaaacaagt agatatttat atcgtaagac cttttatatg tactgcttct tgcttaaact    120
```

```
gggaaatgga aatcgaattt atttatgtgt aaaagctctt tacaatatat ggtacaaaat    180

attgaaattc ttacaatgaa ctcttaaata actcggacaa tatatactct ccattacaac    240

tcaagatgta ccaaactgca ccttaaataa ttcagccact atttatgata aatattttca    300

agcatatcac atctcacaca tgtgagaatt atagtggaaa aatagtagta tattaaagca    360

atttatcttg tcacgctcat atgaaatgat tagattcata aagaaaaacc aaacatttag    420

ccctgacata ttgtaaaata aaattcaaaa agtaattagc cgactgaaat agagaatctg    480

cccaaaaata taaagcaaaa gtgttattta actacttcac tgtcaagtac tcacagtatt    540

ggtcaattta attaaatttc ccaggattgg cagcatcaat gatggggata tttagtcatg    600

gggaaaaaaa agaaaagggc acatacactc agctttcctg gaagttactg caaatatgca    660

aatctgccca tgcggatcac attgcaattt atacattttc tatattacag tagtatcttt    720

aaattattta gaggattcaa taatatatag aattatcata gaatactt                 768


<210> SEQ ID NO 5
<211> LENGTH: 366
<212> TYPE: DNA
<213> ORGANISM: Glycine max

<400> SEQUENCE: 5

gctgctaagg ctcttggatc attcaggagc aaccccacta tttgagtcaa tttcctcttc     60

atggggggtt agtggaaatg gaaaaaaaaa gataattgga ggcaaaaaaa gttgatattg    120

caacaataat aataataata tggaactgtt tgtgctttga tcctctgcag attgaaggtt    180

ctttcaagaa aaggaagcct ttggtaaata gtaaagaccc tttagtactt cgaagcactt    240

tcctttgtat ttccttgtta gaattgatga gctttttttt gatatattgg aagtaaaatc    300

tattagatat cttgttttaa tattttgtga tatgtaataa gtcgacttgt tggtgaacta    360

gtgtgg                                                               366


<210> SEQ ID NO 6
<211> LENGTH: 368
<212> TYPE: DNA
<213> ORGANISM: Glycine max

<400> SEQUENCE: 6

tcttaaccat gggctttttt gatcctttga aatattgctg ctcttcaatt caaggcatga     60

gctttaaact tttagttgtg aggtttataa tttctcaaac gatgatatgg taactttcca    120

agtacatgtc tacatggcac aatataaagt ttatgctggt gtgaatgagt ttgcacaagt    180

atagcaccca gaaatgagtt ttgaagtaga ttaatcaact tgatttctag agtaataaac    240

ttctaaaatt ctaggagctg gagtcgtgac attgacaacc atgttcaaga agtaataagt    300

tatagcctca aacagtaatg catagaggct agaaaggcct agagttgtta atcattgggt    360

tcggacta                                                             368


<210> SEQ ID NO 7
<211> LENGTH: 779
<212> TYPE: DNA
<213> ORGANISM: Glycine max

<400> SEQUENCE: 7

aaccacagaa aagaaacgaa atggtgagag ataaaattgg gaaggagata taccatcata     60

agttaacata ttcaaaataa gtaatcactg ctaagtttta taatgcaaaa gcaactatac    120
```

```
ctgaacactg catagggaat attactgtag tctggcttga ttgtttgccc accaaataca    180
gttttctgca aaacaaatat gttaaacaac aacaaataat atcatcatta gaccaatcaa    240
ctgcaaactc ctccctaccc agtacataaa taggtattct tatccactaa atatctgaat    300
acttacagca aagtacgatg cttccatcaa ggccaccgga gttagattca ttcggtttgt    360
gacatcaccc acagcccata tgctaggtat gcttgtgcgg gaatactcat ccacctaaac    420
acaaaggatc acagaacatt tagaactgag tcataatcat tctctagctc ttaaacaatt    480
gttcaaatca atatccagtc attgacgaaa gcatataaga tgatataacc taaaaaccaa    540
tttgcttcag acattgtatt cccactcact tgggaattga taagagaatg cttcattata    600
caaatatttt gcctaaaggt atgttgggaa taaaaaatat ttaatgtata gatttgattt    660
aggatttgat ttatagctat tggaaaaaac ccaagtccca cattggctag agataaggcc    720
aagatagaag atataagtgg gggacaacat ttatcctatg agttaccttt tgggcttga     779
```

<210> SEQ ID NO 8
<211> LENGTH: 903
<212> TYPE: DNA
<213> ORGANISM: Glycine max

<400> SEQUENCE: 8

```
tgacaaacca aggttattga acaaccaaca aataaactgt ctttttggta ctaataaatc     60
gttttctgct tcaatataag cagacaagca ggatgacatg tatgtatagt ttataacaaa    120
gcaacatcta gaaaagcaaa gacaaatcca aactatatct tcaaaaattc ttaaggaaga    180
gatacaaatc tgatttagat acaagaaaat caagaaataa caatgcttta cattattaaa    240
cataaaagaa tatcttgaac taccttcttt tgcaagagct tcttccaatt gaagtcaact    300
ttctcactca actcccaccc ataattcctg gcatcctgtc acaatcatgc ttttaatgga    360
tgatgatctc agaaacactt aaagaatatt acaataatta cgaaccagca tgaataaaaa    420
atacaaagaa aaaaccgata cattttctga tggaatataa aattaaatca catttgcata    480
acatatttta tgagaatgtg aaccaatcct actgtaacta catcacatca gatctgataa    540
catatacctt taataagtcc tagtagctta agatgagaca catgtcctga atttaatgta    600
gtacaggagc actgagataa gataagcttt aaaaacaaaa acacttctac gattagattt    660
ctttttaaa ctactatttc tagctttctg agaaacacta aaactgattt tttttttaaa    720
tttcttattt tccaaaattt atccaatcat cataaaaaat ttcaaagtta ttatttaaag    780
atttaattat tctgtgggtc cccacacttc taccaaattt caattaggtc cctgaacatt    840
ttttccttc aattgggtcg tcatgtctaa ttgtcattat gaaaaattaa ctgcaggcat    900
gca                                                                  903
```

<210> SEQ ID NO 9
<211> LENGTH: 829
<212> TYPE: DNA
<213> ORGANISM: Glycine max

<400> SEQUENCE: 9

```
gagtccaacg ttttgtgcgg ccatgcactc caactcccat aagaaggtcc ttgaaatgag     60
gaacaagaca ggcaccaaat ctggctttgc aactgtttct gctgcctcac cagaactcat    120
tccaaacact aacagcagcc ttacccttga atatatgtga aagggggaaa ggaaggattc    180
tagttggaga attctctaat tctctttcaa gtcttctctt gagtcatgtc ttatacaagg    240
ttttgaattg cattctacaa actgcaatgt taaaggtttt agaggtgtct gcaactgcgt    300
```

```
tgtggttgcg gttgtgactg catcagccat atttgtccac aattttgatg gcaaccgcaa    360

gttaaaacct tagtctttgt gttatttctt gtctgtcatt tatttttctc attggatttt    420

tgtacagggc tggaatgggg ggataggagc aaaatagaac atgatcatat tgtagctata    480

tttagaactg aagaacaagg gatagagata tgcaagtcaa agagggtaga gtcaccagag    540

tgttagccat tttaggtcta gtaattgtag cagtactcag gaggagtctt tgttactttt    600

cttattctca tcatttttca attttttttt ctttaatttc tgtttctaaa tatccctccc    660

tgtagcaaat tctttttgct gttcatttgt agcaaaactt atgagttgat caggaaagga    720

acttttggaa tttgccttct tccttttaat attttgtctt gtgcatatcc tttcctaata    780

tctgcaagct acaatgagta agtatatgcc agttatgatt ttgagcaat               829
```

<210> SEQ ID NO 10
<211> LENGTH: 399
<212> TYPE: DNA
<213> ORGANISM: Glycine max

<400> SEQUENCE: 10

```
tgacttgtaa ctcaggaaca gcagctcgtt acaactgatc tcacatcaat cattattcaa     60

ttgatctcta ccgcaggtag tctcctccct tctgctaggc ataaccttgt aaacactagt    120

tcattggttg gacagattga ccagcttcgt gggacgacca ttcctcctgg gaccggtgca    180

agtaacggct gtattcaacc acagaataat ggtggaaaaa tattgtctga tcagtccatg    240

cagactgatc tacctaatag tggtgaaatg gagcaaaagt acaatatggt agaacatgac    300

ttgaaagatg aagaagatgt agaggatgga gaaaaccttg cccctggttc atatgagatt    360

ctacaattag aaaaagaaga aatccttgct cctcatacc                           399
```

<210> SEQ ID NO 11
<211> LENGTH: 250
<212> TYPE: DNA
<213> ORGANISM: Glycine max

<400> SEQUENCE: 11

```
cttgttgatt cgggtgtgca taagggggcg ttggggctta tgctgaactc tgtcgttttg     60

gcattgatgt cgttgacggt ggaaccgttg ggtcgtttcg ttgggggagt taagtggcta    120

tggggaatcg taaacgtaat tctcgccgtt tgcatggcaa tgacggtggt tatcacaagg    180

gctgcagaac atgaacggaa aaacggcgtt tctgctgttg ggcatccctc agttggtgtg    240

caagtggctg                                                           250
```

<210> SEQ ID NO 12
<211> LENGTH: 405
<212> TYPE: DNA
<213> ORGANISM: Glycine max

<400> SEQUENCE: 12

```
ttgtgatctt cttcaacctt cagagtgaga aaacacattc agaaaccacg tttctctctt     60

cttcttcttc ttcttctttt tcttctctcg aggtcattat taagtattca ccatggaggc    120

accatctccc accaaaccca acgacccaac aaaaccttcc aacacttcca ccacccttag    180

tctggaggcc ggcccggccc aagcgagccc actccgaaaa atgtttgccg tggcgtccat    240

cgccgccggc atacagttcg ggtgggctct ccagctctct cttctaaccc cctacgttca    300

gcttttagga gtcccccacg cggcggcctc cttcatctgg ctctgcgggc ccatctccgg    360
```

gctcgtggta cagcccattg tgggctacta cagcgaccac tgtaa 405

<210> SEQ ID NO 13
<211> LENGTH: 760
<212> TYPE: DNA
<213> ORGANISM: Glycine max

<400> SEQUENCE: 13
gccttgggtt cttgatgttg ccaagaaatt tgggctactt ggtgctactt tcttcactca 60
gacatgcaca acaaacaaca tatacttcca tgtttataag aagttgatag agttgcctct 120
tacacaggca gaatatttgt tgccagggtt gccaaaactt gcagctgggg acttgccatc 180
tttcttgaac aaatatgggt cctatccagg ctactttgat gtagttgtga atcaatttgt 240
caacattgat aaagcagatt gggttcttgc aaacagtttt tatgaactgg agcaaggggt 300
aagtgacttg actagctgaa aattctcttc attaatttga tttgtactta tttgttggaa 360
tgaattagac agcagtagtt atctgggtaa aaagtttttc cttcaaattt tggtcaaaat 420
ttgtcctagt tcctattact tcaggatgat tctggtcttc ttttttattt ataattgatg 480
gattttgtct ctcatcctag tatcctaagt tccataaaaa gagaaaaaat tcatcaatta 540
taaaaagaat tcaaagacca aaaatatcat ttttaaagta taacgactaa gaacaatttt 600
gattgaaatt agagagatct agaatacatt tttatcctag ttattttgtt ggataatatt 660
gatgattgaa atttgaaatg aaatttattg taggttgtgg attggctggt gaagatttgg 720
ccattaaagc caataggacc atgcctgcca tctatctact 760

<210> SEQ ID NO 14
<211> LENGTH: 378
<212> TYPE: DNA
<213> ORGANISM: Glycine max

<400> SEQUENCE: 14
agatctaaca aggtaatttt tcccttaact atttgaaact cattatcaca acttggtaaa 60
agttaccttt caattgtcaa atttaaaacc catcacataa aatgccacaa atacatgcca 120
caccaaaatt tgcaagagaa ttcaaccaca ctgcagatct gcttcaggta gcagttcatc 180
gtgatacttt caccatactc aagcagaaag gtatatacaa agtactcatt tttttttgtt 240
aagaatgtga gggtaaagac caatttctga cccaatctgt aagagttgcc acatttctac 300
taacgtcttc tatattatca ctcttcattg caatcacttt ctcctccgag taactttctt 360
tagcctcctc aagcaaaa 378

<210> SEQ ID NO 15
<211> LENGTH: 707
<212> TYPE: DNA
<213> ORGANISM: Glycine max

<400> SEQUENCE: 15
caccttcgga gggaaattgt tctggataac tgtgagaatc ttcaagaaat aaaagggatt 60
ccatttggca ttcaatattt ttcggcaagg gattgtcatt cattgtcttc cgagtgcaga 120
agcatgttac tgagtcaggt tgctattttc tacatatttg acttgataat tgatatattt 180
tcacgttcat ccattctcta aatataacgt tgctaaatgt acgaatgaat tgtgataaac 240
aggaattgca tgagactggg ggatgtggag tgttttattt ggcaggaaca aggattccag 300
aatggtttca tcattgtatc aatggatcgt caatttcttt ctggtttcgt aacaatttcc 360
cttcaatatc tctgggtgtt gttgctggac ccaagagtta tttaaatgtg cattccagat 420

```
ttaggatcaa tatcaataac aatataacat ttaatttagg aataaggaat catttggttc    480

aagtacgtca tcatcgggtg gagctagcct cgatacctat agtttttttgg ggaaataaat    540

ggaatcgtgt ggaatgtact gtatacccac ttcaagagtt catcaaacaa attggaatcc    600

atgttttgga acaaggaaac aacatggagg acatccaatt taccaatccg ctgtcgtcct    660

caagggaaat gaacaaaaag aggaaaaaga ggggaaccca ggcgttc                  707


<210> SEQ ID NO 16
<211> LENGTH: 409
<212> TYPE: DNA
<213> ORGANISM: Glycine max

<400> SEQUENCE: 16

ccaagatggg aaagagttga gtttagaagt gtttccaaag gccattcttg tttgccatct     60

tgatcccagg cattatcatc atcttgacct gtattatctg tacatgagtc ctaataatgt    120

catccaagta tgcagtccta atctgtatat gctctgtgat ttcgatttgt tgttccaaaa    180

gcttgcattg ggtgtcgaga aggactggtt tcgcagatgc aggaaatggt caatgaattt    240

ctcgtttcga aaaaagtttc ctaagattgc ggtatgttgt tctataatat ctagattgaa    300

aagtgtcatg gaaatggtgt tgattttgaa gttcagcgta ctcatcaatg gcactatgca    360

atttagttct tcatgtaatt acatatttag aacatgggac ccgataatc                409


<210> SEQ ID NO 17
<211> LENGTH: 1154
<212> TYPE: DNA
<213> ORGANISM: Glycine max

<400> SEQUENCE: 17

tgattcgcca gcttgctgcc tgcgggcaca tttctccata tcagaccaca cctctctttt     60

ctgtaagcct cttattggtt ccctaacgaa tgttgttaat tacattgttg ttctgactat    120

ttattcagct tcggttgtag ccacggattc atgacagaga ttatcaactc atgcttagtt    180

cgaagactat tttaactgtt ttagttttga gttcagaata aagcacgcag cagaggtatc    240

tatctcctca gcttaaagct tttcaattca tcactttgaa tattattttt gttttttttag    300

tgagctataa cacaatcaga cttgaaaaat agtatcttat agaaaagtca attacaaatt    360

ttcttgtgaa atataaccac taaatcacat gaaaaaaata tgtaataatc gagaattaaa    420

aagttgagtt ttaggattta aggttttatc tccttttaga aataccagag ccatacaatt    480

ggtgtgcagt cttctccaat cttctatctt tattacattt ttattttgtt tttctaattc    540

tttttttaac tatttaatta gttagcttta ttttgttttt catttttttta attagttaca    600

tgacatatca caaataactt taaaattgct gactgatatg atcgaccaca tgatcacatt    660

taactgcaca agcaaattga gttaggaaaa gaattataat ctgatatttc taaaatttta    720

gaaattaaat gcaaagaata aaattcaaag gactacatat aaatttggtg tattttcaga    780

ataaaaaaac atatttaatc cctctatata ataatgaggt aggaacgggg aagaattttc    840

aaatattaat gtgaatacaa ttttctccta tagttcatta tatttcgacc gtcttaattt    900

gtccttactc ttgaaaactt attaagctga aatttttacc tatatctaaa tgcatggaca    960

acatggctac ttcacttcag aaatctcgaa gtgcaaccaa gaaattgctt gaagatttca   1020

caaagaaacg aagactagaa tcgccaaaag aacaagtcca aagtccaatg aaattaaaat   1080

ttattattgt attgtgtgcc tcaattagca cgtttgtatg tatgggagaa tgggagccaa   1140
```

```
cttggagcac aaga                                                    1154

<210> SEQ ID NO 18
<211> LENGTH: 328
<212> TYPE: DNA
<213> ORGANISM: Glycine max

<400> SEQUENCE: 18

tggcttgtgt agttattgtc ttcacccgca tgaggaagag aactagagat tttctgaaga    60

agcggggttg gtgaatgaac ttgtgtgtga tgcctctgtg gtagggtttt atgcatttct   120

ctatacactt tcaagatttg tttaaactga cataattttg ttgattactt atatcatcac   180

aaatgttata ggttaataat aagggatgcc acatttgatg atacatatag atgtttttgt   240

tcagcgagta taggctatct atctacatag atgatagatc tttttccttt tattgttgct   300

caaatatgtg atcattgatt ggagtgga                                      328

<210> SEQ ID NO 19
<211> LENGTH: 910
<212> TYPE: DNA
<213> ORGANISM: Glycine max

<400> SEQUENCE: 19

actaaaacta cctcaactgt tatagatgtg gtcatttcac ttaaatactg ctttagcaaa    60

tgtccatagc aattgttcag tgtcaatgct gctactgcac cagctattgt gttccatttc   120

ttcaaaattg gactataatt ttgtctctct ttcaatgcca aatattcagt ttcctgagct   180

aattgaagca taacttcacc tatttctttc tttgtttcag actcagcaga tttggcattt   240

gctgcttcca tcatctacag tcattaggca acaaagacat tatgatattt tctttttact   300

tttaaattaa aaagcagaaa atactataag tttgacacca ttagggatta aaaagcagaa   360

aatactacaa gcagaaaact ctacaagtta tatacatgct tctaacgtat caaccttttg   420

gattgtttct taacaaatac ctaccttttc aaaagcattt ttcaaggaag aacagatata   480

gtcatcaatc cggccctcag aggaattcgc tctagttttt tctccttttt cttgcctttc   540

ttcagaattt gtaacatctc ccaaaatctt ggatgctaat aacaccacag gggagaaggt   600

tttcaatttg tccaatatca ccctccctcg aaatacctct gggagttaaa gaaacctttt   660

atctgccccc ttcttggcgg gaactgagga cacatttcaa tatcttcaaa ataaccagga   720

ctccccttct ctttcttaaa ctcatttgcg ccctccattt ataatgtttg gaaggcaaaa   780

aagggaggtt taatttccca tttctcattt gtggaacatc ccctgaaaac acttgtgtgg   840

gctttttcca cggggccttt ttttaaaaga atgtcctttt taaaaaagta tcactctcaa   900

acatgcggga                                                          910

<210> SEQ ID NO 20
<211> LENGTH: 378
<212> TYPE: DNA
<213> ORGANISM: Glycine max

<400> SEQUENCE: 20

gatatgtaaa ggtggaagac ttaagaatgc gcaagagctt tttcaacatc tcttggttaa    60

aggctgttgt atagatgtct ggacatatac tgtcatgatc agtgggcttt gtaaagaggg   120

catgtttgat gaagctttgg ccattaagtc aaaaatggaa gacaatggtt gcatccctaa   180

tgctgtaact tttgaaatca ttattcgttc tctttttgag aaggatgaaa atgataaggc   240

cgagaaactt ctccatgaaa tgattgctaa aggcctatta ggttttagga attttcatgg   300
```

```
ggagtgatct ccagatacaa attaagttat tgttaatttt catggtgagc gaccaatgtt    360

tattgcgttt gattgttt                                                  378


<210> SEQ ID NO 21
<211> LENGTH: 403
<212> TYPE: DNA
<213> ORGANISM: Glycine max

<400> SEQUENCE: 21

atgcagacta gttctgtcta ttggtttatt aattgggaat tcttaactca ccagcctttg     60

caacagctac aaaagaagct aacaaccttc ggaattccgt atctgggttt gctcattgga    120

tcctgcaaga aacgacagga ggatggaacc aattctgtta accttttact atgcttacgt    180

caaccgagtg attggtttgg ggtcttaagt ggtttttgta aagttttcta ttcattagct    240

ttaaagcatt ttattttgta ccttaaattg ttttacccct tcgccccttc acccaaaaga    300

ctaattttta aaatgtaggg gttaattcta tctgaagttt cgtacgtaaa tctgttcttc    360

tgcagatttt ctctaatggc aatctacagc ttccgtctta ctt                      403


<210> SEQ ID NO 22
<211> LENGTH: 766
<212> TYPE: DNA
<213> ORGANISM: Glycine max

<400> SEQUENCE: 22

attgcactcc gtgtagttgg gtccagaaga agcatttaca gaaacttcca tgtattggct     60

ataggcatgt agagcaacgt tgttcatcgc ttcaaatttt ttaatgtagg cttttggtat    120

tgggccgctg aagttgttgg aagagacatc aaaaatgact aaactgggga atccatgctt    180

gatctttaaa ccggcaatgg gaccgtacaa cttgttggct cgcaaaacca atactttcaa    240

ttctggtaga gtttgaagcc aatggggaaa cacatccttt atttgattgt ttccaagatc    300

taaaacctcc agatgaatgc aattggacaa agattctggc aaaaaacctt ctaatagttg    360

gttgccattg agatccagag ttctgagctg acagtccttt gaaaagatac ttggcaaagt    420

gccatgaagc ttgttcagtt gtagatccaa aactagaagg gatgatgagt ttgcaaggca    480

ttgtggaatg gttcctgtca acttgttgtg agacaagttg agaatctcaa ttgcacttgc    540

attgcaaatt gaggaagaga agtcaccagt gattgagtta aaactaagat caaggtaacc    600

gagttgttgg ttccatgaga attggtgcaa tgattgtgtc aataggttat gagagaggtc    660

caattcagat aacgatattt catgcaacca atttggcact ctacctttaa agttgttatt    720

ggacaaatag agcgattttc agattgggga ctttttcccc ataatt                   766


<210> SEQ ID NO 23
<211> LENGTH: 864
<212> TYPE: DNA
<213> ORGANISM: Glycine max

<400> SEQUENCE: 23

ttgttttctt ctctgtattt acaatagggg aaagatgcat gaagcaatac gtcttgtgtt     60

gtcttagtga gatgctttgt ctcatggaca aaggagttat aaagctttat aatctgacag    120

ttttttcttt tttcttaccg aactgtctgt ctgctcaaga tggtgcatgc ttagttttgg    180

tttatggaat tcaggaagat aaggaagtat cttgaatttg agcttttaat caatttctat    240

atgcatattg tgatggtagt tttcatttaa aacaaaaatt gtgtttgtca gttggggtta    300
```

```
caatcactgg atcgcatcat ttttatgttg gatggcattc gtgtcaatat attttatctg    360

gttctgtgct aagctaccat ggaggagttt atgtcttgtt ttggtgaaat ttcttctctt    420

tgattaaaag tgaagttaaa ctggaaaaaa atgagattta attaatgaac gagtgacaaa    480

tggtatgggt ttggtttttg gtttgtttat attggtttaa catgggatgt tgcgatgata    540

tagaggggtc catgctatgt tctgtatgat accaataagc ttgtggtaga gtaaactcca    600

aaaggatgaa gaaaaaagtt agcataaggc atagagtgca ttattatgtt aaagaatgag    660

aaattgcaat ggcttagagt gcattattat taactatatg ctggaatata tatgataagg    720

ctccattggt ttatgagaaa ctacgggtgg agattttccc ccctattaaa tagtaacaaa    780

tttggaagat taaatacaca aatgttcact tctcttgtgt atgttggtct ctcagtgctt    840

gcatatggta gtaatctgca ttat                                            864
```

<210> SEQ ID NO 24
<211> LENGTH: 1068
<212> TYPE: DNA
<213> ORGANISM: Glycine max

<400> SEQUENCE: 24

```
cccaggcatt aaccagggag atggcacaaa gttgaacaat cacattaaaa ttattatttt     60

aaccagctcc accaatgaac catactatca aggctctatc agtttgcttc caaagtcggg    120

cttccttaca caaacagaca agacaatgct tacataagac agacaaaact gctcatttac    180

actgtttgga agggatgaat atgggaggga agaaacacag ataacaatgt catttccttt    240

gtttggttgg agaggaagtg gaaagaaaat gagaagaaaa gttgacttct agagataaaa    300

attcaaactt ttttgtactt tctctccaat ttcaatttca aacttttctc tcctccctca    360

ctttctttcc tctcgaccaa acatagggct aaagttgcac aattcaaaaa attacactct    420

cccaaagcaa ctttgacaaa ctcaaccaat agctttgacc taactaagag acacaagctt    480

gttcacacat ctctccccca ctagaaaaga caaaactcta cagaaaaagc caaaaaccag    540

ctgcagctta atttcattta gcattgtgct tttggatcca ctataggcta ctcggatcca    600

atggttgttt caatggaatt gtgacttccc tctcttcttt gtaataaata aatctttttt    660

tgtcatcaaa tatatgtaaa acttatcctt gttaaatata accacaactt cctaataata    720

tactaccaat ttttttaat caataacaag aaaaaaatgt ctaaccatta gtcatttgct    780

atgcaagtga aaacatcctt tggaacccat gttatccgaa gtgacacgat gatttgagtc    840

tcatatgtga gaatcaatat ttaacattta attttagtag ataaataaac cccaaaagat    900

aggaggtaga aaccatgctc agatgtgtat aaagaaggtt gtaccttttg ggactttttc    960

tttttccctt catcagcttc ttcactctct tcactttcaa catatgatac cttcctgact   1020

gtcctactag aagtgcgaat ctcactgttg cgcgaagaaa aacctgtg                1068
```

<210> SEQ ID NO 25
<211> LENGTH: 321
<212> TYPE: DNA
<213> ORGANISM: Glycine max

<400> SEQUENCE: 25

```
cttttctatt cttcaagact acatccatct gcaataataa agcttgcccc acaacattat     60

gttagaaacc taaacatctc tagtagaggc aatggagatg agaagataaa tgattcaaag    120

agaaaaaagt agagcaggtt ttatcagtaa attagcaaac aaagagacca ttacaatgac    180

aatgaaggtg acattatctg cataaaaatt atccttccca aattcagaat tccttgtccc    240
```

taataagatt atcaagtaac aaccataaaa ctgtttccct tcagccctta tcaaagtctg 300
ctcatatatt ctgcaactgg g 321

<210> SEQ ID NO 26
<211> LENGTH: 370
<212> TYPE: DNA
<213> ORGANISM: Glycine max

<400> SEQUENCE: 26
acagatcatt cttcagtttg gcaaggttgg caaggatata tttactatgg actatagata 60
tcccctatct gcttttcagg cttttgccat ttgcttgact agttttgaca caaaactggc 120
ttgtgaatag tgacaatgag aggtatggta caaagacaat agcattctat ctccatttat 180
gtattcactg cgaggtgaag ctgcatggag tcattttaca ccaaatggtt taactgtaaa 240
ggacagaaca acctttgctc aatatgtttt ttcttatatc cttttccttt tatgttagtc 300
ttcaacaaac tatctgtcaa acatgtgttg cttacccgca gtgtaattgg cttcttccaa 360
tggtaggctc 370

<210> SEQ ID NO 27
<211> LENGTH: 716
<212> TYPE: DNA
<213> ORGANISM: Glycine max

<400> SEQUENCE: 27
cttttccttc gctgattgaa gattctccca gagcaatcta cagagtaata taaaccatag 60
ttaattaaaa caaccatttg taggactaaa agtagccaac aaagactcaa aataaaccag 120
caaagtgata ttttgtgttt tacatcagca caaccaattt tcctaaagtc tgtttggata 180
atcttctcag taaacactta aaggaaaaga aaataacaaa gtaaaataaa ttaaatgtat 240
cccataaaat taaaattatc tcattcataa gttcaaatta gcttttgaag aagctaaatg 300
agagaatttc tataaattgg tttctacata agctaatttt ccttgtataa gatcacaagt 360
atcctgcatt gaagataatc ctactcaagc caagtagaac cactaaggac agaaaaactc 420
tccatatatt taacacaact acttacgaag gacttgaaca tgagaccact actagttagg 480
ccaaacaacc catgtcagtt gttccatgcc tcactggtgt ataagctaac tttaacttac 540
aagtgaaact tatttaattt tacatttttt cttcttcttg taagtgttta tacagaagtt 600
catctaaaca gggcttaact aacaaacacc aaggagatat aaggttgggt gggtggttaa 660
gaaagaaggg aaatcccatc aacaaaaaac taacgattaa catttcccga taaaaa 716

<210> SEQ ID NO 28
<211> LENGTH: 396
<212> TYPE: DNA
<213> ORGANISM: Glycine max

<400> SEQUENCE: 28
tctcaatcct ctctccaatt cctaagtggg tcccaaccca attcggattt cgtttctggg 60
tttccccaat tcgaagctct gcactttccc ctttgaagtg gaattttttt tcgttcctgt 120
gaagttccat tccatattct gggaatgggt ctataaaaca agcttccaaa ttggagagaa 180
agtcccaaac ttttcggttc aattttgagt tttcgcaatt gggtctgtga tcttcttgtg 240
tgggtgagca aggtttgaaa aaactttctg tgatcgtgat tttggcccca acttcaattg 300
tggctgcatc cgctgtaatt tgttcacaat tttccgcaat atcaaaggat cgtgacgacg 360

```
aaaccacaac tgcaaccgca atttaaacct agtgtg                               396


<210> SEQ ID NO 29
<211> LENGTH: 366
<212> TYPE: DNA
<213> ORGANISM: Glycine max

<400> SEQUENCE: 29

gaggttcttg gaggccatag agaagagaga acaagagcgt gtggtgagag aggaagcgtg      60

gagaatgcaa gagatgcaaa ggatcaacag ggaaagagag attctagcac aagagaggtc     120

cattgccgca gcaaaagatg ctgctgttat gacatttttg caaaagatag ccgaacatca     180

gcaacaagaa actatcaatc ttgaaccagc attgaataac aacagcatca ctgttgttcc     240

acagcaacca gtgccacaag caacaccaac atcaactcca acaccacaac aagcacaaac     300

aacaacagtt cctgaggccc cacaagtgca gccattggtc ccacaactac aacaacaaca     360

acaaca                                                                366


<210> SEQ ID NO 30
<211> LENGTH: 744
<212> TYPE: DNA
<213> ORGANISM: Glycine max

<400> SEQUENCE: 30

ctaagtacga aaatcgttat ccgccgcaac agccactaag atgttctttg agtcttggca      60

cgccacgtgt cagaactgcc aacagatagc cccatctctt tctccttctc cctaaacctc     120

gaactcagca cccccatcca ctggtccctc cccactccat catttattat actttcttct     180

tcttctttat tattgttgat taatataaca tacacccaca tatttcatat gggtacttgt     240

taatttgggt gtggattgtt agtttgttac ttgttttgtt ccgttcaggt gattgtttga     300

ttgagccttg aagaaatgga ccacagcgct gatgcacatc gcacggactt gatgaccata     360

acgcggttcg tgctgaacga gcaatccaag caccccgagt cacgcggcga tttcaccatc     420

ttgctcagtc acattgttct cggttgcaag ttcgtttgtt ccgctgtcag caaggtaagc     480

tatccctact ttgtgtgttt tttatcgaca aatattaatt gttagtatta ttaatccttt     540

ttcttttctt ctcttttcgt cattagacta atcttatatc tcgttatcat gtatttattt     600

cactctattc aaatatatta ttctggtctt aaatataaga agaagaaaaa aaaatgattc     660

atgctgacta agaatgaaat attgattaga gttatgtgtt gtgacctgtg caggctggtc     720

ttgctaaact tattggactc gctg                                            744


<210> SEQ ID NO 31
<211> LENGTH: 679
<212> TYPE: DNA
<213> ORGANISM: Glycine max

<400> SEQUENCE: 31

ataatttgat catcatattc ctaaactttt atgcttaagc agagacaagc tgctcaatgt      60

gtgggtcgtg taatccgttc aaaggctgat tatggaatga tgatttttgc agacaaaagg     120

ttagtatcct tgagtccttt tgcttccatg aacatgttga acatttggga aaatgtgagg     180

gttgcttata gtattctacg ctgacgttaa tttgatgaag ccaacttgct agtttctagt     240

tttgattcaa aaagcacaat gcactcttct ctttgtaact ttatggaatt tgtcctgaaa     300

tggattggaa gttattggtt gtctctaata atgaatgaca aaccaaaaga aacttgacaa     360

tcttcagaat ccagtttgtc aagcaaagaa agaaatatgt ttgttcaggt ccatgacatg     420
```

```
tttagtttca aaaaccaatg taactaacag atataatcag caaaaattgg taaatgtctc    480

tgtaaatatc aataattaca gtcacaaatt ctatacatta tataggaaat aaccaattta    540

aacttatgaa agtctgcatg aataaatggc ctattttacc tatgatgatt gctccattta    600

tggttttggc ttctactttt ctctatgaca gtgttctgac agtaaatagt aatacattgt    660

tggttataac ttctgcact                                                 679


<210> SEQ ID NO 32
<211> LENGTH: 770
<212> TYPE: DNA
<213> ORGANISM: Glycine max

<400> SEQUENCE: 32

taatgaacaa attcatattt gaaaatattt tgatactgaa attatgtctt ctattttgat     60

tagttagcat tgagaaaacc atcaaattta actaaataat gctcattgtc cttcagcttt    120

tatctttagg caacttttta ataatttctt aatagaattc aaaatattca tggttggaga    180

gtaaataagg tatttgtttt ggaaactaga gatactactt ttccactgca aaagaagtga    240

tgcgcgtgaa tggcacaaca aaatcctttg tagctaatca tatagctgaa actactgctg    300

gagttgtgac aataagagcc tttgaagaag aagatcgttt ctttgagaag aatcttgatc    360

taattgacag caatgctagt cctttcttcc atagttttag ctcaaatgag tggctgatcc    420

aaagattaga aatagttagt gcagtactgc tttcctccgc agcgctatgc atggttatgc    480

ttccaccaga gactttcagc tctggtaaga ctttggtcat tgtttcatgt aaaatgccat    540

gcctttgagt attacaatga tcttcatatt ctattctttt tatcctcaaa aagtaacatt    600

atctcttttg atgcaagttt cttaatttca gtaatattct tttcaggatt tcttggcttg    660

tctctctctt atggctttac actaaatgct tccttacaat ttttaattca aagccaatgc    720

agtctagaaa attacataat atctgtagag aggctaaatc attatatgca                770


<210> SEQ ID NO 33
<211> LENGTH: 779
<212> TYPE: DNA
<213> ORGANISM: Glycine max

<400> SEQUENCE: 33

tagccttctt gtccactttt ggcaacggcc aaactccaca actcaacctt gcaggtcatt     60

gtgaccccaa caacaatggc tgcactgggt tgagcagtga catcaaaact tgccaagacc    120

ttggcatcaa agtgttgctc tcccttggtg gtggtgctgg aagctactcc ctcagctcag    180

ctgatgatgc cactcaactt gcaaactacc tctggcagaa tttccttgga ggtcaaaccg    240

gtaagagtaa caatacacaa atatctatag attcttcctc aaatatactt tttattatta    300

aatgaaattt attaaaaatg actgaatctt gtattaaata ttggaaagag gggttaacaa    360

gattttgtaa tttttcataa atttcaacaa taataaagtg ttttagaaag agtatattaa    420

atagggtgct gctaataata tcttgtgtgt taaacactac tatcaaatat taatatatgt    480

tatttttctt tattagtttt ttcacaccaa attatactat atctatcgta tgcatatttt    540

tctttccttt cttttcctct ctgagtgttg aataacatat atatattagt gtctactaat    600

ctttttccat ctggtaattc aggatcaggg ccattaggta atgttatatt ggatggcatt    660

gactttgaca ttgaatctgg tgggagtgac cattatgatg acctagctag ggcattaaat    720

agcttcagct cacaaaggaa ggtgtacttg tctgcagccc cacagtgcat aatccctga      779
```

<210> SEQ ID NO 34
<211> LENGTH: 533
<212> TYPE: DNA
<213> ORGANISM: Glycine max

<400> SEQUENCE: 34
attgaaaatg agaccagtat tcattgacaa gctgattgaa tagcgatcct tctttcttca 60
tcaggcacat tggatcatca tactccacca attttcctgt caatacaagt atccctttga 120
agaaaacaag taatagtaaa aaaatattct tcacctttat tctaatgaaa attcaacagt 180
gaaaatcaag tacccaatat tttacaagtt atcactaaat caactaattg tctattataa 240
taccctttaa ccaggtgaat gcaattaaat cctctgctaa acaacataac atgcctatct 300
atggggtgtg tcaaacccag tggtataggt agaatagttt aacataacca taagaaaatg 360
gaattagagc tatgaattag cccgaaaaag gtttgttgaa tgacataaag gagtcggaaa 420
tatgcatttt taccatctct gattgaaaga accatagtgc aatccatcac ggttggtatc 480
ctgtgtgcta ctgtgatcac tgtacaatct gcaaactcag tcctaatggt ctt 533

<210> SEQ ID NO 35
<211> LENGTH: 316
<212> TYPE: DNA
<213> ORGANISM: Glycine max

<400> SEQUENCE: 35
tggaggagtt gaggaagagg gctgaagctg acaagaatga taagtctgtg aaggaccttg 60
tgttgcttct ctttgagact gccctttgga cttcaggttt cagccttgat gatcccaaca 120
catttgcttc gaggattcac aggatgttga agttgggtct tagcattgat gaggatgaca 180
atggtggaga cgatgttgat atgcccccat tggaagagga cggtgctgag gagagcaaga 240
tggaggaagt ggactaaatg ccaaaggtct cgtgttaaat gaattgtggt tcgtgtctgt 300
taaatggtgg tggatg 316

<210> SEQ ID NO 36
<211> LENGTH: 350
<212> TYPE: DNA
<213> ORGANISM: Glycine max

<400> SEQUENCE: 36
ctattcgtca catcgtatat atgcagtacc acatccgtca tctttccctt tcacccacca 60
agacccaaac tttaaacaac ctcacttcac ctttctctct ctaaacgcta ttttcctatc 120
cgggtctctc tctttctctc tctatatgat ttgattcagc ttgaagattc aacaacgggt 180
gttgttgttc ctctctcttc tcttttcgta aattgaacca agattcggcc ttgggatccc 240
ggaaaacctt ccaatttcac cgtccaagtt tttttctcgc cggaatcgaa agattttcgt 300
gtttctctcg tgaatttata ttctaggagg agggaacata acgaggagag 350

<210> SEQ ID NO 37
<211> LENGTH: 410
<212> TYPE: DNA
<213> ORGANISM: Glycine max

<400> SEQUENCE: 37
cactggaagc aaatgctcac tggttgctaa aagaggagct tatgtttgta tgtagaattt 60
tcaagatgca gcatcagtgc atgctaagta gggagcttgg atttctctct ggtacctaag 120
atatgagaat gataggatta atgttaatat taactcaagg aatgacttct tctaatcata 180

```
tgtatgcagt tccttcagtt aaagaattta tgcaatgaca actgtttctt ttagaacatc    240

atatagatgc caaaaaaaaa gtgaaattgg tacaaaattt agcttctaga ctatttttg    300

ggaggtgatg ttgctgtaca gaatatggga gactgtattg tgattctgca tttattgatg    360

aaaagccaag gatttgtgga acccatatat ctcttgattg catggtcaga               410


<210> SEQ ID NO 38
<211> LENGTH: 28
<212> TYPE: DNA
<213> ORGANISM: Artificial Sequence
<220> FEATURE:
<223> OTHER INFORMATION: Synthetic

<400> SEQUENCE: 38

ttcatcttaa acttcattgc gttatttt                                        28


<210> SEQ ID NO 39
<211> LENGTH: 25
<212> TYPE: DNA
<213> ORGANISM: Artificial Sequence
<220> FEATURE:
<223> OTHER INFORMATION: Synthetic

<400> SEQUENCE: 39

ccaaagtcaa acaagaatcc aaact                                           25


<210> SEQ ID NO 40
<211> LENGTH: 26
<212> TYPE: DNA
<213> ORGANISM: Artificial Sequence
<220> FEATURE:
<223> OTHER INFORMATION: Synthetic

<400> SEQUENCE: 40

cacttgtggg taaaaaggac ttgtac                                          26


<210> SEQ ID NO 41
<211> LENGTH: 30
<212> TYPE: DNA
<213> ORGANISM: Artificial Sequence
<220> FEATURE:
<223> OTHER INFORMATION: Synthetic

<400> SEQUENCE: 41

tgcacatact tgcaaataaa catattaaac                                      30


<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42

ggacatgaga agtatgcttt ttgc                                            24


<210> SEQ ID NO 43
<211> LENGTH: 29
<212> TYPE: DNA
<213> ORGANISM: Artificial Sequence
<220> FEATURE:
<223> OTHER INFORMATION: Synthetic

<400> SEQUENCE: 43
```

tgatatcatt gctctctctt ttgttagaa 29

<210> SEQ ID NO 44
<211> LENGTH: 26
<212> TYPE: DNA
<213> ORGANISM: Artificial Sequence
<220> FEATURE:
<223> OTHER INFORMATION: Synthetic

<400> SEQUENCE: 44
tcaagcatat cacatctcac acatgt 26

<210> SEQ ID NO 45
<211> LENGTH: 27
<212> TYPE: DNA
<213> ORGANISM: Artificial Sequence
<220> FEATURE:
<223> OTHER INFORMATION: Synthetic

<400> SEQUENCE: 45
atctaatcat ttcatatgag cgtgaca 27

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
tgtgcgggaa tactcatcca 20

<210> SEQ ID NO 47
<211> LENGTH: 29
<212> TYPE: DNA
<213> ORGANISM: Artificial Sequence
<220> FEATURE:
<223> OTHER INFORMATION: Synthetic

<400> SEQUENCE: 47
tgatttgaac aattgtttaa gagctagag 29

<210> SEQ ID NO 48
<211> LENGTH: 32
<212> TYPE: DNA
<213> ORGANISM: Artificial Sequence
<220> FEATURE:
<223> OTHER INFORMATION: Synthetic

<400> SEQUENCE: 48
acgaaccagc atgaataaaa aatacaaaga aa 32

<210> SEQ ID NO 49
<211> LENGTH: 28
<212> TYPE: DNA
<213> ORGANISM: Artificial Sequence
<220> FEATURE:
<223> OTHER INFORMATION: Synthetic

<400> SEQUENCE: 49
gttacagtag gattggttca cattctca 28

<210> SEQ ID NO 50
<211> LENGTH: 27
<212> TYPE: DNA
<213> ORGANISM: Artificial Sequence
<220> FEATURE:
<223> OTHER INFORMATION: Synthetic

<400> SEQUENCE: 50
aaaggaagga ttctagttgg agaattc 27

<210> SEQ ID NO 51
<211> LENGTH: 27
<212> TYPE: DNA
<213> ORGANISM: Artificial Sequence
<220> FEATURE:
<223> OTHER INFORMATION: Synthetic

<400> SEQUENCE: 51
gcaattcaaa accttgtata agacatg 27

<210> SEQ ID NO 52
<211> LENGTH: 28
<212> TYPE: DNA
<213> ORGANISM: Artificial Sequence
<220> FEATURE:
<223> OTHER INFORMATION: Synthetic

<400> SEQUENCE: 52
tggataactg tgagaatctt caagaaat 28

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gacaatccct tgccgaaaaa 20

<210> SEQ ID NO 54
<211> LENGTH: 25
<212> TYPE: DNA
<213> ORGANISM: Artificial Sequence
<220> FEATURE:
<223> OTHER INFORMATION: Synthetic

<400> SEQUENCE: 54
cgaccgtctt aatttgtcct tactc 25

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
catgttgtcc atgcatttag atatagg 27

<210> SEQ ID NO 56
<211> LENGTH: 25
<212> TYPE: DNA
<213> ORGANISM: Artificial Sequence
<220> FEATURE:
<223> OTHER INFORMATION: Synthetic

<400> SEQUENCE: 56
caccattagg gattaaaaag cagaa 25

<210> SEQ ID NO 57
<211> LENGTH: 25
<212> TYPE: DNA
<213> ORGANISM: Artificial Sequence
<220> FEATURE:
<223> OTHER INFORMATION: Synthetic

<400> SEQUENCE: 57
ccaaaaggtt gatacgttag aagca 25

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
ggtattgggc cgctgaagtt 20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
ggttttgcga gccaacaagt 20

<210> SEQ ID NO 60
<211> LENGTH: 26
<212> TYPE: DNA
<213> ORGANISM: Artificial Sequence
<220> FEATURE:
<223> OTHER INFORMATION: Synthetic

<400> SEQUENCE: 60
caaaaggatg aagaaaaaag ttagca 26

<210> SEQ ID NO 61
<211> LENGTH: 25
<212> TYPE: DNA
<213> ORGANISM: Artificial Sequence
<220> FEATURE:
<223> OTHER INFORMATION: Synthetic

<400> SEQUENCE: 61
gccattgcaa tttctcattc tttaa 25

<210> SEQ ID NO 62
<211> LENGTH: 24
<212> TYPE: DNA
<213> ORGANISM: Artificial Sequence
<220> FEATURE:
<223> OTHER INFORMATION: Synthetic

<400> SEQUENCE: 62
aaggctctat cagtttgctt ccaa 24

<210> SEQ ID NO 63
<211> LENGTH: 28
<212> TYPE: DNA
<213> ORGANISM: Artificial Sequence
<220> FEATURE:
<223> OTHER INFORMATION: Synthetic

<400> SEQUENCE: 63
cttatgtaag cattgtcttg tctgtttg 28

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
ggttagtatc cttgagtcct tttgctt 27

<210> SEQ ID NO 65
<211> LENGTH: 21
<212> TYPE: DNA
<213> ORGANISM: Artificial Sequence
<220> FEATURE:
<223> OTHER INFORMATION: Synthetic

<400> SEQUENCE: 65
caaccctcac attttcccaa a 21

<210> SEQ ID NO 66
<211> LENGTH: 27
<212> TYPE: DNA
<213> ORGANISM: Artificial Sequence
<220> FEATURE:
<223> OTHER INFORMATION: Synthetic

<400> SEQUENCE: 66
tggctgatcc aaagattaga aatagtt 27

<210> SEQ ID NO 67
<211> LENGTH: 22
<212> TYPE: DNA
<213> ORGANISM: Artificial Sequence
<220> FEATURE:
<223> OTHER INFORMATION: Synthetic

<400> SEQUENCE: 67
ctgaaagtct ctggtggaag ca 22

<210> SEQ ID NO 68
<211> LENGTH: 24
<212> TYPE: DNA
<213> ORGANISM: Artificial Sequence
<220> FEATURE:
<223> OTHER INFORMATION: Synthetic

<400> SEQUENCE: 68
accaggtgaa tgcaattaaa tcct 24

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
ggtttgacac accccataga tagg 24

<210> SEQ ID NO 70

<211> LENGTH: 13
<212> TYPE: DNA
<213> ORGANISM: Artificial Sequence
<220> FEATURE:
<223> OTHER INFORMATION: Synthetic

<400> SEQUENCE: 70
catccaaaaa tgc 13

<210> SEQ ID NO 71
<211> LENGTH: 13
<212> TYPE: DNA
<213> ORGANISM: Artificial Sequence
<220> FEATURE:
<223> OTHER INFORMATION: Synthetic

<400> SEQUENCE: 71
catcccaaaa tgc 13

<210> SEQ ID NO 72
<211> LENGTH: 18
<212> TYPE: DNA
<213> ORGANISM: Artificial Sequence
<220> FEATURE:
<223> OTHER INFORMATION: Synthetic

<400> SEQUENCE: 72
ttgtttaaga tcaaaatt 18

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
ttgtttaaaa tcaaaattag 20

<210> SEQ ID NO 74
<211> LENGTH: 15
<212> TYPE: DNA
<213> ORGANISM: Artificial Sequence
<220> FEATURE:
<223> OTHER INFORMATION: Synthetic

<400> SEQUENCE: 74
ccaagtacat ttctg 15

<210> SEQ ID NO 75
<211> LENGTH: 16
<212> TYPE: DNA
<213> ORGANISM: Artificial Sequence
<220> FEATURE:
<223> OTHER INFORMATION: Synthetic

<400> SEQUENCE: 75
tccaagtaga tttctg 16

<210> SEQ ID NO 76
<211> LENGTH: 18
<212> TYPE: DNA
<213> ORGANISM: Artificial Sequence
<220> FEATURE:
<223> OTHER INFORMATION: Synthetic

<400> SEQUENCE: 76
ttgctttaat atttttcc 18

<210> SEQ ID NO 77
<211> LENGTH: 21
<212> TYPE: DNA
<213> ORGANISM: Artificial Sequence
<220> FEATURE:
<223> OTHER INFORMATION: Synthetic

<400> SEQUENCE: 77
agataaattg ctttaatata c 21

<210> SEQ ID NO 78
<211> LENGTH: 15
<212> TYPE: DNA
<213> ORGANISM: Artificial Sequence
<220> FEATURE:
<223> OTHER INFORMATION: Synthetic

<400> SEQUENCE: 78
aggatcacag aacat 15

<210> SEQ ID NO 79
<211> LENGTH: 16
<212> TYPE: DNA
<213> ORGANISM: Artificial Sequence
<220> FEATURE:
<223> OTHER INFORMATION: Synthetic

<400> SEQUENCE: 79
aaaggatcgc agaaca 16

<210> SEQ ID NO 80
<211> LENGTH: 21
<212> TYPE: DNA
<213> ORGANISM: Artificial Sequence
<220> FEATURE:
<223> OTHER INFORMATION: Synthetic

<400> SEQUENCE: 80
ctgatggaat ataaaattaa a 21

<210> SEQ ID NO 81
<211> LENGTH: 22
<212> TYPE: DNA
<213> ORGANISM: Artificial Sequence
<220> FEATURE:
<223> OTHER INFORMATION: Synthetic

<400> SEQUENCE: 81
tctgatggaa tataatatta aa 22

<210> SEQ ID NO 82
<211> LENGTH: 16
<212> TYPE: DNA
<213> ORGANISM: Artificial Sequence
<220> FEATURE:
<223> OTHER INFORMATION: Synthetic

<400> SEQUENCE: 82
ctcaagagag gacttg 16

<210> SEQ ID NO 83
<211> LENGTH: 18
<212> TYPE: DNA

<213> ORGANISM: Artificial Sequence
<220> FEATURE:
<223> OTHER INFORMATION: Synthetic

<400> SEQUENCE: 83
aagagaagac ttgaaaga 18

<210> SEQ ID NO 84
<211> LENGTH: 14
<212> TYPE: DNA
<213> ORGANISM: Artificial Sequence
<220> FEATURE:
<223> OTHER INFORMATION: Synthetic

<400> SEQUENCE: 84
ccattcggca ttca 14

<210> SEQ ID NO 85
<211> LENGTH: 16
<212> TYPE: DNA
<213> ORGANISM: Artificial Sequence
<220> FEATURE:
<223> OTHER INFORMATION: Synthetic

<400> SEQUENCE: 85
ttccatttgg cattca 16

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
tttcagctta ataagttttc 20

<210> SEQ ID NO 87
<211> LENGTH: 16
<212> TYPE: DNA
<213> ORGANISM: Artificial Sequence
<220> FEATURE:
<223> OTHER INFORMATION: Synthetic

<400> SEQUENCE: 87
ttcagcgtaa taagtt 16

<210> SEQ ID NO 88
<211> LENGTH: 17
<212> TYPE: DNA
<213> ORGANISM: Artificial Sequence
<220> FEATURE:
<223> OTHER INFORMATION: Synthetic

<400> SEQUENCE: 88
cttgtagtgt tttctgc 17

<210> SEQ ID NO 89
<211> LENGTH: 17
<212> TYPE: DNA
<213> ORGANISM: Artificial Sequence
<220> FEATURE:
<223> OTHER INFORMATION: Synthetic

<400> SEQUENCE: 89
acttgtagag ttttctg 17

<210> SEQ ID NO 90
<211> LENGTH: 15
<212> TYPE: DNA
<213> ORGANISM: Artificial Sequence
<220> FEATURE:
<223> OTHER INFORMATION: Synthetic

<400> SEQUENCE: 90
ccattgtcgg tttaa 15

<210> SEQ ID NO 91
<211> LENGTH: 14
<212> TYPE: DNA
<213> ORGANISM: Artificial Sequence
<220> FEATURE:
<223> OTHER INFORMATION: Synthetic

<400> SEQUENCE: 91
cattgccggt ttaa 14

<210> SEQ ID NO 92
<211> LENGTH: 17
<212> TYPE: DNA
<213> ORGANISM: Artificial Sequence
<220> FEATURE:
<223> OTHER INFORMATION: Synthetic

<400> SEQUENCE: 92
aggcatagag tgaatta 17

<210> SEQ ID NO 93
<211> LENGTH: 17
<212> TYPE: DNA
<213> ORGANISM: Artificial Sequence
<220> FEATURE:
<223> OTHER INFORMATION: Synthetic

<400> SEQUENCE: 93
aggcatagag tgcatta 17

<210> SEQ ID NO 94
<211> LENGTH: 14
<212> TYPE: DNA
<213> ORGANISM: Artificial Sequence
<220> FEATURE:
<223> OTHER INFORMATION: Synthetic

<400> SEQUENCE: 94
cgggctacct taca 14

<210> SEQ ID NO 95
<211> LENGTH: 14
<212> TYPE: DNA
<213> ORGANISM: Artificial Sequence
<220> FEATURE:
<223> OTHER INFORMATION: Synthetic

<400> SEQUENCE: 95
tcgggcttcc ttac 14

<210> SEQ ID NO 96
<211> LENGTH: 16
<212> TYPE: DNA
<213> ORGANISM: Artificial Sequence
<220> FEATURE:

<223> OTHER INFORMATION: Synthetic

<400> SEQUENCE: 96
tgttcaacgt gttcat 16

<210> SEQ ID NO 97
<211> LENGTH: 17
<212> TYPE: DNA
<213> ORGANISM: Artificial Sequence
<220> FEATURE:
<223> OTHER INFORMATION: Synthetic

<400> SEQUENCE: 97
tgttcaacat gttcatg 17

<210> SEQ ID NO 98
<211> LENGTH: 13
<212> TYPE: DNA
<213> ORGANISM: Artificial Sequence
<220> FEATURE:
<223> OTHER INFORMATION: Synthetic

<400> SEQUENCE: 98
ccgcagcact atg 13

<210> SEQ ID NO 99
<211> LENGTH: 13
<212> TYPE: DNA
<213> ORGANISM: Artificial Sequence
<220> FEATURE:
<223> OTHER INFORMATION: Synthetic

<400> SEQUENCE: 99
tccgcagcgc tat 13

<210> SEQ ID NO 100
<211> LENGTH: 17
<212> TYPE: DNA
<213> ORGANISM: Artificial Sequence
<220> FEATURE:
<223> OTHER INFORMATION: Synthetic

<400> SEQUENCE: 100
ctgctaaaca acataac 17

<210> SEQ ID NO 101
<211> LENGTH: 17
<212> TYPE: DNA
<213> ORGANISM: Artificial Sequence
<220> FEATURE:
<223> OTHER INFORMATION: Synthetic

<400> SEQUENCE: 101
ctgctaaaca atataac 17

<210> SEQ ID NO 102
<211> LENGTH: 16
<212> TYPE: DNA
<213> ORGANISM: Artificial Sequence
<220> FEATURE:
<223> OTHER INFORMATION: Synthetic

<400> SEQUENCE: 102
ctgcagatag aaggtt 16

<210> SEQ ID NO 103
<211> LENGTH: 16
<212> TYPE: DNA
<213> ORGANISM: Artificial Sequence
<220> FEATURE:
<223> OTHER INFORMATION: Synthetic

<400> SEQUENCE: 103
ctgcagattg aaggtt 16

<210> SEQ ID NO 104
<211> LENGTH: 16
<212> TYPE: DNA
<213> ORGANISM: Artificial Sequence
<220> FEATURE:
<223> OTHER INFORMATION: Synthetic

<400> SEQUENCE: 104
agaggctaaa aaggcc 16

<210> SEQ ID NO 105
<211> LENGTH: 16
<212> TYPE: DNA
<213> ORGANISM: Artificial Sequence
<220> FEATURE:
<223> OTHER INFORMATION: Synthetic

<400> SEQUENCE: 105
agaggctaga aaggcc 16

<210> SEQ ID NO 106
<211> LENGTH: 16
<212> TYPE: DNA
<213> ORGANISM: Artificial Sequence
<220> FEATURE:
<223> OTHER INFORMATION: Synthetic

<400> SEQUENCE: 106
ggtagtctcc tccctt 16

<210> SEQ ID NO 107
<211> LENGTH: 16
<212> TYPE: DNA
<213> ORGANISM: Artificial Sequence
<220> FEATURE:
<223> OTHER INFORMATION: Synthetic

<400> SEQUENCE: 107
ggtagtcttc tccctt 16

<210> SEQ ID NO 108
<211> LENGTH: 16
<212> TYPE: DNA
<213> ORGANISM: Artificial Sequence
<220> FEATURE:
<223> OTHER INFORMATION: Synthetic

<400> SEQUENCE: 108
ggaatcgtaa acgtaa 16

<210> SEQ ID NO 109
<211> LENGTH: 16
<212> TYPE: DNA
<213> ORGANISM: Artificial Sequence
<220> FEATURE:
<223> OTHER INFORMATION: Synthetic

<400> SEQUENCE: 109
ggaatcgtta acgtaa 16

<210> SEQ ID NO 110
<211> LENGTH: 16
<212> TYPE: DNA
<213> ORGANISM: Artificial Sequence
<220> FEATURE:
<223> OTHER INFORMATION: Synthetic

<400> SEQUENCE: 110
gggcccatct ccgggc 16

<210> SEQ ID NO 111
<211> LENGTH: 16
<212> TYPE: DNA
<213> ORGANISM: Artificial Sequence
<220> FEATURE:
<223> OTHER INFORMATION: Synthetic

<400> SEQUENCE: 111
gggcccattt ccgggc 16

<210> SEQ ID NO 112
<211> LENGTH: 16
<212> TYPE: DNA
<213> ORGANISM: Artificial Sequence
<220> FEATURE:
<223> OTHER INFORMATION: Synthetic

<400> SEQUENCE: 112
tagagagacc tagaat 16

<210> SEQ ID NO 113
<211> LENGTH: 16
<212> TYPE: DNA
<213> ORGANISM: Artificial Sequence
<220> FEATURE:
<223> OTHER INFORMATION: Synthetic

<400> SEQUENCE: 113
tagagagatc tagaat 16

<210> SEQ ID NO 114
<211> LENGTH: 16
<212> TYPE: DNA
<213> ORGANISM: Artificial Sequence
<220> FEATURE:
<223> OTHER INFORMATION: Synthetic

<400> SEQUENCE: 114
aatctgtaag agttgc 16

<210> SEQ ID NO 115
<211> LENGTH: 16
<212> TYPE: DNA
<213> ORGANISM: Artificial Sequence
<220> FEATURE:
<223> OTHER INFORMATION: Synthetic

<400> SEQUENCE: 115
aatctgtacg agttgc 16

<210> SEQ ID NO 116
<211> LENGTH: 16

<212> TYPE: DNA
<213> ORGANISM: Artificial Sequence
<220> FEATURE:
<223> OTHER INFORMATION: Synthetic

<400> SEQUENCE: 116
tgttgttcca aaagct 16

<210> SEQ ID NO 117
<211> LENGTH: 16
<212> TYPE: DNA
<213> ORGANISM: Artificial Sequence
<220> FEATURE:
<223> OTHER INFORMATION: Synthetic

<400> SEQUENCE: 117
tgttgttcta aaagct 16

<210> SEQ ID NO 118
<211> LENGTH: 16
<212> TYPE: DNA
<213> ORGANISM: Artificial Sequence
<220> FEATURE:
<223> OTHER INFORMATION: Synthetic

<400> SEQUENCE: 118
ttccttttat tgttgc 16

<210> SEQ ID NO 119
<211> LENGTH: 16
<212> TYPE: DNA
<213> ORGANISM: Artificial Sequence
<220> FEATURE:
<223> OTHER INFORMATION: Synthetic

<400> SEQUENCE: 119
ttccttttgt tgttgc 16

<210> SEQ ID NO 120
<211> LENGTH: 16
<212> TYPE: DNA
<213> ORGANISM: Artificial Sequence
<220> FEATURE:
<223> OTHER INFORMATION: Synthetic

<400> SEQUENCE: 120
aagaatgcac aagagc 16

<210> SEQ ID NO 121
<211> LENGTH: 16
<212> TYPE: DNA
<213> ORGANISM: Artificial Sequence
<220> FEATURE:
<223> OTHER INFORMATION: Synthetic

<400> SEQUENCE: 121
aagaatgcgc aagagc 16

<210> SEQ ID NO 122
<211> LENGTH: 16
<212> TYPE: DNA
<213> ORGANISM: Artificial Sequence
<220> FEATURE:
<223> OTHER INFORMATION: Synthetic

<400> SEQUENCE: 122
gatggaacca attctg 16

<210> SEQ ID NO 123
<211> LENGTH: 16
<212> TYPE: DNA
<213> ORGANISM: Artificial Sequence
<220> FEATURE:
<223> OTHER INFORMATION: Synthetic

<400> SEQUENCE: 123
gatggaacta attctg 16

<210> SEQ ID NO 124
<211> LENGTH: 16
<212> TYPE: DNA
<213> ORGANISM: Artificial Sequence
<220> FEATURE:
<223> OTHER INFORMATION: Synthetic

<400> SEQUENCE: 124
attagcaaac aaagag 16

<210> SEQ ID NO 125
<211> LENGTH: 16
<212> TYPE: DNA
<213> ORGANISM: Artificial Sequence
<220> FEATURE:
<223> OTHER INFORMATION: Synthetic

<400> SEQUENCE: 125
attagcaagc aaagag 16

<210> SEQ ID NO 126
<211> LENGTH: 16
<212> TYPE: DNA
<213> ORGANISM: Artificial Sequence
<220> FEATURE:
<223> OTHER INFORMATION: Synthetic

<400> SEQUENCE: 126
tgctcaatat gttttt 16

<210> SEQ ID NO 127
<211> LENGTH: 16
<212> TYPE: DNA
<213> ORGANISM: Artificial Sequence
<220> FEATURE:
<223> OTHER INFORMATION: Synthetic

<400> SEQUENCE: 127
tgctcaatgt gttttt 16

<210> SEQ ID NO 128
<211> LENGTH: 16
<212> TYPE: DNA
<213> ORGANISM: Artificial Sequence
<220> FEATURE:
<223> OTHER INFORMATION: Synthetic

<400> SEQUENCE: 128
gtaatataaa ccatag 16

<210> SEQ ID NO 129
<211> LENGTH: 16
<212> TYPE: DNA
<213> ORGANISM: Artificial Sequence
<220> FEATURE:
<223> OTHER INFORMATION: Synthetic

<400> SEQUENCE: 129
gtaatataca ccatag 16

<210> SEQ ID NO 130
<211> LENGTH: 16
<212> TYPE: DNA
<213> ORGANISM: Artificial Sequence
<220> FEATURE:
<223> OTHER INFORMATION: Synthetic

<400> SEQUENCE: 130
ttttcgttac tgtgaa 16

<210> SEQ ID NO 131
<211> LENGTH: 16
<212> TYPE: DNA
<213> ORGANISM: Artificial Sequence
<220> FEATURE:
<223> OTHER INFORMATION: Synthetic

<400> SEQUENCE: 131
ttttcgttcc tgtgaa 16

<210> SEQ ID NO 132
<211> LENGTH: 16
<212> TYPE: DNA
<213> ORGANISM: Artificial Sequence
<220> FEATURE:
<223> OTHER INFORMATION: Synthetic

<400> SEQUENCE: 132
agggaaagag agattc 16

<210> SEQ ID NO 133
<211> LENGTH: 16
<212> TYPE: DNA
<213> ORGANISM: Artificial Sequence
<220> FEATURE:
<223> OTHER INFORMATION: Synthetic

<400> SEQUENCE: 133
agggaaaggg agattc 16

<210> SEQ ID NO 134
<211> LENGTH: 16
<212> TYPE: DNA
<213> ORGANISM: Artificial Sequence
<220> FEATURE:
<223> OTHER INFORMATION: Synthetic

<400> SEQUENCE: 134
ggattgttag tttgtt 16

<210> SEQ ID NO 135
<211> LENGTH: 16
<212> TYPE: DNA
<213> ORGANISM: Artificial Sequence
<220> FEATURE:
<223> OTHER INFORMATION: Synthetic

<400> SEQUENCE: 135
ggattgttgg tttgtt 16

<210> SEQ ID NO 136
<211> LENGTH: 16
<212> TYPE: DNA
<213> ORGANISM: Artificial Sequence
<220> FEATURE:
<223> OTHER INFORMATION: Synthetic

<400> SEQUENCE: 136
tccctcagct cagctg 16

<210> SEQ ID NO 137
<211> LENGTH: 16
<212> TYPE: DNA
<213> ORGANISM: Artificial Sequence
<220> FEATURE:
<223> OTHER INFORMATION: Synthetic

<400> SEQUENCE: 137
tccctcagtt cagctg 16

<210> SEQ ID NO 138
<211> LENGTH: 16
<212> TYPE: DNA
<213> ORGANISM: Artificial Sequence
<220> FEATURE:
<223> OTHER INFORMATION: Synthetic

<400> SEQUENCE: 138
gtgaaggacc ttgtgt 16

<210> SEQ ID NO 139
<211> LENGTH: 16
<212> TYPE: DNA
<213> ORGANISM: Artificial Sequence
<220> FEATURE:
<223> OTHER INFORMATION: Synthetic

<400> SEQUENCE: 139
gtgaaggatc ttgtgt 16

<210> SEQ ID NO 140
<211> LENGTH: 16
<212> TYPE: DNA
<213> ORGANISM: Artificial Sequence
<220> FEATURE:
<223> OTHER INFORMATION: Synthetic

<400> SEQUENCE: 140
ttcctatccg ggtctc 16

<210> SEQ ID NO 141
<211> LENGTH: 16
<212> TYPE: DNA
<213> ORGANISM: Artificial Sequence
<220> FEATURE:
<223> OTHER INFORMATION: Synthetic

<400> SEQUENCE: 141
ttcctatctg ggtctc 16

<210> SEQ ID NO 142
<211> LENGTH: 16
<212> TYPE: DNA
<213> ORGANISM: Artificial Sequence
<220> FEATURE:
<223> OTHER INFORMATION: Synthetic

<400> SEQUENCE: 142
gaggtgatat tgctgt 16

<210> SEQ ID NO 143
<211> LENGTH: 16
<212> TYPE: DNA
<213> ORGANISM: Artificial Sequence
<220> FEATURE:
<223> OTHER INFORMATION: Synthetic

<400> SEQUENCE: 143
gaggtgatgt tgctgt 16

<210> SEQ ID NO 144
<211> LENGTH: 17
<212> TYPE: DNA
<213> ORGANISM: Artificial Sequence
<220> FEATURE:
<223> OTHER INFORMATION: Synthetic

<400> SEQUENCE: 144
tttgatcctc tgcagat 17

<210> SEQ ID NO 145
<211> LENGTH: 17
<212> TYPE: DNA
<213> ORGANISM: Artificial Sequence
<220> FEATURE:
<223> OTHER INFORMATION: Synthetic

<400> SEQUENCE: 145
gtaatgcata gaggcta 17

<210> SEQ ID NO 146
<211> LENGTH: 17
<212> TYPE: DNA
<213> ORGANISM: Artificial Sequence
<220> FEATURE:
<223> OTHER INFORMATION: Synthetic

<400> SEQUENCE: 146
tctaccgcag gtagtct 17

<210> SEQ ID NO 147
<211> LENGTH: 17
<212> TYPE: DNA
<213> ORGANISM: Artificial Sequence
<220> FEATURE:
<223> OTHER INFORMATION: Synthetic

<400> SEQUENCE: 147
tggctatggg gaatcgt 17

<210> SEQ ID NO 148
<211> LENGTH: 17
<212> TYPE: DNA
<213> ORGANISM: Artificial Sequence
<220> FEATURE:
<223> OTHER INFORMATION: Synthetic

<400> SEQUENCE: 148
tggctctgcg ggcccat 17

<210> SEQ ID NO 149

<211> LENGTH: 17
<212> TYPE: DNA
<213> ORGANISM: Artificial Sequence
<220> FEATURE:
<223> OTHER INFORMATION: Synthetic

<400> SEQUENCE: 149
gattgaaatt agagaga 17

<210> SEQ ID NO 150
<211> LENGTH: 17
<212> TYPE: DNA
<213> ORGANISM: Artificial Sequence
<220> FEATURE:
<223> OTHER INFORMATION: Synthetic

<400> SEQUENCE: 150
tttctgaccc aatctgt 17

<210> SEQ ID NO 151
<211> LENGTH: 17
<212> TYPE: DNA
<213> ORGANISM: Artificial Sequence
<220> FEATURE:
<223> OTHER INFORMATION: Synthetic

<400> SEQUENCE: 151
atttcgattt gttgttc 17

<210> SEQ ID NO 152
<211> LENGTH: 17
<212> TYPE: DNA
<213> ORGANISM: Artificial Sequence
<220> FEATURE:
<223> OTHER INFORMATION: Synthetic

<400> SEQUENCE: 152
tagatctttt tcctttt 17

<210> SEQ ID NO 153
<211> LENGTH: 17
<212> TYPE: DNA
<213> ORGANISM: Artificial Sequence
<220> FEATURE:
<223> OTHER INFORMATION: Synthetic

<400> SEQUENCE: 153
ggaagactta agaatgc 17

<210> SEQ ID NO 154
<211> LENGTH: 17
<212> TYPE: DNA
<213> ORGANISM: Artificial Sequence
<220> FEATURE:
<223> OTHER INFORMATION: Synthetic

<400> SEQUENCE: 154
cgacaggagg atggaac 17

<210> SEQ ID NO 155
<211> LENGTH: 17
<212> TYPE: DNA
<213> ORGANISM: Artificial Sequence
<220> FEATURE:
<223> OTHER INFORMATION: Synthetic

<400> SEQUENCE: 155
tatcagtaaa ttagcaa 17

<210> SEQ ID NO 156
<211> LENGTH: 17
<212> TYPE: DNA
<213> ORGANISM: Artificial Sequence
<220> FEATURE:
<223> OTHER INFORMATION: Synthetic

<400> SEQUENCE: 156
aacaaccttt gctcaat 17

<210> SEQ ID NO 157
<211> LENGTH: 17
<212> TYPE: DNA
<213> ORGANISM: Artificial Sequence
<220> FEATURE:
<223> OTHER INFORMATION: Synthetic

<400> SEQUENCE: 157
atctacagag taatata 17

<210> SEQ ID NO 158
<211> LENGTH: 17
<212> TYPE: DNA
<213> ORGANISM: Artificial Sequence
<220> FEATURE:
<223> OTHER INFORMATION: Synthetic

<400> SEQUENCE: 158
tggaattttt tttcgtt 17

<210> SEQ ID NO 159
<211> LENGTH: 17
<212> TYPE: DNA
<213> ORGANISM: Artificial Sequence
<220> FEATURE:
<223> OTHER INFORMATION: Synthetic

<400> SEQUENCE: 159
aggatcaaca gggaaag 17

<210> SEQ ID NO 160
<211> LENGTH: 17
<212> TYPE: DNA
<213> ORGANISM: Artificial Sequence
<220> FEATURE:
<223> OTHER INFORMATION: Synthetic

<400> SEQUENCE: 160
tttgggtgtg gattgtt 17

<210> SEQ ID NO 161
<211> LENGTH: 17
<212> TYPE: DNA
<213> ORGANISM: Artificial Sequence
<220> FEATURE:
<223> OTHER INFORMATION: Synthetic

<400> SEQUENCE: 161
ggaagctact ccctcag 17

<210> SEQ ID NO 162
<211> LENGTH: 17
<212> TYPE: DNA

<213> ORGANISM: Artificial Sequence
<220> FEATURE:
<223> OTHER INFORMATION: Synthetic

<400> SEQUENCE: 162
gataagtctg tgaagga 17

<210> SEQ ID NO 163
<211> LENGTH: 16
<212> TYPE: DNA
<213> ORGANISM: Artificial Sequence
<220> FEATURE:
<223> OTHER INFORMATION: Synthetic

<400> SEQUENCE: 163
acgctatttt cctatc 16

<210> SEQ ID NO 164
<211> LENGTH: 17
<212> TYPE: DNA
<213> ORGANISM: Artificial Sequence
<220> FEATURE:
<223> OTHER INFORMATION: Synthetic

<400> SEQUENCE: 164
attttttggg aggtgat 17

<210> SEQ ID NO 165
<211> LENGTH: 12
<212> TYPE: DNA
<213> ORGANISM: Glycine max

<400> SEQUENCE: 165
aattacatat ct 12

<210> SEQ ID NO 166
<211> LENGTH: 10
<212> TYPE: DNA
<213> ORGANISM: Glycine max

<400> SEQUENCE: 166
aattccaacc 10

<210> SEQ ID NO 167
<211> LENGTH: 12
<212> TYPE: DNA
<213> ORGANISM: Glycine max

<400> SEQUENCE: 167
ggccaatttt tt 12

<210> SEQ ID NO 168
<211> LENGTH: 12
<212> TYPE: DNA
<213> ORGANISM: Glycine max

<400> SEQUENCE: 168
aattccaaaa cc 12

<210> SEQ ID NO 169
<211> LENGTH: 10
<212> TYPE: DNA
<213> ORGANISM: Glycine max

<400> SEQUENCE: 169

```
ggaattaatt                                                           10


<210> SEQ ID NO 170
<211> LENGTH: 10
<212> TYPE: DNA
<213> ORGANISM: Glycine max

<400> SEQUENCE: 170

aattaaaacc                                                           10


<210> SEQ ID NO 171
<211> LENGTH: 10
<212> TYPE: DNA
<213> ORGANISM: Glycine max

<400> SEQUENCE: 171

aaaatttttt                                                           10


<210> SEQ ID NO 172
<211> LENGTH: 12
<212> TYPE: DNA
<213> ORGANISM: Glycine max

<400> SEQUENCE: 172

agctaatttt tt                                                        12


<210> SEQ ID NO 173
<211> LENGTH: 10
<212> TYPE: DNA
<213> ORGANISM: Glycine max

<400> SEQUENCE: 173

aattccaacc                                                           10


<210> SEQ ID NO 174
<211> LENGTH: 12
<212> TYPE: DNA
<213> ORGANISM: Glycine max

<400> SEQUENCE: 174

ggccaaaaaa cc                                                        12
```

METHODS AND COMPOSITIONS FOR SELECTING SOYBEAN PLANTS RESISTANT TO BROWN STEM ROT

CROSS-REFERENCE TO RELATED APPLICATIONS

This application is a divisional of U.S. patent application Ser. No. 13/230,587 filed Sep. 12, 2011, now abandoned, which is a divisional of U.S. patent application Ser. No. 12/165,744, filed Jul. 1, 2008, now abandoned, which claims the benefit of U.S. Provisional Patent Application No. 60/948,367, filed Jul. 6, 2007, all of which are incorporated herein in their entireties.

INCORPORATION OF SEQUENCE LISTING

A sequence listing is contained in the file named "46-21_55220-SEQLIST amended ST25.txt" which is 59202 bytes (measured in MS-Windows) and was created on Jan. 9, 2013. This electronic sequence listing is electronically filed herewith and is incorporated herein by reference.

FIELD

The present invention generally relates to the field of plant breeding and disease resistance. More specifically, the invention includes a method for breeding soybean plants containing quantitative trait loci (QTL) that are associated with resistance to *Phialophora gregata*, a fungus associated with Brown Stem Rot (BSR) and isolated nucleic acid compositions for the identification and selection of BSR resistant soybean plants. The invention further provides germplasm and the use of germplasm containing QTL conferring resistance to BSR for introgression into elite germplasm in a breeding program that is obtained with the methods and compositions of the invention.

BACKGROUND

Brown stem rot (BSR) is a major disease of soybean (*Glycine max*) that is prevalent in the soybean-growing regions of the northern United States (U.S.) and in Canada (Klos, et al., *Crop Sci* 40:1445-1452 (2000)). The causative agent, *Phialophora gregata*, is a soil-borne fungus which can induce browning of internal stem and root tissue and can cause premature leaf abscission in susceptible plants. A major effect of *P. gregata* infection is loss of yield which has been estimated to exceed 20 million bushels a year in the north central U.S. (Doupnik B., *Plant Disease*, 77: 1170-1171 (1993)). Two strains of *P. gregata* have been identified, both of which are associated with yield loss in soybean. The defoliating Type I strain results in more severe symptoms than the non-defoliating Type II strain (Hughs, et al., *Plant Disease* 86:729-735 (2002)). *P. gregata* enters soybean plants through the roots and then infects pith and vascular tissue. The pathogen does not produce long-term survival structures; however, it can reproduce in soybean residue remaining in a field. Subsequent soybean crops planted in fields harboring such infected soybean residue may develop BSR.

Methods to control BSR include crop rotation and planting BSR resistant soybean varieties. Three quantitative trait loci, Rbs1, Rbs2 and Rbs3, have been described which are associated with BSR resistance in soybean. Rbs1 was described in soybean variety L78-4094 (Hanson, et al., *Crop Sci* 28:41-43 (1988)), Rbs2 in PI 437833 (Hanson, et al., *Crop Sci* 28:41-43 (1988)), and Rbs3 in PI 437970 (Willmot and Nickell, *Crop Sci* 29:672-674 (1989)). All three resistance loci are located on Linkage Group J (LG J) of the soybean genetic linkage map (Cregan, et al., *Crop Sci* 39:1464-1490 (1999); Bachman et al., *Crop Sci* 41:527-535 (2001); Patzoldt, et al., *Crop Sci* 45:1092-1095 (2005)).

Selection for BSR resistant plants based on phenotypic screening is labor-intensive and time consuming. The use of molecular markers in a soybean breeding program can greatly increase the efficiency of selection for and introgression of BSR resistance in plants. Marker analysis has identified simple sequence repeat (SSR) markers such as SATT244 linked to Rbs loci (Bachman et al., *Crop Sci* 41:527-535 (2001)). Molecular markers have been used in soybean breeding to detect, and select for, BSR resistance loci. In the case of BSR susceptible plants, molecular markers can be used to introgress BSR resistance from BSR resistant sources. Restriction fragment length polymorphisms (RFLPs) have been provided for BSR resistant locus Rbs3 (U.S. Pat. No. 5,689,035 and U.S. Pat. No. 5,948,953). In addition, SSRs, expressed sequence tags (ESTs), and RFLPs have been provided for Rbs1, Rbs2, and Rbs3 (U.S. Patent Application Publication Number 2006/0041955).

Of the classes of markers, single nucleotide polymorphisms (SNPs) have characteristics which make them preferential to other genetic markers in detecting, selecting for, and introgressing BSR resistance in a soybean plant. SNPs occur in plant populations as a result of single nucleotide substitutions or insertion/deletion (INDEL) events in the genomes of individual plants. SNPs are preferred because technologies are available for automated, high-throughput screening of SNP markers, which can decrease the time and resources needed to select for and introgress BSR resistance in soybean plants. Further, SNP markers are ideal because the likelihood that a particular SNP allele is derived from independent origins in the extant population of a particular species is very low. As such, SNP markers are useful for tracking and assisting introgression of BSR resistance alleles, particularly in the case of BSR resistance haplotypes. A need exists for a SNP based marker set to screen for resistance to BSR. The present invention provides a SNP-based marker set for Rbs1, Rbs2, and Rbs3 on Linkage Group J. As used herein, the term "Rbs" includes Rbs1, Rbs2, and Rbs3.

The present invention provides and includes methods and compositions for screening and selecting a soybean plant comprising QTL for BSR resistance that were derived from mapping populations using endemic strains of *Phialophora gregata* and single nucleotide polymorphisms (SNP) marker technology.

SUMMARY OF THE INVENTION

The present invention provides methods of introgressing an allele associated with Brown Stem Rot (BSR) resistance into a soybean plant comprising the steps of: (A) crossing at least one Brown Stem Rot (BSR) resistant plant comprising at least one first genotype with at least one other plant comprising at least one second genotype to form a segregating population; (B) genotyping at least one soybean plant in the segregating population with respect to one or more soybean genomic DNA markers selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37; and (C) selecting from the segregating population at least one soybean plant comprising at least one first genotype from said BSR resistant plant. In these methods, at least two, five, ten or twenty soybean genomic DNA markers selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37 can be genotyped in the soybean plant from the segregating population in step (B). In other embodiments of these methods, all of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and SEQ ID NO: 37 are genotyped in the soybean plant from the segregating population in step (B). In certain embodiments of the method provided, the cross in step (A) can be effected by mechanical emasculation, chemical sterilization, or genetic sterilization of a pollen acceptor. In certain embodiments of the methods, genotyping is effected in step (B) by determining the allelic state of at least one of the provided soybean genomic DNA markers. The allelic state of the provided markers can be determined by an assay which is selected from the group consisting of single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, and Flap Endonuclease-mediated assays.

The methods provided by this invention can further comprise the step (D) of assaying the selected soybean plant for resistance to a BSR-inducing fungus. In the methods comprising this step, the BSR-inducing fungus can be a *Philophora* sp. Also, the *Philophora* sp. can be a *Philophora gregata* species. The *Philophora gregata* species can be a *Philophora gregata* strain Type I or *Philophora gregata* strain Type II.

The methods of the invention can also further comprise the step of crossing the soybean plant selected in step (C) to another soybean plant. The methods of the invention can also further comprise the step of obtaining seed from the soybean plant selected in step (C). The methods of the invention also provide for genotyping at least one soybean plant in the segregating population with respect to both a soybean genomic DNA marker selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37 and with respect to another soybean genomic DNA marker selected from the group consisting of SEQ ID NO:33.

The invention also provides for soybean plant produced according to methods entailing use of a soybean genomic DNA marker selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37. Soybean plants produced by these methods can be resistant to a BSR-inducing fungus. Resistance can be to a *Philophora* sp., a *Philophora gregata* species, or a *Philophora gregata* strain Type I or *Philophora gregata* strain Type II. The soybean plant produced by the methods can be an elite soybean plant.

The invention further provides methods of introgressing a BSR resistance allele into a soybean plant comprising the steps of: (A) crossing at least one BSR resistant soybean plant with at least one BSR sensitive soybean plant in order to obtain a segregating population; (B) genotyping at least one soybean plant in the segregating population with respect to one or more soybean genomic DNA markers selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37; and (C) selecting from the segregating population one or more soybean plants comprising a haplotype associated with BSR resistance, wherein the BSR resistance haplotype is associated with a Rbs BSR resistance locus. In the methods, the Rbs BSR resistance locus can comprise Rbs1, Rbs2, and Rbs3. Alternatively, the Rbs BSR resistance locus can be selected from the group consisting of Rbs1, Rbs2, and Rbs3. The source of Rbs can be elite germplasm or accession germplasm. This method can be used to produce soybean plants. The soybean plants produced can be an elite soybean plant. The soybean or elite soybean plant produced can exhibit any of at least partial resistance or at least substantial resistance to a BSR-inducing fungus. The BSR-inducing fungus can be a *Philophora gregata* species or a *Philophora gregata* species selected from the group consisting of *Philophora gregata* strain Type I and Type II.

The soybean or elite soybean plants produced by any of the methods of this invention can further comprises a transgenic trait. The transgenic trait can be selected from the group consisting of herbicide tolerance, increased yield, insect control, fungal disease resistance, virus resistance, nematode resistance, bacterial disease resistance, *mycoplasma* disease resistance, modified oils production, high oil production, high protein production, germination and/or seedling growth control, enhanced animal and human nutrition, low raffinose, environmental stress resistance, increased digestibility, improved processing traits, improved flavor, nitrogen fixation, hybrid seed production, and/or reduced allergenicity. The herbicide tolerance trait can be selected from the group consisting of glyphosate, dicamba, glufosinate, sulfonylurea, bromoxynil and norflurazon herbicide resistance traits.

This invention also provides isolated nucleic acids. These isolated nucleic acids can be used in practicing the methods of the invention. Isolated nucleic acid molecules for detecting a molecular marker representing a polymorphism in soybean DNA can comprise at least 15 nucleotides that include or are immediately adjacent to the polymorphism, wherein the nucleic acid molecule is at least 90% identical to a sequence of the same number of consecutive nucleotides in either strand of DNA that include or are immediately adjacent to the polymorphism, and wherein the molecular marker is selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37 are provided. The isolated nucleic acid can further comprise a detectable label or provide for incorporation of a detectable label. This detectable label can be selected from the group consisting of an isotope, a fluorophore, an oxidant, a reductant, a nucleotide and a hapten. This detectable label can be added to the nucleic acid by a chemical reaction or incorporated by an enzymatic reaction. Isolated nucleic acid molecules provided herein can comprises at least 16, 17, 18, or 20 nucleotides on either strand of the DNA that include or are immediately adjacent to the polymorphism. In other embodiments, the isolated nucleic acid can hybridize to at least one allele of the molecular marker under stringent hybridization conditions.

The isolated nucleic acids of the invention include but are not limited to nucleic acids or oligonucleotides that detect a corresponding molecular marker as follows:

i) an oligonucleotide that is at least 90% identical to SEQ ID NOs: 70 or 71 that detects the SEQ ID NO: 1 molecular marker;

ii) an oligonucleotide that is at least 90% identical to SEQ ID NOs: 72 or 73 that detects a SEQ ID NO: 2 molecular marker;

iii) an oligonucleotide that is at least 90% identical to SEQ ID NOs: 74 or 75 that detects a SEQ ID NO: 3 molecular marker;

iv) an oligonucleotide that is at least 90% identical to SEQ ID NOs: 76 or 77 that detects a SEQ ID NO: 4 molecular marker;

v) a nucleic acid that is at least 90% identical to an oligonucleotide selected from the group consisting of SEQ ID NOs: 144, 102, and 103 that detects a SEQ ID NO: 5 molecular marker;

vi) a nucleic acid that is at least 90% identical to an oligonucleotide selected from the group consisting of SEQ ID NOs: 145, 104, and 105 that detects a SEQ ID NO: 6 molecular marker;

vii) an oligonucleotide that is at least 90% identical to SEQ ID NOs: 82 or 83 that detects a SEQ ID NO: 9 molecular marker;

viii) a nucleic acid that is at least 90% identical to an oligonucleotide selected from the group consisting of SEQ ID NOs: 146, 106, and 107 that detects a SEQ ID NO: 10 molecular marker;

ix) a nucleic acid that is at least 90% identical to an oligonucleotide selected from the group consisting of SEQ ID NOs: 147, 108, and 109 that detects a SEQ ID NO: 11 molecular marker;

x) a nucleic acid that is at least 90% identical to an oligonucleotide selected from the group consisting of SEQ ID NOs: 148, 110, and 111 that detects a SEQ ID NO: 12 molecular marker;

xi) a nucleic acid that is at least 90% identical to an oligonucleotide selected from the group consisting of SEQ ID NOs: 149, 112, and 113 that detects a SEQ ID NO: 13 molecular marker;

xii) a nucleic acid that is at least 90% identical to an oligonucleotide selected from the group consisting of SEQ ID NOs: 150, 114, and 115 that detects a SEQ ID NO: 14 molecular marker;

xiii) a nucleic acid that is at least 90% identical to an oligonucleotide selected from the group consisting of SEQ ID NOs: 151, 116, and 117 that detects a SEQ ID NO: 16 molecular marker;

xiv) a nucleic acid that is at least 90% identical to an oligonucleotide selected from the group consisting of SEQ ID NOs: 152, 118, and 119 that detects a SEQ ID NO: 18 molecular marker;

xv) a nucleic acid that is at least 90% identical to an oligonucleotide selected from the group consisting of SEQ ID NOs: 153, 120, and 121 that detects a SEQ ID NO: 20 molecular marker;

xvi) a nucleic acid that is at least 90% identical to an oligonucleotide selected from the group consisting of SEQ ID NOs: 154, 122, and 123 that detects a SEQ ID NO: 21 molecular marker;

xvii) an oligonucleotide that is at least 90% identical to SEQ ID NOs: 90 or 91 that detects a SEQ ID NO: 22 molecular marker;

xviii) an oligonucleotide that is at least 90% identical to SEQ ID NOs: 92 or 93 that detects a SEQ ID NO: 23 molecular marker;

xix) an oligonucleotide that is at least 90% identical to SEQ ID NOs: 94 or 95 that detects a SEQ ID NO: 24 molecular marker;

xx) a nucleic acid that is at least 90% identical to an oligonucleotide selected from the group consisting of SEQ ID NOs: 155, 124, and 125 that detects a SEQ ID NO: 25 molecular marker;

xxi) a nucleic acid that is at least 90% identical to an oligonucleotide selected from the group consisting of SEQ ID NOs: 156, 126, and 127 that detects a SEQ ID NO: 26 molecular marker;

xxii) a nucleic acid that is at least 90% identical to an oligonucleotide selected from the group consisting of SEQ ID NOs: 157, 128, and 129 that detects a SEQ ID NO: 27 molecular marker;

xxiv) a nucleic acid that is at least 90% identical to an oligonucleotide selected from the group consisting of SEQ ID NOs: 158, 138, and 139 that detects a SEQ ID NO: 28 molecular marker;

xxv) a nucleic acid that is at least 90% identical to an oligonucleotide selected from the group consisting of SEQ ID NOs: 159, 132, and 133 that detects a SEQ ID NO: 29 molecular marker;

xxvi) a nucleic acid that is at least 90% identical to an oligonucleotide selected from the group consisting of SEQ ID NOs: 160, 134, and 135 that detects a SEQ ID NO: 30 molecular marker;

xxvii) an oligonucleotide that is at least 90% identical to SEQ ID NOs: 98 or 99 that detects a SEQ ID NO: 32 molecular marker;

xxviii) an oligonucleotide that is at least 90% identical to SEQ ID NOs: 100 or 101 that detects a SEQ ID NO: 34 molecular marker;

xxix) a nucleic acid that is at least 90% identical to an oligonucleotide selected from the group consisting of SEQ ID NOs: 162, 138, and 139 that detects a SEQ ID NO: 35 molecular marker;

xxx) a nucleic acid that is at least 90% identical to an oligonucleotide selected from the group consisting of SEQ ID NOs: 163, 140, and 141 that detects a SEQ ID NO: 36 molecular marker; and xxxi) a nucleic acid is at least 90% identical to an oligonucleotide selected from the group consisting of SEQ ID NOs: 164, 142, and 143 that detects a SEQ ID NO: 37 molecular marker.

The invention also provides compositions comprising sets of oligonucleotides that can be used to genotype the polymorphisms of a molecular marker that is selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37. The sets of oligonucleotides can comprise: (A) a pair of oligonucleotide primers wherein each of said primers comprises at least 12 contiguous nucleotides and wherein said pair of primers permit PCR amplification of a DNA segment comprising a molecular marker selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37; and (B) at least one detector oligonucleotide that permits detection of a polymorphism in said amplified segment, wherein the sequence of said detector oligonucleotide is at least 90 percent identical to a sequence of at least 12 contiguous nucleotides in either strand of a segment of soybean DNA that include or are immediately adjacent to said polymorphism of step (A). In certain embodiments, the detector oligonucleotide comprise at least 12 nucleotides and either provide for incorporation of a detectable label or further comprises a detectable label. The detectable label can be selected from the group consisting of an isotope, a fluorophore, an oxidant, a reductant, a nucleotide and a hapten. In other embodiments of the invention, the detector oligonucleotide and the oligonucleotide primers hybridize to at least one allele of said molecular marker under stringent hybridization conditions. In still other embodiments, the set of oligonucleotides can further comprise a second detector oligonucleotide capable of detecting a second polymorphism of the molecular marker that is distinct from the polymorphism detected by a first detector oligonucleotide of the set of oligonucleotides. The set of oligonucleotides can also further comprise a second detector oligonucleotide capable of detecting a distinct allele of the same polymorphism detected by a first detector oligonucleotide of the set of oligonucleotides.

Specific sets of detector oligonucleotides and amplification primers for genotyping each of the molecular markers selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37 are also contemplated by this invention. When the molecular marker is SEQ ID NO: 1, the oligonucleotide primers can be at least 90% identical to SEQ ID NOs: 38 and 39, and the detector oligonucleotide can comprises a nucleic acid that is at least 90% identical to SEQ ID NOs: 70 or 71. Sets of oligonucleotides of substantially similar design can be used to genotype SEQ ID NOs: 2, 3, 4, 5, 6, 9, 10, 11, 12, 13, 14, 16, 18, 20, 21, 22, 23, 24, 25, 26, 27, 28, 29, 30, 32, 34, 35, 36, and 37 molecular markers and are also provided herein.

Other sets of oligonucleotides of this invention include, but are not limited to, oligonucleotide sets wherein the molecular marker is SEQ ID NO: 1 and wherein the detector oligonucleotide comprises a nucleic acid that is at least 90% identical to SEQ ID NOs: 70 or 71; oligonucleotide sets wherein the molecular marker is SEQ ID NO: 2 and wherein the detector oligonucleotide comprises a nucleic acid that is at least 90% identical to SEQ ID NOs: 72 or 73; oligonucleotide sets wherein the molecular marker is SEQ ID NO: 3 and wherein the detector oligonucleotide comprises a nucleic acid that is at least 90% identical to SEQ ID NOs: 74 or 75; oligonucleotide sets wherein the molecular marker is SEQ ID NO: 4 and wherein the detector oligonucleotide comprises a nucleic acid that is at least 90% identical to SEQ ID NOs: 76 or 77; oligonucleotide sets wherein the molecular marker is SEQ ID NO: 5 and wherein the detector oligonucleotide comprises a nucleic acid that is at least 90% identical to SEQ ID NOs: 102, 103, or 144; oligonucleotide sets wherein the molecular marker is SEQ ID NO: 6 and wherein the detector oligonucleotide comprises a nucleic acid that is at least 90% identical to SEQ ID NOs: 104, 105, or 145; oligonucleotide sets wherein the molecular marker is SEQ ID NO: 9 and wherein the detector oligonucleotide comprises a nucleic acid that is at least 90% identical to SEQ ID NOs: 82 or 83; oligonucleotide sets wherein the molecular marker is SEQ ID NO: 10 and wherein the detector oligonucleotide comprises a nucleic acid that is at least 90% identical to SEQ ID NOs: 106, 107, or 146; oligonucleotide sets wherein the molecular marker is SEQ ID NO: 11 and wherein the detector oligonucleotide comprises a nucleic acid that is at least 90% identical to SEQ ID NOs: 108, 109, or 147; oligonucleotide sets wherein the molecular marker is SEQ ID NO: 12 and wherein the detector oligonucleotide comprises a nucleic acid that is at least 90% identical to SEQ ID NOs: 110, 111, or 148; oligonucleotide sets wherein the molecular marker is SEQ ID NO: 13 and wherein the detector oligonucleotide comprises a nucleic acid that is at least 90% identical to SEQ ID NOs: 112, 113 or 149; oligonucleotide sets wherein the molecular marker is SEQ ID NO: 14 and wherein the detector oligonucleotide comprises a nucleic acid that is at least 90% identical to SEQ ID NOs: 114, 115, or 150; oligonucleotide sets wherein the molecular marker is SEQ ID NO: 16 and wherein the detector oligonucleotide comprises a nucleic acid that is at least 90% identical to SEQ ID NOs: 116, 117 or 151; oligonucleotide sets wherein the molecular marker is SEQ ID NO: 18 and wherein the detector oligonucleotide comprises a nucleic acid that is at least 90% identical to SEQ ID NOs: 118, 119, or 152; oligonucleotide sets wherein the molecular marker is SEQ ID NO: 20 and wherein the detector oligonucleotide comprises a nucleic acid that is at least 90% identical to SEQ ID NOs: 120, 121, or 153; oligonucleotide sets wherein the molecular marker is SEQ ID NO: 21 and wherein the detector oligonucleotide comprises a nucleic acid that is at least 90% identical to SEQ ID NOs: 122, 123, or 154; oligonucleotide sets wherein the molecular marker is SEQ ID NO: 22 and wherein the detector oligonucleotide comprises a nucleic acid that is at least 90% identical to SEQ ID NOs: 90 or 91; oligonucleotide sets wherein the molecular marker is SEQ ID NO: 23 and wherein the detector oligonucleotide comprises a nucleic acid that is at least 90% identical to SEQ ID NOs: 92 or 93; oligonucleotide sets wherein the molecular marker is SEQ ID NO: 24 and wherein the detector oligonucleotide comprises a nucleic acid that is at least 90% identical to SEQ ID NOs: 94 or 95; oligonucleotide sets wherein the molecular marker is SEQ ID NO: 25 and wherein the detector oligonucleotide comprises a nucleic acid that is at least 90% identical to SEQ ID NOs: 124, 125, or 155; oligonucleotide sets wherein the molecular marker is SEQ ID NO: 26 and wherein the detector oligonucleotide comprises a nucleic acid that is at least 90% identical to SEQ ID NOs: 126, 127, or 156; oligonucleotide sets wherein the molecular marker is SEQ ID NO: 27 and wherein the detector oligonucleotide comprises a nucleic acid that is at least 90% identical to SEQ ID NOs: 128, 129 or 157; oligonucleotide sets wherein the molecular marker is SEQ ID NO: 28 and wherein the detector oligonucleotide comprises a nucleic acid that is at least 90% identical to SEQ ID NOs: 130, 131, or 158; oligonucleotide sets wherein the molecular marker is SEQ ID NO: 29 and wherein the detector oligonucleotide comprises a nucleic acid that is at least 90% identical to SEQ ID NOs: 132, 133, or 159; oligonucleotide sets wherein the molecular marker is SEQ ID NO: 30 and wherein the detector oligonucleotide comprises a nucleic acid that is at least 90% identical to SEQ ID NOs: 134, 135, or 160; oligonucleotide sets wherein the molecular marker is SEQ ID NO: 32 and wherein the detector oligonucleotide comprises a nucleic acid that is at least 90% identical to SEQ ID NOs: 98 or 99; oligonucleotide sets wherein the molecular marker is SEQ ID NO: 34 and wherein the detector oligonucleotide comprises a nucleic acid that is at least 90% identical to SEQ ID NOs: 100 or 101; oligonucleotide sets wherein the molecular marker is SEQ ID NO: 35 and wherein the detector oligonucleotide comprises a nucleic acid that is at least 90% identical to SEQ ID NOs: 138, 139, or 162; oligonucleotide sets wherein the molecular marker is SEQ ID NO: 36 and wherein the detector oligonucleotide comprises a nucleic acid that is at least 90% identical to SEQ ID NOs: 140, 141, or 163; and oligonucleotide sets wherein the molecular marker is SEQ ID NO: 37 and wherein the detector oligonucleotide comprises a nucleic acid that is at least 90% identical to SEQ ID NOs: 142, 143, or 164.

Also provided herein are methods of identifying a soybean plant comprising at least one allele associated with Brown Stem Rot (BSR) resistance in a soybean plant comprising the steps of: (A) genotyping at least one soybean plant with respect to one or more soybean genomic DNA markers selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37; and (B) selecting at least one soybean plant comprising an allele of said marker associated with Brown Stem Rot (BSR) resistance, thereby identifying a soybean plant comprising at least one allele associated with Brown Stem Rot (BSR) resistance. In certain embodiments of this method, at least two or at least five soybean genomic DNA markers selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37 are genotyped in at least one soybean plant in step (A). In still other embodiments, methods that further comprise the step (C) of assaying said selected soybean plant for resistance to a BSR-inducing fungus are provided. In other embodiments, the BSR-inducing fungus is a *Philophora* sp. In certain embodiments of this method, an allele of said marker associated with Brown Stem Rot (BSR) resistance is provided in Table 6. In other embodiments, genotyping is effected in step (A) by determining the allelic state of at least one of said soybean genomic DNA markers. In still other embodiments, this method can further comprise the step of crossing the soybean plant selected in step (B) to another soybean plant or can further comprise the step of obtaining seed from the soybean plant selected in step (B). In other embodiments of the methods, at least one soybean plant in the segregating population is genotyped with respect to a soybean genomic DNA marker selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37 and with respect to another soybean genomic DNA marker selected from the group consisting of SEQ ID NO: 33. In certain embodiments of this method, the soybean plant that is genotyped in step (A) is from a segregating population obtained by crossing at least one Brown Stem Rot (BSR) resistant plant comprising at least one first genotype with at least one other plant comprising at least one second genotype.

Also provided herein are methods of introgressing a BSR resistance allele into a soybean plant comprising the steps of: (A) crossing at least one BSR resistant soybean plant with at least one BSR sensitive soybean plant in order to obtain a segregating population; (B) genotyping at least one soybean plant in the segregating population with respect to a haplotype characterized by one or more soybean genomic DNA markers selected from the group consisting of SEQ ID NOs: 1, 2, 3, 4, 5, 6, 9, 10, 11, 12, 13, 14, 16, 18, 20, 21, 22, 23, 24, 25, 26, 27, 28, 29, 30, 32, 34, 35, 36, and 37; and (C) selecting from the segregating population one or more soybean plants comprising a haplotype associated with BSR resistance, wherein the BSR resistance haplotype is associated with a Rbs BSR resistance locus, thereby introgressing a BSR resistance allele into a soybean plant In certain embodiments of this method, the Rbs BSR resistance locus comprises Rbs1, Rbs2, or Rbs3. In other embodiments of this method, the Rbs BSR resistance locus is selected from the group consisting of Rbs1, Rbs2, and Rbs3. In other embodiments of the methods, the source of Rbs is elite germplasm or the source of Rbs is accession germplasm. Elite soybean plants obtained by this method and it's various embodiments are also provided herein.

BRIEF DESCRIPTION OF THE DRAWINGS

The accompanying drawings, which are incorporated in and form a part of the specification, illustrate the embodiments of the present invention and together with the description, serve to explain the principles of the invention.

In the drawings:

FIG. 1. Single marker effects of SNP markers from an association study using pre-commercial lines are shown.

BRIEF DESCRIPTION OF NUCLEIC ACID SEQUENCES

SEQ ID NO: 1 is a genomic sequence derived from *Glycine max* associated with BSR resistance locus Rbs.

SEQ ID NO: 2 is a genomic sequence derived from *Glycine max* associated with BSR resistance locus Rbs.

SEQ ID NO: 3 is a genomic sequence derived from *Glycine max* associated with BSR resistance locus Rbs.

SEQ ID NO: 4 is a genomic sequence derived from *Glycine max* associated with BSR resistance locus Rbs.

SEQ ID NO: 5 is a genomic sequence derived from *Glycine max* associated with BSR resistance locus Rbs.

SEQ ID NO: 6 is a genomic sequence derived from *Glycine max* associated with BSR resistance locus Rbs.

SEQ ID NO: 7 is a genomic sequence derived from *Glycine max* associated with BSR resistance locus Rbs.

SEQ ID NO: 8 is a genomic sequence derived from *Glycine max* associated with BSR resistance locus Rbs.

SEQ ID NO: 9 is a genomic sequence derived from *Glycine max* associated with BSR resistance locus Rbs.

SEQ ID NO: 10 is a genomic sequence derived from *Glycine max* associated with BSR resistance locus Rbs.

SEQ ID NO: 11 is a genomic sequence derived from *Glycine max* associated with BSR resistance locus Rbs.

SEQ ID NO: 12 is a genomic sequence derived from *Glycine max* associated with BSR resistance locus Rbs.

SEQ ID NO: 13 is a genomic sequence derived from *Glycine max* associated with BSR resistance locus Rbs.

SEQ ID NO: 14 is a genomic sequence derived from *Glycine max* associated with BSR resistance locus Rbs.

SEQ ID NO: 15 is a genomic sequence derived from *Glycine max* associated with BSR resistance locus Rbs.

SEQ ID NO: 16 is a genomic sequence derived from *Glycine max* associated with BSR resistance locus Rbs.

SEQ ID NO: 17 is a genomic sequence derived from *Glycine max* associated with BSR resistance locus Rbs.

SEQ ID NO: 18 is a genomic sequence derived from *Glycine max* associated with BSR resistance locus Rbs.

SEQ ID NO: 19 is a genomic sequence derived from *Glycine max* associated with BSR resistance locus Rbs.

SEQ ID NO: 20 is a genomic sequence derived from *Glycine max* associated with BSR resistance locus Rbs.

SEQ ID NO: 21 is a genomic sequence derived from *Glycine max* associated with BSR resistance locus Rbs.

SEQ ID NO: 22 is a genomic sequence derived from *Glycine max* associated with BSR resistance locus Rbs.

SEQ ID NO: 23 is a genomic sequence derived from *Glycine max* associated with BSR resistance locus Rbs.

SEQ ID NO: 24 is a genomic sequence derived from *Glycine max* associated with BSR resistance locus Rbs.

SEQ ID NO: 25 is a genomic sequence derived from *Glycine max* associated with BSR resistance locus Rbs.

SEQ ID NO: 26 is a genomic sequence derived from *Glycine max* associated with BSR resistance locus Rbs.

SEQ ID NO: 27 is a genomic sequence derived from *Glycine max* associated with BSR resistance locus Rbs.

SEQ ID NO: 28 is a genomic sequence derived from *Glycine max* associated with BSR resistance locus Rbs.

SEQ ID NO: 29 is a genomic sequence derived from *Glycine max* associated with BSR resistance locus Rbs.

SEQ ID NO: 30 is a genomic sequence derived from *Glycine max* associated with BSR resistance locus Rbs.

SEQ ID NO: 31 is a genomic sequence derived from *Glycine max* associated with BSR resistance locus Rbs.

SEQ ID NO: 32 is a genomic sequence derived from *Glycine max* associated with BSR resistance locus Rbs.

SEQ ID NO: 33 is a genomic sequence derived from *Glycine max* associated with BSR resistance locus Rbs.

SEQ ID NO: 34 is a genomic sequence derived from *Glycine max* associated with BSR resistance locus Rbs.

SEQ ID NO: 35 is a genomic sequence derived from *Glycine max* associated with BSR resistance locus Rbs.

SEQ ID NO: 36 is a genomic sequence derived from *Glycine max* associated with BSR resistance locus Rbs.

SEQ ID NO: 37 is a genomic sequence derived from *Glycine max* associated with BSR resistance locus Rbs.

SEQ ID NO: 38 is a forward PCR primer for the amplification of a region of SEQ ID NO: 1.

SEQ ID NO: 39 is a reverse PCR primer for the amplification of a region of SEQ ID NO: 1.

SEQ ID NO: 40 is a forward PCR primer for the amplification of a region of SEQ ID NO: 2.

SEQ ID NO: 41 is a reverse PCR primer for the amplification of a region of SEQ ID NO: 2.

SEQ ID NO: 42 is a forward PCR primer for the amplification of a region of SEQ ID NO: 3.

SEQ ID NO: 43 is a reverse PCR primer for the amplification of a region of SEQ ID NO: 3.

SEQ ID NO: 44 is a forward PCR primer for the amplification of a region of SEQ ID NO: 4.

SEQ ID NO: 45 is a reverse PCR primer for the amplification of a region of SEQ ID NO: 4.

SEQ ID NO: 46 is a forward PCR primer for the amplification of a region of SEQ ID NO: 7.

SEQ ID NO: 47 is a reverse PCR primer for the amplification of a region of SEQ ID NO: 7.

SEQ ID NO: 48 is a forward PCR primer for the amplification of a region of SEQ ID NO: 8.

SEQ ID NO: 49 is a reverse PCR primer for the amplification of a region of SEQ ID NO: 8.

SEQ ID NO: 50 is a forward PCR primer for the amplification of a region of SEQ ID NO: 9.

SEQ ID NO: 51 is a reverse PCR primer for the amplification of a region of SEQ ID NO: 9.

SEQ ID NO: 52 is a forward PCR primer for the amplification of a region of SEQ ID NO: 15.

SEQ ID NO: 53 is a reverse PCR primer for the amplification of a region of SEQ ID NO: 15.

SEQ ID NO: 54 is a forward PCR primer for the amplification of a region of SEQ ID NO: 17.

SEQ ID NO: 55 is a reverse PCR primer for the amplification of a region of SEQ ID NO: 17.

SEQ ID NO: 56 is a forward PCR primer for the amplification of a region of SEQ ID NO: 19.

SEQ ID NO: 57 is a reverse PCR primer for the amplification of a region of SEQ ID NO: 19.

SEQ ID NO: 58 is a forward PCR primer for the amplification of a region of SEQ ID NO: 22.

SEQ ID NO: 59 is a reverse PCR primer for the amplification of a region of SEQ ID NO: 22.

SEQ ID NO: 60 is a forward PCR primer for the amplification of a region of SEQ ID NO: 23.

SEQ ID NO: 61 is a reverse PCR primer for the amplification of a region of SEQ ID NO: 23.

SEQ ID NO: 62 is a forward PCR primer for the amplification of a region of SEQ ID NO: 24.

SEQ ID NO: 63 is a reverse PCR primer for the amplification of a region of SEQ ID NO: 24.

SEQ ID NO: 64 is a forward PCR primer for the amplification of a region of SEQ ID NO: 31.

SEQ ID NO: 65 is a reverse PCR primer for the amplification of a region of SEQ ID NO: 31.

SEQ ID NO: 66 is a forward PCR primer for the amplification of a region of SEQ ID NO: 32.

SEQ ID NO: 67 is a reverse PCR primer for the amplification of a region of SEQ ID NO: 32.

SEQ ID NO: 68 is a forward PCR primer for the amplification of a region of SEQ ID NO: 34.

SEQ ID NO: 69 is a reverse PCR primer for the amplification of a region of SEQ ID NO: 34.

SEQ ID NO: 70 is a first probe for the detection of the SNP of a region of SEQ ID NO: 1

SEQ ID NO: 71 is a second probe for the detection of a SNP of SEQ ID NO: 1.

SEQ ID NO: 72 is a first probe for the detection of a SNP of SEQ ID NO: 2.

SEQ ID NO: 73 is a second probe for the detection of a SNP of SEQ ID NO: 2.

SEQ ID NO: 74 is a first probe for the detection of a SNP of SEQ ID NO: 3.

SEQ ID NO: 75 is a second probe for the detection of a SNP of SEQ ID NO: 3.

SEQ ID NO: 76 is a first probe for the detection of a SNP of SEQ ID NO: 4.

SEQ ID NO: 77 is a second probe for the detection of a SNP of SEQ ID NO: 4.

SEQ ID NO: 78 is a first probe for the detection of a SNP of SEQ ID NO: 7.

SEQ ID NO: 79 is a second probe for the detection of a SNP of SEQ ID NO: 7.

SEQ ID NO: 80 is a first probe for the detection of a SNP of SEQ ID NO: 8.

SEQ ID NO: 81 is a second probe for the detection of a SNP of SEQ ID NO: 8.

SEQ ID NO: 82 is a first probe for the detection of a SNP of SEQ ID NO: 9.

SEQ ID NO: 83 is a second probe for the detection of a SNP of SEQ ID NO: 9.

SEQ ID NO: 84 is a first probe for the detection of a SNP of SEQ ID NO: 15.

SEQ ID NO: 85 is a second probe for the detection of a SNP of SEQ ID NO: 15.

SEQ ID NO: 86 is a first probe for the detection of a SNP of SEQ ID NO: 17.

SEQ ID NO: 87 is a second probe for the detection of a SNP of SEQ ID NO: 17.

SEQ ID NO: 88 is a first probe for the detection of a SNP of SEQ ID NO: 19.

SEQ ID NO: 89 is a second probe for the detection of a SNP of SEQ ID NO: 19.

SEQ ID NO: 90 is a first probe for the detection of a SNP of SEQ ID NO: 22.

SEQ ID NO: 91 is a second probe for the detection of a SNP of SEQ ID NO: 22.

SEQ ID NO: 92 is a first probe for the detection of a SNP of SEQ ID NO: 23.

SEQ ID NO: 93 is a second probe for the detection of a SNP of SEQ ID NO: 23.

SEQ ID NO: 94 is a first probe for the detection of a SNP of SEQ ID NO: 24.

SEQ ID NO: 95 is a second probe for the detection of a SNP of SEQ ID NO: 24.

SEQ ID NO: 96 is a first probe for the detection of a SNP of SEQ ID NO: 31.

SEQ ID NO: 97 is a second probe for the detection of a SNP of SEQ ID NO: 31.

SEQ ID NO: 98 is a first probe for the detection of a SNP of SEQ ID NO: 32.

SEQ ID NO: 99 is a second probe for the detection of a SNP of SEQ ID NO: 32.

SEQ ID NO: 100 is a first probe for the detection of a SNP of SEQ ID NO: 34.

SEQ ID NO: 101 is a second probe for the detection of a SNP of SEQ ID NO: 34.

SEQ ID NO: 102 is a first probe for the detection of a SNP of SEQ ID NO: 5.

SEQ ID NO: 103 is a second probe for the detection of a SNP of SEQ ID NO: 5.

SEQ ID NO: 104 is a first probe for the detection of a SNP of SEQ ID NO: 6.

SEQ ID NO: 105 is a second probe for the detection of a SNP of SEQ ID NO: 6.

SEQ ID NO: 106 is a first probe for the detection of a SNP of SEQ ID NO: 10.

SEQ ID NO: 107 is a second probe for the detection of a SNP of SEQ ID NO: 10.

SEQ ID NO: 108 is a first probe for the detection of a SNP of SEQ ID NO: 11.

SEQ ID NO: 109 is a second probe for the detection of a SNP of SEQ ID NO: 11.

SEQ ID NO: 110 is a first probe for the detection of a SNP of SEQ ID NO: 12.

SEQ ID NO: 111 is a second probe for the detection of a SNP of SEQ ID NO: 12.

SEQ ID NO: 112 is a first probe for the detection of a SNP of SEQ ID NO: 13.

SEQ ID NO: 113 is a second probe for the detection of a SNP of SEQ ID NO: 13.

SEQ ID NO: 114 is a first probe for the detection of a SNP of SEQ ID NO: 14.

SEQ ID NO: 115 is a second probe for the detection of a SNP of SEQ ID NO: 14.

SEQ ID NO: 116 is a first probe for the detection of a SNP of SEQ ID NO: 16.

SEQ ID NO: 117 is a second probe for the detection of a SNP of SEQ ID NO: 16.

SEQ ID NO: 118 is a first probe for the detection of a SNP of SEQ ID NO: 18.

SEQ ID NO: 119 is a second probe for the detection of a SNP of SEQ ID NO: 18.

SEQ ID NO: 120 is a first probe for the detection of a SNP of SEQ ID NO: 20.

SEQ ID NO: 121 is a second probe for the detection of a SNP of SEQ ID NO: 20.

SEQ ID NO: 122 is a first probe for the detection of a SNP of SEQ ID NO: 21.

SEQ ID NO: 123 is a second probe for the detection of a SNP of SEQ ID NO: 21.

SEQ ID NO: 124 is a first probe for the detection of a SNP of SEQ ID NO: 25.

SEQ ID NO: 125 is a second probe for the detection of a SNP of SEQ ID NO: 25.

SEQ ID NO: 126 is a first probe for the detection of a SNP of SEQ ID NO: 26.

SEQ ID NO: 127 is a second probe for the detection of a SNP of SEQ ID NO: 26.

SEQ ID NO: 128 is a first probe for the detection of a SNP of SEQ ID NO: 27.

SEQ ID NO: 129 is a second probe for the detection of a SNP of SEQ ID NO: 27.

SEQ ID NO: 130 is a first probe for the detection of a SNP of SEQ ID NO: 28.

SEQ ID NO: 131 is a second probe for the detection of a SNP of SEQ ID NO: 28.

SEQ ID NO: 132 is a first probe for the detection of a SNP of SEQ ID NO: 29.

SEQ ID NO: 133 is a second probe for the detection of a SNP of SEQ ID NO: 29.

SEQ ID NO: 134 is a first probe for the detection of a SNP of SEQ ID NO: 30.

SEQ ID NO: 135 is a second probe for the detection of a SNP of SEQ ID NO: 30.

SEQ ID NO: 136 is a first probe for the detection of a SNP of SEQ ID NO: 33.

SEQ ID NO: 137 is a second probe for the detection of a SNP of SEQ ID NO: 33.

SEQ ID NO: 138 is a first probe for the detection of a SNP of SEQ ID NO: 35.

SEQ ID NO: 139 is a second probe for the detection of a SNP of SEQ ID NO: 35,

SEQ ID NO: 140 is a first probe for the detection of a SNP of SEQ ID NO: 36.

SEQ ID NO: 141 is a second probe for the detection of a SNP of SEQ ID NO: 36.

SEQ ID NO: 142 is a first probe for the detection of a SNP of SEQ ID NO: 37.

SEQ ID NO: 143 is a second probe for the detection of a SNP of SEQ ID NO: 37.

SEQ ID NO: 144 is a third probe for the detection of a SNP of SEQ ID NO: 5.

SEQ ID NO: 145 is a third probe for the detection of a SNP of SEQ ID NO: 6.

SEQ ID NO: 146 is a third probe for the detection of a SNP of SEQ ID NO: 10.

SEQ ID NO: 147 is a third probe for the detection of a SNP of SEQ ID NO: 11.

SEQ ID NO: 148 is a third probe for the detection of a SNP of SEQ ID NO: 12.

SEQ ID NO: 149 is a third probe for the detection of a SNP of SEQ ID NO: 13.

SEQ ID NO: 150 is a third probe for the detection of a SNP of SEQ ID NO: 14.

SEQ ID NO: 151 is a third probe for the detection of a SNP of SEQ ID NO: 16.

SEQ ID NO: 152 is a third probe for the detection of a SNP of SEQ ID NO: 18.

SEQ ID NO: 153 is a third probe for the detection of a SNP of SEQ ID NO: 20.

SEQ ID NO: 154 is a third probe for the detection of a SNP of SEQ ID NO: 21.

SEQ ID NO: 155 is a third probe for the detection of a SNP of SEQ ID NO: 25.

SEQ ID NO: 156 is a third probe for the detection of a SNP of SEQ ID NO: 26.

SEQ ID NO: 157 is a third probe for the detection of a SNP of SEQ ID NO: 27.

SEQ ID NO: 158 is a third probe for the detection of a SNP of SEQ ID NO: 28.

SEQ ID NO: 159 is a third probe for the detection of a SNP of SEQ ID NO: 29.

SEQ ID NO: 160 is a third probe for the detection of a SNP of SEQ ID NO: 30.

SEQ ID NO: 161 is a third probe for the detection of a SNP of SEQ ID NO: 33.

SEQ ID NO: 162 is a third probe for the detection of a SNP of SEQ ID NO: 35.

SEQ ID NO: 163 is a third probe for the detection of a SNP of SEQ ID NO: 36.

SEQ ID NO: 164 is a third probe for the detection of a SNP of SEQ ID NO: 37.

DETAILED DESCRIPTION OF INVENTION

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biology of The Cell, 3rd Edition, Garland Publishing, Inc.: New York, 1994; Rieger et al., Glossary of Genetics: Classical and Molecular, 5th edition, Springer-Verlag: New York, 1991; and Lewin, Genes V, Oxford University Press: New York, 1994. The nomenclature for DNA bases as set forth by 37 CFR §1.822 is used. As used herein certain terms and phrases are defined as follows.

An "allele" refers to an alternative sequence at a particular locus; the length of an allele can be as small as 1 nucleotide base, but is typically larger. Allelic sequence can be amino acid sequence or nucleic acid sequence.

A "locus" is a short sequence that is usually unique and usually found at one particular location in the genome by a point of reference; e.g., a short DNA sequence that is a gene, or part of a gene or intergenic region. A locus of this invention can be a unique PCR product at a particular location in the genome. The loci of this invention comprise one or more polymorphisms; i.e., alternative alleles present in some individuals.

An "allelic state" refers to the nucleic acid sequence that is present in a nucleic acid molecule that contains a genomic polymorphism. For example, the nucleic acid sequence of a DNA molecule that contains a single nucleotide polymorphism may comprise an A, C, G, or T residue at the polymorphic position such that the allelic state is defined by which residue is present at the polymorphic position. For example, the nucleic acid sequence of an RNA molecule that contains a single nucleotide polymorphism may comprise an A, C, G, or U residue at the polymorphic position such that the allelic state is defined by which residue is present at the polymorphic position. Similarly, the nucleic acid sequence of a nucleic acid molecule that contains an Indel may comprise an insertion or deletion of nucleic acid sequences at the polymorphic position such that the allelic state is defined by the presence or absence of the insertion or deletion at the polymorphic position.

An "association" when used in reference to a polymorphism and a phenotypic trait or trait index, refers to any statistically significant correlation between the presence of a given allele of a polymorphic locus and the phenotypic trait or trait index value, wherein the value may be qualitative or quantitative.

A "distinct set of nucleic acid molecules" refers to one or more nucleic acid molecules that hybridize to DNA sequences that are included, are immediately adjacent to, or are within about 1000 base pairs of either the 5' or 3' end of a given soybean genomic polymorphism. In certain embodiments, the distinct set of nucleic acid molecules will comprise a single nucleic acid sequence that includes or is immediately adjacent to a given polymorphism. In other embodiments, the distinct set of nucleic acid molecules will comprise one or more nucleic acid sequences that include or are immediately adjacent to the polymorphism as well as other nucleic acid sequences that are within about 1000 base pairs of either the 5' or 3' end of the polymorphism.

A "marker" or "molecular marker" as used herein is a DNA sequence (e.g., a gene or part of a gene) exhibiting polymorphism between two or more plants of the same species, which can be identified or typed by a simple assay. Useful polymorphisms include single nucleotide polymorphisms (SNPs), insertions or deletions in DNA sequence (Indels), single feature polymorphisms (SFPs), and simple sequence repeats of DNA sequence (SSRs).

"Marker assay" refers to a method for detecting a polymorphism at a particular locus using a particular method. Methods for detecting polymorphisms include, but are not limited to, restriction fragment length polymorphism (RFLP), single base extension, electrophoresis, sequence alignment, allelic specific oligonucleotide hybridization (ASO), RAPD, allele-specific primer extension sequencing (ASPE), DNA sequencing, RNA sequencing, microarray-based analyses, universal PCR, allele specific extension, hybridization, mass spectrometry, ligation, extension-ligation, endonuclease-mediated dye release assays and Flap Endonuclease-mediated assays. Exemplary single base extension assays are disclosed in U.S. Pat. No. 6,013,431. Exemplary endonuclease-mediated dye release assays for allelic state determination of SNPs where an endonuclease activity releases a reporter dye from a hybridization probe are disclosed in U.S. Pat. No. 5,538,848.

"Single nucleotide polymorphism (SNP)" refers to a polymorphism at a single site wherein the polymorphism constitutes a single base pair change, an insertion of one or more base pairs, or a deletion of one or more base pairs.

"Genotype" refers to the specification of an allelic composition at one or more loci within an individual organism. In the case of diploid organisms, there are two alleles at each locus; a diploid genotype is said to be homozygous when the alleles are the same, and heterozygous when the alleles are different.

"Haplotype" refers to an allelic segment of genomic DNA that tends to be inherited as a unit; such haplotypes can be characterized by one or more polymorphic molecular markers and can be defined by a size of not greater than 10-12 centimorgans. With higher precision provided by a higher density of polymorphisms, haplotypes can be characterized by genomic windows, for example, in the range of 1-5 centimorgans.

"Haplotype window" refers to a contiguous genomic region that can be defined, and tracked, with a set of one or more polymorphic markers wherein the polymorphisms indicate identity by descent. A haplotype within that window can be defined by the unique fingerprint of alleles at each marker. Thus, identity by state between two inbred individuals (or two gametes) at one or more molecular marker loci located within this region is taken as evidence of identity-by-descent of the entire region. Each haplotype window includes at least one polymorphic molecular marker. Haplotype windows can be mapped along each chromosome in the genome. Haplotype windows are not fixed per se and, given the ever-increasing density of molecular markers, this invention anticipates that the number and size of haplotype windows to change with increasing marker density. It is anticipated that the number of haplotype windows will increase and their respective sizes will decrease as marker density increases, thus resulting in an ever-increasing degree of confidence in ascertaining identity by descent based on the identity by state at the marker loci.

The phrase "Identity by descent" (IBD) refers to the state of two alleles when they are identical copies of the same ancestral allele.

The phrase "Identity by state" (IBS) refers to the state of two alleles when they are identical copies.

The phrase "immediately adjacent" when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "immediately adjacent" to the polymorphism.

"Interrogation position" refers to a physical position on a solid support that can be queried to obtain genotyping data for one or more predetermined genomic polymorphisms.

"Consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

"Phenotype" refers to the detectable characteristics of a cell or organism which are a manifestation of gene expression.

"Phenotypic trait index" refers to a composite value for at least two phenotypic traits, wherein each phenotypic trait may be assigned a weight to reflect relative importance for selection.

"Linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will be of each genotype. Segregation of gametes into genotypes differing from ¼ are attributed to linkage.

"Linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

"Quantitative trait locus (QTL)" refers to a locus that controls to some degree traits that are usually continuously distributed.

As used herein "sequence identity" refers to the extent to which two optimally aligned polynucleotide or peptide sequences are invariant throughout a window of alignment of components, e.g. nucleotides or amino acids. An "identity fraction" for aligned segments of a test sequence and a reference sequence is the number of identical components which are shared by the two aligned sequences divided by the total number of components in reference sequence segment, i.e. the entire reference sequence or a smaller defined part of the reference sequence. "Percent identity" is the identity fraction times 100.

As used herein, "typing" refers to any method whereby the specific allelic form of a given soybean genomic polymorphism is determined. For example, a single nucleotide polymorphism (SNP) is typed by determining which nucleotide is present (i.e. an A, G, T, or C). Insertion/deletions (Indels) are determined by determining if the Indel is present. Indels can be typed by a variety of assays including, but not limited to, marker assays.

As used herein, the term "soybean" refers to *Glycine max* and includes all plant varieties that can be bred with *Glycine max*, including wild soybean species. Soybean plants include members of the genus *Glycine*, more specifically comprising *Glycine arenaria, Glycine argyrea, Glycine canescens, Glycine clandestine, Glycine curvata, Glycine cyrtoloba, Glycine falcate, Glycine latifolia, Glycine latrobeana, Glycine max, Glycine microphylla, Glycine pescadrensis, Glycine pindanica, Glycine rubiginosa, Glycine soja, Glycine* sp., *Glycine stenophita, Glycine tabacina* and *Glycine tomentella*.

As used herein, the term "elite line" means any line that has resulted from breeding and selection for superior agronomic performance. An elite plant is any plant from an elite line.

As used herein, Rbs includes Rbs1, Rbs2, and Rbs3.

The following detailed description relates to the isolated nucleic acid compositions and related methods for genotyping soybean plants. In general, these compositions and methods can be used to genotype soybean plants from the genus *Glycine* (e.g., *Glycine arenaria, Glycine argyrea, Glycine canescens, Glycine clandestine, Glycine curvata, Glycine cyrtoloba, Glycine falcate, Glycine latifolia, Glycine latrobeana, Glycine max, Glycine microphylla, Glycine pescadrensis, Glycine pindanica, Glycine rubiginosa, Glycine soja, Glycine* sp., *Glycine stenophita, Glycine tabacina* and *Glycine tomentella*). More specifically, soybean plants from the species *Glycine max* and the subspecies *Glycine max* L. ssp. max or *Glycine max* ssp. *formosana* can be genotyped using these compositions and methods. In an additional aspect, the soybean plant is from the species *Glycine soja*, otherwise known as wild soybean, can be genotyped using these compositions and methods. Alternatively, soybean germplasm derived from any of *Glycine max, Glycine max* L. ssp. max, *Glycine max* ssp. *Formosana*, and/or *Glycine soja* can be genotyped using compositions and methods provided herein.

As used herein, "Brown Stem Rot" (BSR) refers to a plant disease that is caused or induced by one or more fungi. In one aspect, BSR is caused or induced by fungi in the genus *Phialophora*. In another aspect, BSR is caused or induced by *Phialophora gregata* strain "Type I." In yet another aspect, BSR is caused or induced by *Phialophora gregata* strain "Type II."

To the extent to which any of the preceding definitions is inconsistent with definitions provided in any patent or non-patent reference incorporated herein or in any reference found elsewhere, it is understood that the preceding definition will be used herein.

Methods of Introgressing Alleles Associated with BSR Resistance

The present invention provides a methods of introgressing one or more allele(s) associated with BSR resistance into a soybean plant. Non-limiting sources of Rbs alleles that provide BSR resistance can include accession germplasm, such as plant introductions, exotic germplasm and elite germplasm. In the methods described herein, soybean plants comprising Rbs alleles that provide BSR resistance are typically crossed to distinct soybean plants that lack such Rbs alleles to obtain a segregating population.

The present invention concerns typing of alleles associated with the BSR resistance locus Rbs that is located on Linkage Group J. SNP markers used to monitor the introgression of Rbs include the SEQ ID NOs: 1-32, and 34-37 molecular markers that are also respectively referred to herein as NS0096111, NS0115388, NS0097529, NS0125407, NS0117865, NS0118789, NS0136063, NS0116003, NS0121329, NS0097011, NS0205207, NS0205545, NS0136255, NS0202657, NS0205390, NS0202839, NS0206116, NS0205513, NS0098342, NS0204723, NS0205732, NS0205990, NS0205742, NS0097836, NS0115925, NS0203163, NS0203256, NS0205987, NS0204644, NS0205506, NS0203006, NS0102178, NS0119351, NS0202621, NS0205432, and NS0206363. Certain alleles associated with the SEQ ID NOs: 1-37 markers that can be used to monitor introgression of BSR resistance are provided in Table 7. In certain embodiments, the BSR resistance locus Rbs SNP marker DNA sequences (SEQ ID NOs: 1 through SEQ ID NO: 37) can be amplified using the primers indicated as SEQ ID NOs: 38 through SEQ ID NO: 71 and detected with probes indicated as SEQ ID NOs: 72 through 164, wherein the corresponding primer and probe sets provide assays for the detection of alleles associated with BSR resistance, immunity, or susceptibility in *Glycine max*.

The BSR disease resistant QTL allele or alleles can be introduced from any plant that contains that allele (donor) to any recipient soybean plant. In one aspect, the recipient soybean plant can contain additional BSR resistant loci. In another aspect, the recipient soybean plant can contain a transgene. In another aspect, while maintaining the introduced QTL, the genetic contribution of the plant providing the disease resistant QTL can be reduced by back-crossing or other suitable approaches. In one aspect, the nuclear genetic material derived from the donor material in the soybean plant can be less than or about 50%, less than or about 25%, less than or about 13%, less than or about 5%, 3%, 2% or 1%, but that genetic material contains the BSR resistant locus or loci of interest.

An allele of a QTL can, of course, comprise multiple genes or other genetic factors even within a contiguous genomic region or linkage group, such as a haplotype. The alleles of the disease resistance loci described herein (i.e. SEQ ID NOs: 1-32, and 34-37 and Table 6) can therefore encompass, or serve as a molecular marker, for more than one gene or other genetic factor where each individual gene or genetic component is also capable of exhibiting allelic variation and where each gene or genetic factor is also capable of eliciting a phenotypic effect on the quantitative trait in question. In an aspect of the present invention the allele of the disclosed BSR QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in this invention can denote a haplotype within a haplotype window that provides disease resistance. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus. Plants produced by the methods of the present invention may be homozygous or heterozygous at any particular BSR locus or for a particular polymorphic marker.

Soybean plants (*Glycine max* L.) can be crossed by either natural or mechanical techniques. Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod. The critical day length for flowering ranges from about 13 h for genotypes adapted to tropical latitudes to 24 h for photoperiod-insensitive genotypes grown at higher latitudes. Soybeans seem to be insensitive to day length for 9 days after emergence. Photoperiods shorter than the critical day length are required for 7 to 26 days to complete flower induction.

Soybean flowers typically are self-pollinated on the day the corolla opens. The stigma is receptive to pollen about 1 day before anthesis and remains receptive for 2 days after anthesis, if the flower petals are not removed. Filaments of nine stamens are fused, and the one nearest the standard is free. The stamens form a ring below the stigma until about 1 day before anthesis, at which point their filaments begin to elongate rapidly and elevate the anthers around the stigma. The anthers dehisce on the day of anthesis, pollen grains fall on the stigma, and within 10 h the pollen tubes reach the ovary and fertilization is completed. Self-pollination occurs naturally in soybean with no manipulation of the flowers. For the crossing of two soybean plants, it is typically preferable, although not required, to utilize artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a soybean flower include, for example, physical removal of the male parts, use of a genetic factor conferring male sterility, and application of a chemical gametocide to the male parts.

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Genetic male sterility is available in soybeans and may be useful to facilitate hybridization in the context of the current invention, particularly for recurrent selection programs. The distance required for complete isolation of a crossing block is not clear; however, out-crossing is less than 0.5% when male-sterile plants are 12 m or more from a foreign pollen source (Boerma and Moradshahi, *Crop Sci*., 15:858-861, 1975). Plants on the boundaries of a crossing block probably sustain the most out-crossing with foreign pollen and can be eliminated at harvest to minimize contamination.

Once harvested, pods are typically air-dried at not more than 38° C. until the seeds contain 13% moisture or less, then the seeds are removed by hand. Seed can be stored satisfactorily at about 25° C. for up to a year if relative humidity is 50% or less. In humid climates, germination percentage declines rapidly unless the seed is dried to 7% moisture and stored in an air-tight container at room temperature. Long-term storage in any climate is best accomplished by drying seed to 7% moisture and storing it at 10° C. or less in a room maintained at 50% relative humidity or in an air-tight container.

Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In one aspect, a backcross or recurrent breeding program is undertaken.

The complexity of inheritance influences choice of the breeding method. Backcross breeding can be used to transfer one or a few favorable genes for a highly heritable trait into a desirable cultivar. A cultivar is a race or variety of a plant species that has been created or selected intentionally and maintained through cultivation. Plants of the present invention can be part of or generated from a breeding program.

This approach has been used extensively for breeding disease-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

The doubled haploid (DH) approach achieves isogenic plants in a shorter time frame. DH plants provide an invaluable tool to plant breeders, particularly for generating inbred lines and quantitative genetics studies. For breeders, DH populations have been particularly useful in QTL mapping, cytoplasmic conversions, and trait introgression. Moreover, there is value in testing and evaluating homozygous lines for plant breeding programs. All of the genetic variance is among progeny in a breeding cross, which improves selection gain.

Most research and breeding applications rely on artificial methods of DH production. The initial step involves the haploidization of the plant which results in the production of a population comprising haploid seed. Non-homozygous lines are crossed with an inducer parent, resulting in the production of haploid seed. Seed that has a haploid embryo, but normal triploid endosperm, advances to the second stage. That is, haploid seed and plants are any plant with a haploid embryo, independent of the ploidy level of the endosperm.

After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number. These chimeric plants are self-pollinated to produce diploid (doubled haploid) seed. This DH seed is cultivated and subsequently evaluated and used in hybrid test cross production.

Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of Crop Improvement," Longman, Inc., NY, 369-399, 1979; Sneep and Hendriksen, "Plant Breeding Perspectives," Wageningen (ed), Center for Agricultural Publishing and Documentation, 1979; Fehr, In: *Soybeans: Improvement, Production and Uses*, 2nd Edition, *Monograph.,* 16:249, 1987; Fehr, "Principles of Variety Development," *Theory and Technique*, (Vol. 1) and *Crop Species Soybean* (Vol. 2), Iowa State Univ., Macmillan Pub. Co., NY, 360-376, 1987).

Polymorphisms in DNA sequences can be detected or typed by a variety of effective methods well known in the art including, but not limited to, those disclosed in U.S. Pat. Nos. 5,468,613 and 5,217,863; 5,210,015; 5,876,930; 6,030,787; 6,004,744; 6,013,431; 5,595,890; 5,762,876; 5,945,283; 5,468,613; 6,090,558; 5,800,944; and 5,616,464, all of which are incorporated herein by reference in their entireties. However, the compositions and methods of this invention can be used in conjunction with any polymorphism typing method to type polymorphisms in soybean genomic DNA samples. These soybean genomic DNA samples used include but are not limited to soybean genomic DNA isolated directly from a soybean plant, cloned soybean genomic DNA, or amplified soybean genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe. The design of such hybridization probes requires only the provision of about 15 to 25 nucleotides that encompass the polymorphic base noted in Tables 6 or 7 or in any of the SEQ ID NOs: 1-32 or 34-37 molecular markers.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464 employing at least one pair of probes having sequences homologous to adjacent portions of the target nucleic acid sequence and having side chains which non-covalently bind to form a stem upon base pairing of said probes to said target nucleic acid sequence. At least one of the side chains has a photo-activatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is immediately adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of soybean genomic DNA which flanks a region containing the polymorphism to be assayed. Following amplification of the region of the soybean genome containing the polymorphism, the PCR product is mixed with the third oligonucleotide (called an extension primer) which is designed to hybridize to the amplified DNA immediately adjacent to the polymorphism in the presence of DNA polymerase and two differentially labeled dideoxynucleoside triphosphates. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected. The design of such probes requires only the provision of about 15 to about 50 nucleotides on either side (i.e. either 5' or 3') of the polymorphic base noted in Tables 6 or 7 or in or in any of the SEQ ID NOs: 1-32 or 34-37 molecular markers. Exemplary oligonucleotide probes for use in single base extension assays for certain molecular markers of this invention are also provided in Table 9.

In a preferred method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

A useful assay is available from AB Biosystems as the Taqman® assay which employs four synthetic oligonucleotides in a single reaction that concurrently amplifies the soybean genomic DNA, discriminates between the alleles present, and directly provides a signal for discrimination and detection. Two of the four oligonucleotides serve as PCR primers and generate a PCR product encompassing the polymorphism to be detected. Two others are allele-specific fluorescence-resonance-energy-transfer (FRET) probes. In the assay, two FRET probes bearing different fluorescent reporter dyes are used, where a unique dye is incorporated into an oligonucleotide that can anneal with high specificity to only one of the two alleles. Useful reporter dyes include, but are not limited to, 6-carboxy-4,7,2',7'-tetrachlorofluorescein (TET), T-chloro-7'-phenyl-1,4-dichloro-6-carboxyfluorescein (VIC) and 6-carboxyfluorescein phosphoramidite (FAM). A useful quencher is 6-carboxy-N,N,N',N'-tetramethylrhodamine (TAMRA). Additionally, the 3' end of each FRET probe is chemically blocked so that it can not act as a PCR primer. Also present is a third fluorophore used as a passive reference, e.g., rhodamine X (ROX) to aid in later normalization of the relevant fluorescence values (correcting for volumetric errors in reaction assembly). Amplification of the genomic DNA is initiated. During each cycle of the PCR, the FRET probes anneal in an allele-specific manner to the template DNA molecules. Annealed (but not non-annealed) FRET probes are degraded by TAQ DNA polymerase as the enzyme encounters the 5' end of the annealed probe, thus releasing the fluorophore from proximity to its quencher. Following the PCR, the fluorescence of each of the two fluorescers, as well as that of the passive reference, is determined fluorometrically. The normalized intensity of fluorescence for each of the two dyes will be proportional to the amounts of each allele initially present in the sample, and thus the genotype of the sample can be inferred.

To design primers and probes for the assay the locus sequence is first masked to prevent design of any of the three primers to sites that match known soybean repetitive elements (e.g., transposons) or are of very low sequence complexity (di- or tri-nucleotide repeat sequences). Design of primers to such repetitive elements will result in assays of low specificity, through amplification of multiple loci or annealing of the FRET probes to multiple sites.

PCR primers are designed (A) to have a length in the size range of 15 to 25 bases and matching sequences in the polymorphic locus, (B) to have a calculated melting temperature in the range of 57 to 60° C., e.g. corresponding to an optimal PCR annealing temperature of 52 to 55° C., (C) to produce a product which includes the polymorphic site and typically has a length in the size range of 75 to 250 base pairs. However, PCR techniques that permit amplification of fragments of up to 1000 base pairs or more in length have also been disclosed in U.S. Pat. No. 6,410,277. The PCR primers are preferably located on the locus so that the polymorphic site is at least one base away from the 3' end of each PCR primer. However, it is understood that the PCR primers can be up to 1000 base pairs or more away from the polymorphism and still provide for amplification of a corresponding DNA fragment of 1000 base pairs or more that contains the polymorphism and can be used in typing assays. The PCR primers must not contain regions that are extensively self- or inter-complementary.

FRET probes are designed to span the sequence of the polymorphic site, preferably with the polymorphism located in the 3' most ⅔ of the oligonucleotide. In the preferred embodiment, the FRET probes will have incorporated at their 3' end a chemical moiety which, when the probe is annealed to the template DNA, binds to the minor groove of the DNA, thus enhancing the stability of the probe-template complex. The probes should have a length in the range of 12 to 17 bases, and with the 3' MGB, have a calculated melting temperature of 5 to 7° C. above that of the PCR primers. Probe design is disclosed in U.S. Pat. Nos. 5,538,848, 6,084,102, and 6,127,121.

Oligonucleotide probes for typing single nucleotide polymorphisms through use of Flap Endonuclease-mediated (Invader®, Third Wave Technologies, Madison Wis.) assays are also contemplated. In these assays, a flap endonuclease (cleavase) cuts a triple-helix created by hybridization of two overlapping oligonucleotides to the sequence that is typed (Lyamichev et al., Nat. Biotechnol., 17: 292-296, 1999). The sequence that is typed can be either soybean genomic DNA, cloned soybean genomic DNA or amplified soybean genomic DNA. Cleavage of one of the oligonucleotides that hybridizes to the sequence to be typed releases a flap that in turn forms a triple helix with a "FRET Cassette" oligonucleotide, resulting in a secondary cleavage reaction that releases a fluorescence resonance energy transfer (FRET) label. Embodiments where a single allele of a polymorphism is typed using a single FRET label have been described (Mein C. A., et al. Genome Res., 10: 330-343, 2000). In other embodiments of this method, two alleles of a polymorphism can be simultaneously typed by using different FRET labels. (Lyamichev et al., Ibid). High-throughput Flap Endonuclease-mediated assays have also been described that are suitable for creating sets of nucleotides for typing multiple polymorphisms (Olivier, et al., Nucleic Acids Res. 30(12): e53, 2002).

Isolated nucleic acid molecule compositions suitable for typing the polymorphisms of SEQ ID NOs: 1-37 with the cleavase can comprise at least one primary probe with a "universal" 5' flap sequence, at least one secondary or "Invader®" probe, and at least one "FRET" cassettes containing the labelled base and quencher base that contains sequences complementary to the "universal flap sequence" that is released from the primary probe upon cleavage. When the typed sequence is amplified soybean genomic DNA, flanking PCR primers similar to those described in the preceding paragraphs can also be used. The design of such probes requires only the provision of about 40 to 50 nucleotides on either side of the polymorphic base noted in Tables 6 or 7 or in any of the SEQ ID NOs: 1-32 or 34-37 molecular markers. General aspects of designing probes for Flap endonuclease assays are described in "Single Nucleotide Polymorphisms" ((Methods and Protocols) Volume 212, Chapter 16, V. Lyamichev and B. Neri pp 229-240 Humana Press. 2002).

Following typing of plants in the segregating population, a plant comprising at least one allele of a molecular marker associated with BSR resistance is selected. Selection can be accomplished by any method that permits for retention or transmission of the germplasm of the selected plant. Germplasm can be retained by any of a variety of methods including but not limited to seed collection, gamete collection, plant tissue collection, or plant tissue culture. Cultured plant tissue from the selected plant can be regenerated to yield a fully fertile plant comprising the germplasm of the selected plant. Germplasm can be transmitted by any of a variety of methods including but not limited to, pollen transfer from the selected plant to a pollen recipient or pollination of the selected plant by a distinct pollen donor plant.

In certain instances, the methods of the instant invention can further comprise the step of assaying selected soybean plants for BSR resistance. Phenotypic screening for BSR infection can be based on the percentage of stem infected. One method of assaying BSR resistance entails exposing plants to *P. gregata* by dipping roots in inoculum. After a period of growth, the plant stems are split open and the main stem examined for signs of infection. Plants are assigned a numerical rating according to the following scale 1 (no infection), 2 (1-10% infected), 3 (11-20% infected), 4 (21-35% infected), 5 (36-50% infected), 6 (51-65% infected), 7 (66%-75% infected), 8 (76-85% infected) and 9 (>85% infected).

Nonetheless, those skilled in the art will appreciate that any suitable method that provides for uniform inoculation of test plants by *P. gregata* and assessment of disease severity can be used in the methods described herein. These methods include but are not limited to: i) wounding and inoculation of the stems of individual plants (e.g. see Gray L E (1972) Plant Dis. Reptr. 56:580-581; Gray L E and Sinclair J B (1973) Plant Dis. Reptr. 57:853-854)); ii) root inoculation with the fungus (Sebastian S A et al., (1983) *Crop Sci*. 23:1214-1215) and iii) in-vitro disease resistance assays (see U.S. Pat. No. 4,937,970).

In another aspect, the soybean plant can show a comparative resistance compared to a non-resistant control soybean plant. In this aspect, a control soybean plant will preferably be genetically similar except for the BSR resistant allele or alleles in question. Such plants can be grown under similar conditions with equivalent or near equivalent exposure to the pathogen. Such comparisons will facilitate comparison and detection of BSR resistance alleles in a soybean plant.

The present invention also provides methods for determining whether a soybean plant is very resistant, resistant, substantially resistant, mid-resistant, comparatively resistant, partially resistant, mid-susceptible, or susceptible to BSR. More specifically, certain alleles of the polymorphisms contained in the molecular markers of SEQ ID NOs: 1-32, and 34-37 can be associated with varying degrees of resistance in a soybean plant. Also, certain combinations of certain alleles of the polymorphisms contained in the molecular markers of SEQ ID NOs: 1-32, and 34-37 can also be associated with varying degrees of resistance in a soybean plant.

Those skilled in the art will further appreciate that the use of a plurality of molecular markers associated with the BSR resistance loci can be advantageous in practicing the methods of this invention. The plurality of markers used may comprise multiple markers obtained from the group consisting of SEQ ID NOs: 1 through SEQ ID NO: 32 and SEQ ID NOs: 34 to SEQ ID NO: 37. Additional genetic markers associated with this region that can be used are as set forth in the Soybase website accessed through the Agricultural Research Service of the United States Department of Agriculture and Iowa State University on the world wide web at http://soybase.org/.

Soybean Plants Produced by the Methods of the Invention

The present invention also provides methods for obtaining soybean plants comprising alleles associated with BSR resistance. These soybean plants include but are not limited to, any soybean plants produced by a method wherein an allele associated with BSR resistance is identified with a molecular marker comprising a nucleic acid sequence selected from the group consisting of SEQ ID NOs: 1 through SEQ ID NO: 32 and SEQ ID NOs: 34 to SEQ ID NO: 37, fragments thereof, and complements of both. These soybean plants also include, but are not limited to, any soybean plants produced by a method wherein an allele associated with BSR resistance is identified with a nucleic acid comprising an oligonucleotide that is at least 90% identical to a sequence selected from the group consisting of SEQ ID NOs: 38 through SEQ ID NO: 164, fragments thereof, and complements thereof.

Plants produced by the methods of the present invention are soybean plants that are very resistant, resistant, substantially resistant, mid-resistant, comparatively resistant, or partially resistant to BSR. As used herein, a "resistant" soybean plant can be very resistant, resistant, substantially resistant, mid-resistant, comparatively resistant, or partially resistant to BSR.

The present invention also provides methods for determining whether a soybean plant produced by the methods of the invention is very resistant, resistant, substantially resistant, mid-resistant, comparatively resistant, partially resistant, mid-susceptible, or susceptible to BSR.

A disease resistance QTL for BSR may be introduced by the methods of this invention into an elite soybean inbred line. An "elite line" is any line that has resulted from breeding and selection for superior agronomic performance. Elite soybean plants with BSR resistance alleles are thus produced by the methods of this invention.

The BSR resistant soybean plants produced by the methods of this invention can also comprise one or more transgenes conferring traits such as herbicide tolerance, increased yield, insect control, fungal disease resistance, virus resistance, nematode resistance, bacterial disease resistance, *mycoplasma* disease resistance, modified oils production, high oil production, high protein production, germination and/or seedling growth control, enhanced animal and human nutrition, low raffinose, environmental stress resistance, increased digestibility, improved processing traits, improved flavor, nitrogen fixation, hybrid seed production, and/or reduced allergenicity. The transgenes in the soybean plants produced by the methods of this invention can also provide for production of industrial enzymes, pharmaceutical proteins, peptides, small molecules, biopolymers, and/or biofuels. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in soybean.

It is further understood that soybean plants produced by the methods of the present invention may exhibit a variety of different agronomic, processing, feed quality, food quality or other desired characteristics. One useful aspect of the instant invention is that it provides methods for obtaining soybean plants that comprise characteristics that are entirely distinct from those of the soybean plant that serves as the BSR disease resistance donor. For example, soybean plants produced by the methods of the invention can be of any relative maturity group. In an aspect of the invention, the maturity group is selected from the group consisting of 000, 00, 0, 1, 2, 3, 4, 5, 6, 7, 8, 9, and 10.

The present invention also provides for parts of the plants produced by the methods of the present invention. Plant parts, without limitation, include seed, endosperm, ovule and pollen. In a particularly preferred aspect of the present invention, the plant part is a seed. Plants or parts thereof produced by the methods of the present invention may be grown in culture and regenerated. Methods for the regeneration of *Glycine max* plants from various tissue types and methods for the tissue culture of *Glycine max* are known in the art (See, for example, Widholm et al., *In Vitro Selection and Culture-induced Variation in Soybean*, In Soybean: Genetics, Molecular Biology and Biotechnology, Eds. Verma and Shoemaker, CAB International, Wallingford, Oxon, England (1996). Regeneration techniques for plants such as *Glycine max* can use as the starting material a variety of tissue or cell types. With *Glycine max* in particular, regeneration processes have been developed that begin with certain differentiated tissue types such as meristems, Cartha et al., *Can. J Bot.* 59:1671-1679 (1981), hypocotyl sections, Cameya et al., *Plant Science Letters* 21: 289-294 (1981), and stem node segments, Saka et al., *Plant Science Letters*, 19: 193-201 (1980); Cheng et al., *Plant Science Letters*, 19: 91-99 (1980). Regeneration of whole sexually mature *Glycine max* plants from somatic embryos generated from explants of immature *Glycine max* embryos has been reported (Ranch et al., *In Vitro Cellular & Developmental Biology* 21: 653-658 (1985). Regeneration of mature *Glycine max* plants from tissue culture by organogenesis and embryogenesis has also been reported (Barwale et al., *Planta* 167: 473-481 (1986); Wright et al., *Plant Cell Reports* 5: 150-154 (1986).

The present invention also provides a container of soybean seeds in which greater than 50%, 60%, 70%, 80%, 90%, 95%, or 99% of the seeds comprising BSR resistance loci Rbs1, Rbs2, or Rbs3 where one or more alleles at one or more of their loci are selected from the group consisting of alleles defined by SEQ ID NOs: 1 through SEQ ID NO: 32 and SEQ ID NOs: 34 to SEQ ID NO: 37 and/or Table 6 or Table 7.

The container of soybean seeds can contain any number, weight, or volume of seeds. For example, a container can contain at least, or greater than, about 10, 25, 50, 100, 200, 300, 400, 500, 600, 700, 800, 900, 1000, 1500, 2000, 2500, 3000, 3500, 4000 or more seeds. In another aspect, a container can contain about, or greater than about, 1 gram, 5 grams, 10 grams, 15 grams, 20 grams, 25 grams, 50 grams, 100 grams, 250 grams, 500 grams, or 1000 grams of seeds. Alternatively, the container can contain at least, or greater than, about 0 ounces, 1 ounce, 5 ounces, 10 ounces, 1 pound, 2 pounds, 3 pounds, 4 pounds, 5 pounds, 10 pounds, 15 pounds, 20 pounds, 25 pounds, or 50 pounds or more seeds.

Containers of soybean seeds can be any container available in the art. For example, a container can be a box, a bag, a can, a packet, a pouch, a tape roll, a pail, or a tube. In another aspect, the seeds contained in the containers of soybean seeds can be treated or untreated soybean seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

Isolated Nucleic Acid Molecules—Loci, Primers and Probes

The present invention provides isolated nucleic acid molecules that are useful for introgressing alleles associated with BSR resistance into soybean plants. Such molecules include those nucleic acid molecules capable of detecting a polymorphism genetically or physically linked to a BSR locus. Such molecules can be referred to as markers. Additional markers can be obtained that are linked to BSR resistance locus Rbs by available techniques. In one aspect, the nucleic acid molecule is capable of detecting the presence or absence of a marker located less than 30, 20, 10, 5, 2, or 1 centimorgans from a BSR resistance locus. In another aspect, a marker exhibits a LOD score of 2 or greater, 3 or greater, or 4 or greater with BSR, using Qgene Version 2.23 (1996) and the default parameters provided therein. In another aspect, the nucleic acid molecule is capable of detecting a marker in a locus selected from the group BSR resistance locus Rbs1, Rbs2, and Rbs3. In a further aspect, a nucleic acid molecule is selected from the group consisting of SEQ ID NOs: 1 through SEQ ID NO: 164 fragments thereof, complements thereof, and nucleic acid molecules capable of specifically hybridizing to one or more of these nucleic acid molecules. The instant invention also provides isolated nucleic acids that can be used to type the alleles of the molecular markers associated with SEQ ID NOs: 1 through SEQ ID NO: 32 and SEQ ID NOs: 34 to SEQ ID NO: 37. In certain embodiments of the invention, the isolated nucleic acids provide for typing of the particular alleles of molecular markers associated with SEQ ID NOs: 1 through SEQ ID NO: 32 and SEQ ID NOs: 34 to SEQ ID NO: 37 that are disclosed in Table 6 and/or Table 7.

In another aspect of the present invention, a preferred marker nucleic acid molecule of the present invention shares between 80% and 100% or between 90% and 100% sequence identity with the nucleic acid sequence set forth in SEQ ID NOs: 1 through SEQ ID NO: 32 and SEQ ID NOs: 34 through SEQ ID NO: 164, the complements thereof or fragments thereof. In a further aspect of the present invention, a preferred isolated nucleic acid molecule of the present invention shares between 95% and 100% sequence identity with the sequence set forth in SEQ ID NOs: 1 through SEQ ID NO: 32 and SEQ ID NOs: 34 through SEQ ID NO: 164, complements thereof or fragments thereof. In a more preferred aspect of the present invention, a preferred nucleic acid molecule of the present invention shares between 98% and 100% sequence identity with the nucleic acid sequence set forth in SEQ ID NOs: 1 through SEQ ID NO: 32 and SEQ ID NOs: 34 through SEQ ID NO: 164 or complement thereof or fragments of either.

The isolated nucleic acids of this invention can also comprise oligonucleotides of at least 15 consecutive nucleotides that are homologous to SEQ ID NOs: 1-32 and SEQ ID NOs: 34 through 37 or the complements thereof. The oligonucleotides of at least 15 nucleotides in length can include or be immediately adjacent to one or more polymorphisms identified in Table 6 or Table 7. Such soybean loci have a nucleic acid sequence having at least 90% sequence identity, more preferably at least 95% or even more preferably for some alleles at least 98% and in many cases at least 99% sequence identity, to the sequence of the same number of nucleotides in either strand of a segment of soybean DNA which includes or is adjacent to the polymorphism. The nucleotide sequence of one strand of such a segment of soybean DNA may be found in a sequence in the group consisting of SEQ ID NOs: 1-32, 34-37. It is understood by the very nature of polymorphisms that for at least some alleles there will be no identity to the disclosed polymorphism, per se. Thus, sequence identity can be determined for sequence that is exclusive of the disclosed polymorphism sequence. In other words, it is anticipated that additional alleles for the polymorphisms disclosed herein may exist, can be easily characterized by sequencing methods, and can be used for genotyping. For example, one skilled in the art will appreciate that for a single nucleotide polymorphism where just two polymorphic residues are disclosed (e.g. an "A" or a "G") can also comprise other polymorphic residues (e.g. a "T" and/or a "G"). The total length of the isolated oligonucleotides can be between about 15 to 100 nucleotides. In certain embodiments the oligonucleotides can be between 15 to 20, 15 to 30 or 15 to 40 nucleotides in length.

The polymorphisms in each locus are identified more particularly in Table 6 and Table 7. SNPs are particularly useful as genetic markers because they are more stable than other classes of polymorphisms and are abundant in the soybean genome. SNPs can result from insertions, deletions, and point mutations. In the present invention a SNP can represent a single indel event, which may consist of one or more base pairs, or a single nucleotide polymorphism. Polymorphisms shared by two or more individuals can result from the individuals descending from a common ancestor. When a large set of crop lines is considered, and multiple lines have the same allele at a marker locus, it is necessary to ascertain whether IBS at the marker locus is a reliable predictor of IBD at the chromosomal region surrounding the marker locus. A good indication that a number of marker loci in a segment are enough to characterize IBD for the segment is that they can predict the allele present at other marker loci within the segment. The stability and abundance of SNPs in addition to the fact that they rarely arise independently makes them useful in determining IBD.

For many genotyping applications it is useful to employ as markers polymorphisms from more than one locus. Thus, one aspect of the invention provides a collection of nucleic acid molecules that permit typing of polymorphisms of different loci. The number of loci in such a collection can vary but will be a finite number, e.g. as few as 2 or 5 or 10 or 25 loci or more, for instance up to 40 or 75 or 100 or more loci.

Another aspect of the invention provides isolated nucleic acid molecules which are capable of hybridizing to the polymorphic soybean loci of this invention. In certain embodiments of the invention, e.g. which provide PCR primers, such molecules comprise at least 15 nucleotide bases. Polymerase chain reactions (PCR) to obtain amplified DNA segments can be accomplished with using primer pairs that are capable of hybridizing to the proximal sequences that define a polymorphism in its double-stranded form (U.S. Pat. No. 4,683,202; U.S. Pat. No. 4,582,788; and U.S. Pat. No. 4,683,194). Molecules useful as primers can hybridize under high stringency conditions to a one of the strands of a segment of DNA in a polymorphic locus of this invention. Primers for amplifying DNA are provided in pairs, i.e. a forward primer and a reverse primer. One primer will be complementary to one strand of DNA in the locus and the other primer will be complementary to the other strand of DNA in the locus, i.e. the sequence of a primer is preferably at least 90%, more preferably at least 95%, identical to a sequence of the same number of nucleotides in one of the strands. It is understood that such primers can hybridize to sequence in the locus which is distant from the polymorphism, e.g. at least 5, 10, 20, 50, 100, 200, 500 or up to about 1000 nucleotide bases away from the polymorphism. Design of a primer of this invention will depend on factors well known in the art, e.g. avoidance or repetitive sequence.

Isolated nucleic acid molecules of this invention can also be used as hybridization probes for polymorphism assays. In one aspect of the invention such probes are oligonucleotides comprising at least 12 nucleotide bases and a detectable label. The purpose of such a molecule is to hybridize, e.g. under high stringency conditions, to one strand of DNA in a segment of nucleotide bases which includes or is adjacent to the polymorphism of interest in an amplified part of a polymorphic locus. Such oligonucleotides are preferably at least 90%, more preferably at least 95%, identical to the sequence of a segment of the same number of nucleotides in one strand of soybean DNA in a polymorphic locus. The detectable label can be a radioactive element or a dye. In preferred aspects of the invention, the hybridization probe further comprises a fluorescent label and a quencher, e.g. for use hybridization probe assays of the type known as Taqman® assays, available from AB Biosystems.

Isolated nucleic acid molecules of the present invention are capable of hybridizing to other nucleic acid molecules including, but not limited to, soybean genomic DNA, cloned soybean genomic DNA, and amplified soybean genomic DNA under certain conditions. In this instance, the soybean genomic DNA, cloned soybean genomic DNA, and amplified soybean genomic DNAs that hybridize to the isolated nucleic acid molecules of the present invention are at least 70% identical to the DNA sequences of SEQ ID NOs: 1-32, 34-37 or the complements thereof. In other embodiments, the soybean genomic DNA, cloned soybean genomic DNA, and amplified soybean genomic DNAs that hybridize to the isolated nucleic acid molecules of the present invention are at least 70%, 80%, 90%, 95%, 98% or 99% identical to the DNA sequences of SEQ ID NOs: 1-32, 34-37 or the complements thereof. As used herein, two nucleic acid molecules are said to be capable of hybridizing to one another if the two molecules are capable of forming an anti-parallel, double-stranded nucleic acid structure. A nucleic acid molecule is said to be the "complement" of another nucleic acid molecule if they exhibit "complete complementarity" i.e., each nucleotide in one sequence is complementary to its base pairing partner nucleotide in another sequence. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules which hybridize to other nucleic acid molecules, e.g. at least under low stringency conditions are said to be "hybridizable cognates" of the other nucleic acid molecules. Conventional stringency conditions are described by Sambrook et al., *Molecular Cloning, A Laboratory Manual*, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985), each of which is incorporated herein by reference. Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 μg/mL nonspecific DNA (e.g., sonicated salmon sperm DNA) with washing at 0.5×SSC, 0.5% SDS at 65° C., for high stringency.

Isolated nucleic acid molecule of the present invention includes those that will specifically hybridize to one or more of the nucleic acid molecules set forth in SEQ ID NOs: 1 through SEQ ID NO: 164, the complements thereof, or fragments thereof under moderately stringent conditions of 2.0×SSC, 0.5% SDS, and 65° C. In other aspects of the invention, a nucleic acid of the present invention will specifically hybridize to one or more of the nucleic acid molecules set forth in SEQ ID NOs: 1 through SEQ ID NO: 32 and SEQ ID NOs: 34 through SEQ ID NO: 164 or complements or fragments of either under high stringency conditions of 0.5×SSC, 0.5% SDS at 65° C. In one aspect of the present invention, a preferred marker nucleic acid molecule of the present invention has the nucleic acid sequence set forth in SEQ ID NOs: 1 through SEQ ID NO: 32 and SEQ ID NOs: 34 through SEQ ID NO: 164 or complements thereof or fragments of either.

An isolated nucleic acid molecule of the present invention can be any sized fragment and illustrative fragments include fragments of nucleic acid sequences set forth in SEQ ID NOs: 1 through SEQ ID NO: 32 and SEQ ID NOs: 34 through 164 and complements thereof. In one aspect, a fragment can be between 15 and 25, 15 and 30, 15 and 40, 15 and 50, 15 and 100, 20 and 25, 20 and 30, 20 and 40, 20 and 50, 20 and 100, 25 and 30, 25 and 40, 25 and 50, 25 and 100, 30 and 40, 30 and 50, and 30 and 100 nucleotides. In another aspect, the fragment can be greater than 10, 15, 20, 25, 30, 35, 40, 50, 100, or 250 nucleotides.

Genetic markers of the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers, such as single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al., 2003 Gen. Res. 13:513-523), microarray transcription profiles, DNA-derived sequences, and RNA-derived sequences that are genetically linked to or correlated with alleles of a QTL of the present invention can be utilized.

In one embodiment, nucleic acid-based analyses for the presence or absence of the genetic polymorphism can be used for the selection of seeds in a breeding population. A wide variety of genetic markers for the analysis of genetic polymorphisms are available and known to those of skill in the art. The analysis may be used to select for genes, QTL, alleles, or genomic regions (haplotypes) that comprise or are linked to a genetic marker.

Methods of Introgressing BSR Resistance by Selecting a Haplotype Associated with BSR Resistance The molecular markers and polymorphisms disclosed herein can be used in the identification of marker/trait associations which are inferred from statistical analysis of genotypes and phenotypes of the members of a population. These members may be individual organisms, e.g. soybean, families of closely related individuals, inbred lines, doubled haploids or other groups of closely related individuals. Such soybean groups are referred to as "lines", indicating line of descent. The population may be descended from a single cross between two individuals or two lines (e.g. a mapping population) or it may consist of individuals with many lines of descent. Each individual or line is characterized by a single or average trait phenotype and by the genotypes at one or more marker loci.

Several types of statistical analysis can be used to infer marker/trait association from the phenotype/genotype data, but a basic idea is to detect molecular markers, i.e. polymorphisms, for which alternative genotypes have significantly different average phenotypes. For example, if a given marker locus A has three alternative genotypes (AA, Aa and aa), and if those three classes of individuals have significantly different phenotypes, then one infers that locus A is associated with the trait. The significance of differences in phenotype may be tested by several types of standard statistical tests such as linear regression of molecular marker genotypes on phenotype or analysis of variance (ANOVA). Commercially available, statistical software packages commonly used to do this type of analysis include SAS Enterprise Miner (SAS Institute Inc., Cary, N.C.) and Splus (Insightful Corporation. Cambridge, Mass.). When many molecular markers are tested simultaneously, an adjustment such as Bonferonni correction is made in the level of significance required to declare an association.

For the purpose of QTL mapping, the markers included should be diagnostic of origin in order for inferences to be made about subsequent populations. Molecular markers based on SNPs are ideal for mapping because the likelihood that a particular SNP allele is derived from independent origins in the extant populations of a particular species is very low. As such, SNP molecular markers are useful for tracking and assisting introgression of QTLs, particularly in the case of haplotypes.

Often the goal of an association study is not simply to detect marker/trait associations, but to estimate the location of genes affecting the trait directly (i.e. QTLs) relative to the marker locations. In a simple approach to this goal, one makes a comparison among marker loci of the magnitude of difference among alternative genotypes or the level of significance of that difference. Trait genes are inferred to be located nearest the marker(s) that have the greatest associated genotypic difference. The genetic linkage of additional marker molecules can be established by a gene mapping model such as, without limitation, the flanking marker model reported by Lander et al., (Lander et al., 1989 Genetics, 121:185-199), and the interval mapping, based on maximum likelihood methods described therein, and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al., (1989), and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al., 1995 Genetics, 139:1421-1428). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen et al., (Jansen et al., 1994 Genetics, 136:1447-1455) and Zeng (Zeng 1994 Genetics 136:1457-1468). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al., 1995 Theor. Appl. Genet. 91:33-3).

An alternative to traditional QTL mapping involves achieving higher resolution by mapping haplotypes, versus individual markers (Fan et al., 2006 Genetics 172:663-686) as one of the limitations of traditional QTL mapping research has been the fact that inferences are restricted to the particular parents of the mapping population and the genes or gene combinations of these parental varieties. This approach tracks blocks of DNA known as haplotypes, as defined by polymorphic markers, which are assumed to be identical by descent in the mapping population. It has long been recognized that genes and genomic sequences may be identical by state (i.e., identical by independent origins) or identical by descent (i.e., through historical inheritance from a common progenitor) which has tremendous bearing on studies of linkage disequilibrium and, ultimately, mapping studies (Nordberg et al., 2002 Trends Gen.). Historically, genetic markers were not appropriate for distinguishing identical in state or by descent. However, newer classes of markers, such as SNPs (single nucleotide polymorphisms), are more diagnostic of origin. The likelihood that a particular SNP allele is derived from independent origins in the extant populations of a particular species is very low. Polymorphisms occurring in linked genes are randomly assorted at a slow, but predictable rate, described by the decay of linkage disequilibrium or, alternatively, the approach of linkage equilibrium. Consequences of this well-established scientific discovery are that long stretches of coding DNA, defined by a specific combination of polymorphisms, are very unique and extremely improbable of existing in duplication except through linkage disequilibrium, which is indicative of recent co-ancestry from a common progenitor. The probability that a particular genomic region, as defined by some combination of alleles, indicates absolute identity of the entire intervening genetic sequence is dependent on the number of linked polymorphisms in this genomic region, barring the occurrence of recent mutations in the interval. Herein, such genomic regions are referred to as haplotype windows. Each haplotype within that window is defined by specific combinations of alleles; the greater the number of alleles, the greater the number of potential haplotypes, and the greater the certainty that identity by state is a result of identity by descent at that region. During the development of new lines, ancestral haplotypes are maintained through the process and are typically thought of as 'linkage blocks' that are inherited as a unit through a pedigree. Further, if a specific haplotype has a known effect, or phenotype, it is possible to extrapolate its effect in other lines with the same haplotype, as determined using one or more diagnostic markers for that haplotype window.

This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well within the skill of the ordinary practitioner of the art.

Selection of appropriate mapping populations is important to map construction. The choice of an appropriate mapping population depends on the type of marker systems employed (Tanksley et al., *Molecular mapping in plant chromosomes. chromosome structure and function: Impact of new concepts* J. P. Gustafson and R. Appels (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted× adapted).

An $F_2$ population is the first generation of selfing. Usually a single $F_1$ plant is selfed to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., 1992 Proc. Natl. Acad. Sci. (USA) 89:1477-1481). However, as the distance between markers becomes larger (i.e., loci become more independent), the information in RIL populations decreases dramatically.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., 1992). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al., 1991 Proc. Natl. Acad. Sci. (U.S.A.) 88:9828-9832). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Determining Degrees of BSR Resistance

The phenotypic rating scale and definitions used herein to assess BSR resistance in soybean plants are included in Table 1. This rating scale provides the basis for disease ratings and determinations of resistance, immunity, or susceptibility herein. The main stems of plants exposed to *Philophora gregata* were split open and examined for browning and infection of pith and vascular tissue.

TABLE 1

Description of rating criteria used for BSR phenotyping.

| Phenotypic Results (% stem infected) | Rating |
|---|---|
| No infection | 1 |
| 1-10% | 2 |
| 11-20 | 3 |
| 21-35 | 4 |
| 36-50 | 5 |
| 51-65 | 6 |
| 66-75 | 7 |
| 76-85 | 8 |
| >85 | 9 |

Example 2

Mapping with SATT244 and Application to SNP Markers

The SSR maker SATT244 maps to LG J and is known to associate with BSR resistance (Bachman et al., *Crop Sci* 41:527-535 (2001)). Because the SNP markers of the present invention co-locate with SATT244, this corroborates the utility of the markers of the present invention for screening and introgressing BSR resistance. A mapping population was developed from the cross of WILL/PI507354. WILL is the determinant isoline of the variety Williams. PI507354 is a source of BSR resistance. Sixty-nine individuals were screened with the SSR marker SATT244. The same meiotic event which was used for the mapping population in this study was also used to map soybean SNPs on the Monsanto SNP map. SATT244 maps within the same region as significant SNP markers for BSR resistance. The resistant source allele for SATT244 is from PI507354 and is denoted by the number 3 in Table 5. The susceptible allele for SATT244 is from WILL and is denoted by the number 1. In this analysis, lines were assigned a BSR score of 1 for resistant plants and 3 for susceptible plants. Plants that had been rated moderately susceptible/resistant were assigned a score of 2. Table 2 summarizes the results.

TABLE 2

SATT244, an SSR marker which co-locates with the SNP markers provided in this invention, can be used to screen for BSR resistance.

| Percent Susceptible | SATT244 Allele | BSR Score | STD Error BSRScore | N |
|---|---|---|---|---|
| 54.5 | — | 2.09 | 0.10874 | 69 |
| 78 | 1 | 2.56 | 0.12244 | 36 |
| 47 | 2 | 1.94 | 0.18912 | 18 |
| 6.5 | 3 | 1.13 | 0.13333 | 15 |

Example 3

Mapping Population for BSR Resistance

The present invention includes SNP markers that are associated with BSR resistance. The markers were identified by evaluation of genotype and phenotype of progeny resulting from a cross between a BSR resistant parent and a BSR susceptible parent. A population was developed for interval mapping from the cross of a BSR resistance source AG3302 and a susceptible variety DKB25-51. From the DKB25-51/AG3302 population, seven F1 seeds were planted. From these plants, 15 F2 seeds were harvested from 2 plants and 14 F2 seeds were harvested from the other five plants for a total of 100 F2 seeds. Replicates of DKB25-51 and AG3302 were also grown. Seed was submitted for BSR phenotyping and genotyping.

Thirteen SNP markers from LG J were used to screen the population. SNP markers NS0115388, NS0096111, NS0125407, NS0097529, NS0117865, and NS0118789 (SEQ ID NOs: 8, 7, 17, 19, 24, and 31) were found to be useful in predicting the BSR reaction.

For each marker, the average BSR rating was calculated for the segregating progeny and the parents. Table 3 provides the average BSR ratings reported with respect to allelic state for the markers found to associate with BSR reaction: NS0115388, NS0096111, NS0125407, NS0117865, NS0118789, and NS0097529. Marker genotype for the parents and progeny is reported in terms of the resistant and susceptible parents' genotype, wherein both parents were homozygous for all markers assayed.

Table 3 also summarizes the average marker effects for the allelic state of each marker locus. The marker effect term is the difference between the average BSR ratings of the resistant and susceptible parents.

TABLE 3

Summary of BSR rating reported per marker genotype (homozygous resistant, homozygous susceptible, and heterozygous). Also reported is the marker effect, the difference between the average BSR scores of the resistant and susceptible parents

| | Marker Genotype | | | |
|---|---|---|---|---|
| Marker | Homozygous, Susceptible (DKB25-51) | Homozygous, Resistant (AG3302) | Heterozygous | Effect |
| NS0115388 | 4.67 | 1.09 | 1.40 | 3.58 |
| NS0096111 | 4.47 | 1.08 | 1.33 | 3.39 |
| NS0125407 | 4.67 | 1.05 | 1.24 | 3.62 |
| NS0117865 | 4.26 | 1.13 | 1.20 | 3.13 |
| NS0118789 | 4.14 | 1.14 | 1.20 | 3.01 |
| NS0097529 | 4.14 | 1.16 | 1.20 | 2.98 |

Example 4

Use of SNP Markers to Select for BSR Resistance

The SNP markers provided in the present invention can be used to select against BSR susceptibility and for BSR resistance. A modified BC1F2 population of 121 individuals was produced from the following cross (LN92-12033/A2553)/AG2107. Genotyping with ten SNP markers demonstrated marker NS0118789 (SEQ ID NO: 31) to be highly predictive of BSR reaction. The susceptible source allele was TT for this marker. The percentage plant resistant was calculated for each plant. Of the population of 121 plants, 83 had the TT allele at this marker and the mean of the percentage plant resistant was 8.54%. The favorable allele in this population was from LN92-12033. The mean for individuals homozygous CC for this marker was significantly higher at 57.65% (N=14). Heterozygous individuals (CT) had a mean of 48.15% plant resistant. Table 4 summarizes the analysis results ($R^2$=0.38). Screening a soybean population with the marker NS0118789 (SEQ ID NO: 31) allows for selecting for BSR resistance and against BSR susceptibility.

TABLE 4

Use of SNP marker NS0118789 in selecting for BSR resistance.

| NS0118789 Marker allele | Mean % Plant resistant | STD. Error of % Plant Resistant | Total |
|---|---|---|---|
| CC, CT, TT | 22.08 | 2.44 | 121 |
| CC | 57.65 | 8.94 | 14 |
| CT | 48.15 | 4.50 | 24 |
| TT | 8.54 | 1.28 | 83 |

Example 5

Association Study

In another aspect, SNP markers associated with BSR resistance were identified from an association study based on genotypic and phenotypic data of 390 soybean lines, including commercial varieties and experimental lines. Soybean lines were screened with 1,166 markers. Two markers NS0125407 (SEQ ID NO: 17) and NS0118789 (SEQ ID NO: 31) were found to be associated with BSR resistance. In this analysis, lines were assigned a score of 1 for resistant plants and 3 for susceptible plants. Plants that had been rated moderately susceptible/resistant were assigned a score of 2. Of 194 lines found to be polymorphic at NS0125407, 141 were homozygous AA while 53 were homozygous for CC. The mean BSR score using this marker for AA individuals was 2.19, and the mean BSR score for CC individuals was 1.13. The marker effect was 1.06 for NS0125407. Of 184 lines found to be polymorphic at NS0118789, 47 were homozygous CC with a mean BSR score of 1.11. The other 137 lines were homozygous TT and had a mean BSR score of 2.20. Table 5 summarizes the results of the association mapping. When screening with NS0125407, the favorable allele for BSR resistance marker is CC, and when screening with NS0118789, the favorable allele is CC.

TABLE 5

Two SNP markers NS0125407 and NS0118789 were found to be associated with BSR.

| Marker | Allele_1 | N_1 | Mean_1 | Allele_2 | N_2 | Mean_2 | $R^2$ | Effect | p-value | Total |
|---|---|---|---|---|---|---|---|---|---|---|
| NS0125407 | AA | 141 | 2.19 | CC | 53 | 1.13 | 0.29 | 1.06 | <0.0001 | 194 |
| NS0118789 | CC | 47 | 1.11 | TT | 137 | 2.20 | 0.30 | 1.09 | <0.0001 | 184 |

Table 6 summarizes validation experiments and includes SNP markers found to be useful in monitoring the selection or introgression of BSR resistance loci Rbs1, Rbs2, and Rbs3 into a soybean plant in a soybean breeding program. The haplotype of the resistance source is used to determine which Rbs allele is selected for in a breeding program. SNP markers found to be useful for screening for Rbs include NS0096111, NS0115388, NS0097529, NS0125407, NS0117865, and NS0118789 (SEQ ID NOs: 7, 8, 19, 17, 24, and 31). Other SNP markers on LG J which could be used to screen for BSR resistance include NS0136063, NS0116003, NS0121329, NS0097011, NS0205207, NS0205545, NS0136255, NS0202657, NS0205390, NS0202839, NS0206116, NS0205513, NS0098342, NS0204723, NS0205732, NS0205990, NS0205742, NS0097836, NS0115925, NS0203163, NS0203256, NS0205987, NS0204644, NS0205506, NS0203006, NS0102178, NS0203207, NS0119351, NS0202621, NS0205432, and NS0206363. (SEQ ID NOs: 1-6, 9-16, 18, 20-23, 25-30, 32, 33, 34-37).

TABLE 6

SNP markers useful for the introgression of BSR resistance loci Rbs1, Rbs2, and Rbs3 into soybean plants when used in conjunction with the known haplotype of the resistance source.

| Marker | Chr. Pos. | SEQ ID NO: | SNP Pos.[1] | Allele 1 | Allele 2 | SEQ ID NO. Forward Primer | SEQ ID NO. Reverse Primer | SEQ ID NO. Probe 1 | SEQ ID NO. Probe 2 |
|---|---|---|---|---|---|---|---|---|---|
| NS0136063 | 87.3 | 1 | 481 | A | C | 38 | 39 | 70 | 71 |
| NS0116003 | 93.1 | 2 | 381 | C | T | 40 | 41 | 72 | 73 |
| NS0121329 | 93.1 | 3 | 1344 | C | G | 42 | 43 | 74 | 75 |
| NS0097011 | 93.3 | 4 | 345 | ******** | GTAGTATA | 44 | 45 | 76 | 77 |
| NS0205207 | 93.6 | 5 | 173 | A | T | | | | |
| NS0205545 | 93.6 | 6 | 332 | A | G | | | | |
| NS0096111 | 94.8 | 7 | 431 | A | G | 46 | 47 | 78 | 79 |
| NS0115388 | 94.8 | 8 | 390 | C | T | 48 | 49 | 80 | 81 |
| NS0136255 | 94.8 | 9 | 214 | C | T | 50 | 51 | 82 | 83 |
| NS0202657 | 95.0 | 10 | 84 | C | T | | | | |
| NS0205390 | 95.2 | 11 | 132 | A | T | | | | |
| NS0202839 | 95.7 | 12 | 355 | C | T | | | | |
| NS0206116 | 96.2 | 13 | 618 | C | T | | | | |
| NS0205513 | 96.3 | 14 | 281 | A | C | | | | |
| NS0098342 | 97.0 | 15 | 66 | C | T | 52 | 53 | 84 | 85 |
| NS0204723 | 97.4 | 16 | 176 | C | T | | | | |
| NS0125407 | 98.1 | 17 | 925 | A | C | 54 | 55 | 86 | 87 |
| NS0205732 | 98.1 | 18 | 292 | A | G | | | | |
| NS0097529 | 98.7 | 19 | 380 | A | T | 56 | 57 | 88 | 89 |
| NS0205990 | 98.8 | 20 | 31 | A | G | | | | |
| NS0205742 | 98.9 | 21 | 150 | C | T | | | | |
| NS0097836 | 99.4 | 22 | 194 | A | G | 58 | 59 | 90 | 91 |
| NS0115925 | 99.4 | 23 | 639 | A | C | 60 | 61 | 92 | 93 |
| NS0117865 | 99.4 | 24 | 123 | A | T | 62 | 63 | 94 | 95 |
| NS0203163 | 100.3 | 25 | 159 | A | G | | | | |
| NS0203256 | 101.2 | 26 | 264 | A | G | | | | |
| NS0205987 | 101.2 | 27 | 53 | A | C | | | | |
| NS0204644 | 101.6 | 28 | 116 | A | C | | | | |
| NS0205506 | 102 | 29 | 97 | A | G | | | | |
| NS0203006 | 102.0 | 30 | 261 | A | G | | | | |
| NS0118789 | 102.0 | 31 | 155 | C | T | 64 | 65 | 96 | 97 |
| NS0102178 | 103.3 | 32 | 464 | A | G | 66 | 67 | 98 | 99 |
| NS0203207 | 103.5 | 33 | 176 | C | T | | | | |
| NS0119351 | 103.7 | 34 | 285 | C | T | 68 | 69 | 100 | 101 |
| NS0202621 | 108.3 | 35 | 56 | C | T | | | | |
| NS0205432 | 108.9 | 36 | 121 | C | T | | | | |
| NS0206363 | 109.9 | 37 | 310 | A | G | | | | |

[1]SNP Position: refers to the position of the SNP polymorphism in the indicated SEQ ID NO "*" denotes a single nucleotide deletion Example 6

Introgression of BSR Resistance into a Soybean Plant

Soybean breeders can use the SNP markers provided in the present invention to introgress BSR resistance into a BSR susceptible soybean plant. This is a useful tool for soybean variety development and germplasm improvement activities which allows a breeder to incorporate BSR resistant material into an agronomically elite, but BSR susceptible, variety. Notably, in North America, no-till practices are resulting in increasing disease pressure, elevating the demand in the market for disease resistant commercial soybean varieties.

The markers of the present invention allow breeders to determine the haplotype of the resistant source and thus to select progeny with the parental resistant haplotype in order to advance BSR resistant progeny without necessarily phenotyping for BSR per se. The utility of the markers provided in Table 6 is presented as an illustrative example for a soybean breeding program. A BSR resistant source (non-limiting examples are provided in Table 7) is the donor parent for one or more BSR resistant loci. Introgression is monitored by screening with one or more of the molecular markers NS0096111, NS0115388, NS0125407, NS0097529, NS0117865, and NS0118789 (SEQ ID NOs: 7, 8, 17, 19, 24, and 31). The resulting population is screened with one or more of the genetic markers NS0136063, NS0116003, NS0121329, NS0097011, NS0205207, NS0205545, NS0096111, NS0115388, NS0136255, NS0202657, NS0205390, NS0202839, NS0206116, NS0205513, NS0098342, NS0204723, NS0125407, NS0205732, NS0097529, NS0205990, NS0205742, NS0097836, NS0115925, NS0117865, NS0203163, NS0203256, NS0205987, NS0204644, NS0205506, NS0203006, NS0118789, NS0102178, NS0119351, NS0202621, NS0205432, and NS0206363 (SEQ ID NOs: 1-32, 34-37). Progeny with the haplotype of the resistant source and are predicted to be resistant to BSR are selected for advancement.

In a population with A1923 as the resistant source, the haplotype selected using markers NS0096111, NS0115388, NS0125407, NS0097529, NS0117865, and NS0118789 (SEQ ID NOs: 7, 8, 17, 19, 24, and 31) is characterized by AATTACATATCT (SEQ ID NO: 165).

TABLE 7

The following table provides the haplotypes of BSR resistance sources when screened with the markers provided.

| | Marker | | | | | | |
|---|---|---|---|---|---|---|---|
| Line | NS0136063 | NS0116003 | NS0121329 | NS0097011 | NS0096111 | NS0115388 | NS0136255 |
| A1923 | AC | CC | CG | ********,GTAGTA, ********GTAGTA | AA | TT | TT |
| A2247 | AA | CC | CC | — | AA | TT | — |
| AG0601 | CC | TT | GG | ******** | GG | CC | CC |
| AG1602 | AA | CC | CC | GTAGTATA | AA | TT | TT |
| AG1701 | AA | CC | CC | GTAGTATA | AA | TT | TT |
| AG2103 | AA | CC | CC | — | AA | TT | TT |
| AG2106 | AA | CC | CC | GTAGTATA | AA | TT | TT |
| AG2203 | AA | TT | GG | GTAGTATA | GG | — | CC |
| AG2405 | AA | TT | GG | GTAGTATA | GG | — | CC |
| AG2703 | AA | TT | GG | GTAGTATA | GG | CC | CC |
| AG3703 | AA | TT | GG | GTAGTATA | GG | CC | CC |
| BSR101 | AA | CC | CC | GTAGTATA | AA | TT | TT |
| BSR201 | AA | CC | CC | — | AA | TT | TT |
| DKB06-51 | — | CC | CC | GTAGTATA | AA | TT | TT |
| DKB09-52 | AA | CC | CC | ******** | AA | — | TT |
| DKB16-51 | AA | CT | — | ********,GTAGTA, ********GTAGTA | AG | CT | CT |
| DKB19-51 | AA | CC | CC | GTAGTATA | AA | TT | TT |
| DKB23-51 | AA | CT | CG | — | AG | CC | CT |
| DKB23-95 | AA | CC | CC | GTAGTATA | AA | TT | TT |
| DKB28-52 | AA | CC | CC | GTAGTATA | AA | TT | — |
| DKB31-52 | AA | TT | GG | GTAGTATA | AA | TT | TT |
| DKB32-51 | AA | TT | GG | GTAGTATA | GG | CC | CC |
| L78-4094 | AA | TT | GG | — | GG | CC | CC |
| PI507354 | AA | CC | CC | — | AA | TT | — |

| | Marker | | | | | | |
|---|---|---|---|---|---|---|---|
| Line | NS0098342 | NS0125407 | NS0097529 | NS0097836 | NS0115925 | NS0117865 | NS0118789 |
| A1923 | CC | AC | AT | — | AC | AT | CT |
| A2247 | — | CC | — | — | — | AA | CC |
| AG0601 | — | AA | TT | — | CC | TT | TT |
| AG1602 | — | CC | AA | GG | AA | AA | CC |
| AG1701 | — | CC | AA | — | AA | AA | CC |
| AG2103 | — | CC | AA | — | — | AA | CC |
| AG2106 | — | CC | AA | GG | AA | AA | CC |
| AG2203 | — | AA | TT | GG | AA | AA | TT |
| AG2405 | TT | AA | TT | GG | AA | AA | TT |
| AG2703 | TT | AA | TT | — | CC | TT | TT |
| AG3703 | TT | AA | TT | GG | CC | TT | TT |
| BSR101 | — | CC | AA | — | — | AA | CC |
| BSR201 | — | CC | AA | — | — | AA | CC |
| DKB06-51 | — | — | AA | GG | AA | AA | CC |

TABLE 7-continued

The following table provides the haplotypes of BSR resistance sources when screened with the markers provided.

| | | | | | | | |
|---|---|---|---|---|---|---|---|
| DKB09-52 | — | AA | TT | AA | CC | TT | TT |
| DKB16-51 | — | AA | TT | AA | CC | TT | TT |
| DKB19-51 | — | CC | AA | GG | — | — | CC |
| DKB23-51 | TT | AA | TT | — | CC | TT | TT |
| DKB23-95 | — | CC | AA | GG | AA | AA | CC |
| DKB28-52 | — | CC | AA | GG | — | AA | CC |
| DKB31-52 | — | CC | AA | GG | AA | AA | CC |
| DKB32-51 | TT | AA | TT | GG | CC | TT | TT |
| L78-4094 | TT | AA | AA | — | — | AA | CC |
| PI507354 | — | CC | — | — | — | AA | CC |

"—" indicates missing data.

The introgression of one or more resistance loci is achieved via one or more cycles of backcrossing to a recurrent parent with one or more preferred agronomic characteristics, accompanied by selection to retain the one or more BSR resistance loci from the donor parent using the markers of the present invention. This backcross procedure is implemented at any stage in variety development and occurs in conjunction with breeding for one or more traits of interest including transgenic and nontransgenic traits.

Alternatively, a forward breeding approach is employed wherein one or more BSR resistance loci can be monitored for successful introgression following a cross with a susceptible parent with subsequent generations genotyped for one or more BSR resistance loci and for one or more additional traits of interest, including transgenic and nontransgenic traits.

Using the markers provided, the haplotype of a BSR resistant source can be used to select resistant progeny. Such resistant progeny can then be advanced in a soybean breeding program. Using markers NS0096111, NS0115388, NS0125407, NS0097529, NS0117865, and NS0118789 (SEQ ID NOs: 7, 8, 17, 19, 24, and 31) progeny with resistant haplotypes can be selected. For populations with A1923 as the BSR resistance source, the haplotype is characterized by AATTACATATCT (SEQ ID NO: 165). For populations with A2247, the haplotype is characterized by AATTCC-AACC (SEQ ID NO: 166) (marker NS0097529 omitted). For populations with AG0601, AG2703, AG3703, and DKB32-51 as the BSR resistance source, the haplotype is characterized by GGCCAATTTTTT (SEQ ID NO: 167). For populations with AG1602, AG1701, AG2103, AG2106, BSR101, BSR201, DKB23-95, DKB28-52, and DKB31-52 as the BSR resistance source, the haplotype is characterized by AATTCCAAAACC (SEQ ID NO: 168). For populations with AG2203 and AG2405 as the sources of BSR resistance, the haplotype is characterized by GG-AATTAATT (SEQ ID NO: 169) (marker NS0115388 omitted). For populations with DKB06-51 as the source of BSR resistance, the haplotype is characterized by AATT-AAAACC (SEQ ID NO: 170) (marker NS0125407 omitted). For populations with DKB09-52 as the BSR resistance source, the haplotype is AA-AATTTTTT (SEQ ID NO: 171) (marker NS0115388 omitted). For populations with DKB16-51 as the BSR resistance source, the haplotype is characterized by AGCTAATTTTTT (SEQ ID NO: 172). For populations with DKB19-51 as the BSR resistance source, the haplotype is characterized by AATTCCAA-CC (SEQ ID NO: 173) (marker NS0117865 omitted). For populations with DKB23-51 as the BSR resistance source, the haplotype is characterized by AGCTAATTTTTT (SEQ ID NO: 172). For populations with L78-4094 as the BSR resistance source, the haplotype is characterized by GGCCAAAAAACC (SEQ ID NO: 174). For populations with PI507354 as the resistance source, the haplotype is characterized by AATTCC-AACC (SEQ ID NO: 166) (marker NS0097529 omitted).

Additional markers may be used to select for and introgress BSR resistance into a soybean plant. Non-limiting examples of flanking markers include NS0136063, NS0116003, NS0121329, NS0097011, NS0205207, NS0205545, NS0136255, NS0202657, NNO205390, NS0202839, NS0206116, NS0205513, NS0098342, NS0204723, NS0205732, NS0205990, NS0205742, NS0097836, NS0115925, NS0203163, NS0203256, NS0205987, NS0204644, NS0205506, NS0203006, NS0102178, NS0203207, NS0119351, NS0202621, NS0205432, and NS0206363. (SEQ ID NOs: 1-6, 9-16, 18, 20-23, 25-30, 32, 33, 34-37).

Example 7

Oligonucleotide Hybridization Probes Useful for Detecting Soybean Plants with BSR Resistance Loci Oligonucleotides can also be used to detect or type the polymorphisms associated with BSR resistance disclosed herein by hybridization-based SNP detection methods. Oligonucleotides capable of hybridizing to isolated nucleic acid sequences which include the polymorphism are provided. It is within the skill of the art to design assays with experimentally determined stringency to discriminate between the allelic states of the polymorphisms presented herein. Exemplary assays include Southern blots, Northern blots, microarrays, in situ hybridization, and other methods of polymorphism detection based on hybridization. Exemplary oligonucleotides for use in hybridization-based SNP detection are provided in Table 8. These oligonucleotides can be detectably labeled with radioactive labels, fluorophores, or other chemiluminescent means to facilitate detection of hybridization to samples of genomic or amplified nucleic acids derived from one or more soybean plants using methods known in the art.

TABLE 8

Oligonucleotide Hybridization Probes

| Marker | Marker SEQ ID | SNP Position | Hybridization Probe[1] | SEQ ID |
|---|---|---|---|---|
| NS0205207 | 5 | 173 | ctgcagatagaaggtt | 102 |
| NS0205207 | 5 | 173 | ctgcagattgaaggtt | 103 |
| NS0205545 | 6 | 332 | agaggctaaaaaggcc | 104 |
| NS0205545 | 6 | 332 | agaggctagaaaggcc | 105 |
| NS0202657 | 10 | 84 | ggtagtctcctccctt | 106 |
| NS0202657 | 10 | 84 | ggtagtcttctccctt | 107 |
| NS0205390 | 11 | 132 | ggaatcgtaaacgtaa | 108 |

TABLE 8-continued

Oligonucleotide Hybridization Probes

| Marker | Marker SEQ ID | SNP Position | Hybridization Probe[1] | SEQ ID |
|---|---|---|---|---|
| NS0205390 | 11 | 132 | ggaatcgttaacgtaa | 109 |
| NS0202839 | 12 | 355 | gggcccatctccgggc | 110 |
| NS0202839 | 12 | 355 | gggcccatttccgggc | 111 |
| NS0206116 | 13 | 618 | tagagagacctagaat | 112 |
| NS0206116 | 13 | 618 | tagagagatctagaat | 113 |
| NS0205513 | 14 | 281 | aatctgtaagagttgc | 114 |
| NS0205513 | 14 | 281 | aatctgtacgagttgc | 115 |
| NS0204723 | 16 | 176 | tgttgttccaaaagct | 116 |
| NS0204723 | 16 | 176 | tgttgttctaaaagct | 117 |
| NS0205732 | 18 | 292 | ttccttttattgttgc | 118 |
| NS0205732 | 18 | 292 | ttccttttgttgttgc | 119 |
| NS0205990 | 20 | 31 | aagaatgcacaagagc | 120 |
| NS0205990 | 20 | 31 | aagaatgcgcaagagc | 121 |
| NS0205742 | 21 | 150 | gatggaaccaattctg | 122 |
| NS0205742 | 21 | 150 | gatggaactaattctg | 123 |
| NS0203163 | 25 | 159 | attagcaaacaaagag | 124 |
| NS0203163 | 25 | 159 | attagcaagcaaagag | 125 |
| NS0203256 | 26 | 264 | tgctcaatatgttttt | 126 |
| NS0203256 | 26 | 264 | tgctcaatgtgttttt | 127 |
| NS0205987 | 27 | 53 | gtaatataaaccatag | 128 |
| NS0205987 | 27 | 53 | gtaatatacaccatag | 129 |
| NS0204644 | 28 | 116 | ttttcgttactgtgaa | 130 |
| NS0204644 | 28 | 116 | ttttcgttcctgtgaa | 131 |
| NS0205506 | 29 | 97 | agggaaagagagattc | 132 |
| NS0205506 | 29 | 97 | agggaaagggagattc | 133 |
| NS0203006 | 30 | 261 | ggattgttagtttgtt | 134 |
| NS0203006 | 30 | 261 | ggattgttggtttgtt | 135 |
| NS0203207 | 33 | 176 | tccctcagctcagctg | 136 |
| NS0203207 | 33 | 176 | tccctcagttcagctg | 137 |
| NS0202621 | 35 | 56 | gtgaaggaccttgtgt | 138 |
| NS0202621 | 35 | 56 | gtgaaggatcttgtgt | 139 |
| NS0205432 | 36 | 121 | ttcctatccgggtctc | 140 |
| NS0205432 | 36 | 121 | ttcctatctgggtctc | 141 |
| NS0206363 | 37 | 310 | gaggtgatattgctgt | 142 |
| NS0206363 | 37 | 310 | gaggtgatgttgctgt | 143 |

[1]polymorphic base is bolded and underlined

Example 8

Oligonucleotide Probes Useful for Detecting Soybean Plants with BSR Resistance Loci by Single Base Extension Methods Oligonucleotides can also be used to detect or type the polymorphisms associated with BSR resistance disclosed herein by single base extension (SBE)-based SNP detection methods. Exemplary oligonucleotides for use in SBE-based SNP detection are provided in Table 8. SBE methods are based on extension of a nucleotide primer that is hybridized to sequences immediately adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type certain polymorphisms disclosed in this invention are provided in Table 6 in the columns labeled "Forward Primer SEQ ID" and "Reverse Primer SEQ ID". Following amplification of the region containing the polymorphism, the PCR product is hybridized with an extension primer which anneals to the amplified DNA immediately adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

TABLE 9

Probes (extension primers) for Single Base Extension (SBE) assays.

| Marker | Marker SEQ ID NO | SNP Position | Probe (SBE) | Probe SEQ ID |
|---|---|---|---|---|
| NS0205207 | 5 | 173 | tttgatcctctgcagat | 144 |
| NS0205545 | 6 | 332 | gtaatgcatagaggcta | 145 |
| NS0202657 | 10 | 84 | tctaccgcaggtagtct | 146 |
| NS0205390 | 11 | 132 | tggctatggggaatcgt | 147 |
| NS0202839 | 12 | 355 | tggctctgcgggcccat | 148 |
| NS0206116 | 13 | 618 | gattgaaattagagaga | 149 |
| NS0205513 | 14 | 281 | tttctgacccaatctgt | 150 |
| NS0204723 | 16 | 176 | atttcgatttgttgttc | 151 |
| NS0205732 | 18 | 292 | tagatctttttcctttt | 152 |
| NS0205990 | 20 | 31 | ggaagacttaagaatgc | 153 |
| NS0205742 | 21 | 150 | cgacaggaggatggaac | 154 |
| NS0203163 | 25 | 159 | tatcagtaaattagcaa | 155 |
| NS0203256 | 26 | 264 | aacaacctttgctcaat | 156 |
| NS0205987 | 27 | 53 | atctacagagtaatata | 157 |
| NS0204644 | 28 | 116 | tggaattttttttcgtt | 158 |
| NS0205506 | 29 | 97 | aggatcaacagggaaag | 159 |
| NS0203006 | 30 | 261 | tttgggtgtggattgtt | 160 |
| NS0203207 | 33 | 176 | ggaagctactccctcag | 161 |
| NS0202621 | 35 | 56 | gataagtctgtgaagga | 162 |
| NS0205432 | 36 | 121 | acgctattttcctatc | 163 |
| NS0206363 | 37 | 310 | attttttgggaggtgat | 164 |

Example 9

Association Study Further Validating SNP Markers

The phenotypic rating scale and definitions used in this example to assess BSR resistance in soybean plants are included in Table 10. This rating scale provides the basis for disease ratings and determinations of resistance, immunity, or susceptibility in this example.

TABLE 10

Description of rating criteria used for BSR phenotyping in Example 10.

| Phenotypic Results | Rating |
|---|---|
| No Browning | 1 |
| Flecking of outer cortex or 1-2% stem flecking in stem | 2 |
| Uniform streaking of outer cortex or 3-9% streaking in stem | 3 |
| 10% solid browning of pith | 4 |
| 20% solid browning of pith | 5 |
| 30% solid browning of pith | 6 |
| 40% solid browning of pith | 7 |
| 50% solid browning of pith | 8 |
| >60% solid browning of pith | 9 |

An association study was conducted with 928 pre-commercial soybean lines. Seeds of each line were grown in sand, and the plants were then artificially inoculated by dipping roots into BSR inoculum. Ten replicates of each line were then transplanted to the field. Plants were examined for symptoms of BSR and rated between the R7-R8 stages according to Table 10. An average BSR rating was calculated from the phenotypic scores of the replicates of each line. In the association study, genotypic data from leaf tissue samples of 168 lines and genotypic data from seed core samples of 760 lines were used. SNP markers on Linkage group J were used for genotyping and single-marker associations are provided in FIG. 1.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

Various patent and non-patent publications are cited herein, the disclosures of each of which are, to the extent necessary, incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

What is claimed is:

1. A method of producing a population of soybean plants that comprise at least one allele conferring Brown Stem Rot resistance, the method comprising the steps of:

(A) genotyping at least one soybean plant from a first population of soybean plants with respect to one or more soybean genomic DNA markers selected from the group consisting of SEQ ID NOs: 13, 18, and 30, wherein said markers are indicative of an allele conferring Brown Stem Rot resistance; and (B) selecting from the first population based upon said genotyping at least one soybean plant comprising an allele of one or more of said soybean genomic DNA markers, wherein said allele confers Brown Stem Rot (BSR) resistance, and C) growing from said selected at least one soybean plant a second population of soybean plants, thereby producing a population of soybean plants that comprise at least one allele conferring Brown Stem Rot (BSR) resistance.

2. The method according to claim 1, wherein at least two soybean genomic DNA markers selected from the group consisting of SEQ ID NOs: 13, 18, and 30 are genotyped in at least one soybean plant from the first population of soybean plants in step (A).

3. The method according to claim 1, wherein at least the soybean genomic DNA marker of SEQ ID NO: 13 is genotyped in at least one soybean plant from the first population of soybean plants in step (A).

4. The method according to claim 1, further comprising the step of assaying the soybean plant selected in step (B) for resistance to a Brown Stem Rot-inducing fungus.

5. The method according to claim 4, wherein said Brown Stem Rot-inducing fungus is a *Philophora* sp.

6. The method of claim 1, further comprising the step of crossing the soybean plant selected in step (B) to another soybean plant.

7. The method of claim 1, further comprising the step of obtaining seed from the soybean plant selected in step (B).

8. The method of claim 1, comprising in step (A) further genotyping the at least one soybean plant from the first population of soybean plants with respect to SEQ ID NO: 33.

9. The method according to claim 1, wherein said soybean plant that is genotyped in step (A) is from a segregating population obtained by crossing at least one Brown Stem Rot resistant plant comprising at least one first genotype with at least one other plant comprising at least one second genotype.

10. A method of introgressing a Brown Stem Rot resistance allele into a soybean plant comprising the steps of:

(A) crossing at least one Brown Stem Rot resistant soybean plant with at least one Brown Stem Rot sensitive soybean plant in order to obtain a segregating population;

(B) genotyping at least one soybean plant in the segregating population with respect to a haplotype characterized by one or more soybean genomic DNA markers selected from the group consisting of SEQ ID NOs: 13, 18, and 30; and (C) selecting from the segregating population based upon said genotyping one or more soybean plants comprising a haplotype associated with Brown Stem Rot resistance, wherein the Brown Stem Rot resistance haplotype is associated with a Rbs Brown Stem Rot resistance locus, thereby introgressing a Brown Stem Rot resistance allele into a soybean plant.

11. The method of claim 10, wherein the Rbs Brown Stem Rot resistance locus comprises Rbs1, Rbs2, or Rbs3.

12. The method of claim 10, wherein the Rbs Brown Stem Rot resistance locus is selected from the group consisting of Rbs1, Rbs2, and Rbs3.

13. The method of claim 10, wherein the source of Rbs is elite germplasm.

14. The method of claim 10, wherein the source of Rbs is accession germplasm.

* * * * *